(12) United States Patent
Innes et al.

(10) Patent No.: US 9,816,102 B2
(45) Date of Patent: Nov. 14, 2017

(54) COMPOSITIONS AND SYSTEMS FOR CONFERRING DISEASE RESISTANCE IN PLANTS AND METHODS OF USE THEREOF

(71) Applicant: INDIANA UNIVERSITY RESEARCH & TECHNOLOGY CORPORATION, Indianapolis, IN (US)

(72) Inventors: Roger Innes, Bloomington, IN (US); Sang Hee Kim, Bloomington, IN (US); Dong Qi, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 133 days.

(21) Appl. No.: 14/427,753

(22) PCT Filed: Sep. 4, 2013

(86) PCT No.: PCT/US2013/057979
§ 371 (c)(1),
(2) Date: Mar. 12, 2015

(87) PCT Pub. No.: WO2014/042923
PCT Pub. Date: Mar. 20, 2014

(65) Prior Publication Data
US 2015/0247163 A1 Sep. 3, 2015

Related U.S. Application Data

(60) Provisional application No. 61/700,500, filed on Sep. 13, 2012.

(51) Int. Cl.
*C12N 15/82* (2006.01)
*C07K 14/005* (2006.01)
*C07K 14/21* (2006.01)

(52) U.S. Cl.
CPC ........ *C12N 15/8281* (2013.01); *C07K 14/005* (2013.01); *C07K 14/21* (2013.01)

(58) Field of Classification Search
None
See application file for complete search history.

(56) References Cited

U.S. PATENT DOCUMENTS

| | | | |
|---|---|---|---|
| 4,945,050 A | 7/1990 | Sanford et al. | |
| 5,023,179 A | 6/1991 | Lam et al. | |
| 5,096,825 A | 3/1992 | Barr et al. | |
| 5,110,732 A | 5/1992 | Benfey et al. | |
| 5,268,463 A | 12/1993 | Jefferson | |
| 5,364,780 A | 11/1994 | Hershey et al. | |
| 5,380,831 A | 1/1995 | Adang et al. | |
| 5,399,680 A | 3/1995 | Zhu et al. | |
| 5,401,836 A | 3/1995 | Baszczynski et al. | |
| 5,436,391 A | 7/1995 | Fujimoto et al. | |
| 5,459,252 A | 10/1995 | Conkling et al. | |
| 5,466,785 A | 11/1995 | De Framond | |
| 5,563,055 A | 10/1996 | Townsend et al. | |
| 5,569,597 A | 10/1996 | Grimsley et al. | |
| 5,583,210 A | 12/1996 | Neill et al. | |
| 5,589,367 A | 12/1996 | Donson et al. | |
| 5,591,616 A | 1/1997 | Hiei et al. | |
| 5,602,321 A | 2/1997 | John | |
| 5,604,121 A | 2/1997 | Hilder et al. | |
| 5,608,142 A | 3/1997 | Barton et al. | |
| 5,608,144 A | 3/1997 | Baden et al. | |
| 5,608,149 A | 3/1997 | Barry et al. | |
| 5,612,454 A | 3/1997 | Kaminuma et al. | |
| 5,625,136 A | 4/1997 | Koziel et al. | |
| 5,633,363 A | 5/1997 | Colbert et al. | |
| 5,641,876 A | 6/1997 | McElroy et al. | |
| 5,703,409 A | 12/1997 | Fukumitsu et al. | |
| 5,750,386 A | 5/1998 | Conkling et al. | |
| 5,789,156 A | 8/1998 | Bujard et al. | |
| 5,792,931 A | 8/1998 | Duvick et al. | |
| 5,814,618 A | 9/1998 | Bujard et al. | |
| 5,837,876 A | 11/1998 | Conkling et al. | |
| 5,866,785 A | 2/1999 | Donson et al. | |
| 5,874,304 A | 2/1999 | Zolotukhin et al. | |
| 5,879,918 A | 3/1999 | Tomes et al. | |
| 5,885,801 A | 3/1999 | Rao | |
| 5,885,802 A | 3/1999 | Rao | |
| 5,886,244 A | 3/1999 | Tomes et al. | |
| 5,889,190 A | 3/1999 | Donson et al. | |
| 5,889,191 A | 3/1999 | Turpen | |
| 5,932,782 A | 8/1999 | Bidney | |

(Continued)

FOREIGN PATENT DOCUMENTS

| | | | |
|---|---|---|---|
| EP | 0138341 A2 | 4/1985 | |
| EP | 0295959 A2 | 6/1988 | |

(Continued)

OTHER PUBLICATIONS

Shao et al (2002), available online.*

(Continued)

*Primary Examiner* — Medina A Ibrahim
(74) *Attorney, Agent, or Firm* — Stinson Leonard Street

(57) ABSTRACT

Compositions, systems and methods are provided for conferring disease resistance to plant pathogens that use proteases to target plant substrate proteins inside plant cells. Briefly, the compositions, systems and methods are based upon plant substrate proteins that are targeted by pathogen-specific proteases and that activate nucleotide binding site-leucine rich repeat (NB-LRR) disease resistance proteins when cleaved by the protease. These substrate proteins are modified such that the endogenous protease recognition sequence is replaced by a protease recognition sequence specific to a different pathogen protease (i.e., a heterologous protease recognition sequence). The modified plant substrate protein therefore can be used in connection with its corresponding NB-LRR protein to activate resistance in response to cleavage by the heterologous pathogen-specific protease. When activated by the plant pathogen-specific protease, the pair initiates host defense responses thereto, including programmed cell death.

10 Claims, 17 Drawing Sheets

(56) References Cited

U.S. PATENT DOCUMENTS

| | | | |
|---|---|---|---|
| 5,981,840 | A | 11/1999 | Zhao et al. |
| 5,986,174 | A | 11/1999 | Barbour et al. |
| 5,990,389 | A | 11/1999 | Rao et al. |
| 6,177,611 | B1 | 1/2001 | Rice |
| 6,225,529 | B1 | 5/2001 | Lappegard et al. |
| 6,232,529 | B1 | 5/2001 | Singletary et al. |
| 6,338,168 | B1 | 1/2002 | Valentine |
| 6,664,387 | B2 | 12/2003 | Chung et al. |
| 6,858,778 | B1 | 2/2005 | Jung et al. |
| 6,921,815 | B2 | 7/2005 | Niu et al. |
| 7,009,087 | B1 | 3/2006 | Sewalt et al. |
| 7,060,491 | B1 | 6/2006 | Flannagan et al. |
| 7,083,948 | B1 | 8/2006 | Sassenfeld et al. |
| 7,102,057 | B2 | 9/2006 | Lanahan et al. |
| 7,122,641 | B2 | 10/2006 | Vedantham et al. |
| 7,220,356 | B2 | 5/2007 | Thommes et al. |
| 7,345,216 | B2 | 3/2008 | Keetman et al. |
| 7,476,722 | B2 | 1/2009 | Vedantham et al. |
| 7,494,805 | B2 | 2/2009 | Sisk et al. |
| 2002/0029392 | A1 | 3/2002 | Briggs et al. |
| 2004/0082770 | A1 | 4/2004 | Castle et al. |
| 2009/0239262 | A1 | 9/2009 | Rao et al. |

FOREIGN PATENT DOCUMENTS

| | | |
|---|---|---|
| EP | 0332581 A2 | 8/1988 |
| EP | 0292435 A1 | 11/1998 |
| EP | 0392225 B1 | 5/2003 |
| EP | 1721908 A1 | 11/2006 |
| WO | 9307278 A1 | 4/1993 |
| WO | 9321335 A2 | 10/1993 |
| WO | 9400977 | 1/1994 |
| WO | 9706268 A1 | 8/1996 |
| WO | 9706269 A1 | 2/1997 |
| WO | 9706269 A2 | 2/1997 |
| WO | 200011177 A2 | 2/1997 |
| WO | 9800533 A1 | 1/1998 |
| WO | 9820122 A1 | 5/1998 |
| WO | 9925821 A1 | 5/1999 |
| WO | 9925840 A1 | 5/1999 |
| WO | 9925853 A1 | 5/1999 |
| WO | 9925854 A1 | 5/1999 |
| WO | 9925855 A1 | 5/1999 |
| WO | 9943838 A1 | 9/1999 |
| WO | 0012733 A1 | 3/2000 |
| WO | 0017364 A2 | 3/2000 |
| WO | 0236782 A2 | 5/2002 |
| WO | 03006651 A2 | 1/2003 |
| WO | 03092360 A2 | 11/2003 |
| WO | 2004022771 A2 | 3/2004 |
| WO | 2005082923 A1 | 9/2005 |
| WO | 2006133182 A2 | 12/2006 |

OTHER PUBLICATIONS

McCormick, et al., Leaf disc transformation of cultivated tomato (L. esculentum) using *Agrobacterium tumefaciens*, Plant Cell Reports, 1986, vol. 5, pp. 81-84.

McNellis, et al., Glucocorticoid-inducible expression of a bacterial avirulence gene in transgenic *Arabidopsis* induces hypersensitive cell death, The Plant Journal, 1998, vol. 14, No. 2, pp. 247-257.

Miao, et al., Ammonia-Regulaed Expression of a Soybean Gene Encoding Cytosolic Glutamine Synthetase in Transgenic Lotus Corniculatus, The Plant Cell, vol. 3, pp. 11-22, 1991.

Mogen, et al., Upstream Sequences Other than AAUAAA Are Required for Efficent Messenger RNA 3'-End Formation in Plants, The Plant Cell, vol. 2, 1990, pp. 01261-01272.

Nicchitta, Christopher V., A platform for compartmentalized protein synthesis: protein translation and translocation in the ER, Membranes and Organelles, pp. 412-416.

Oliva, et al., Evidence that Tetracycline Analogs Whose Primary Target Is Not the Bacterial Ribosome Cause Lysis of *Escherichia coli*, Antimicrobial Agents adn Chemotherapy, 1992, pp. 913-919.

Paszkowski, et al., Direct Gene Tranfer to Plants, The EMBO Journal, vol. 3, No. 12, pp. 2717-2722, 1984.

Caviani, et al., Light-generated oligonucleotide arrays for rapid DNA sequence analysis, Proc. Natl. acad. Sci., vol. 91., pp. 5022-5026, 1994.

Pedersen, et al., Sequence Analysis and Characterization of a Maize Gene Encoding a High-sulfer Zein Protein of Mr 15,000, The Journal of Biological Chemistry, vol. 261, No. 14, pp. 6279-6284.

Reines, et al., Elongation factor SII-dependent transcription by RNA polymerase II through a sequence-specific DNA-binding protein, Proc. Natl. Acad. Sci., vol. 90, pp. 1917-1921.

Reznikoff, William S., The lactose operon-controlling elements: a comples paradigm, Molecular Microbiology, 1992, vol. 6, No. 17, pp. 2419-2422.

Riggs, et al., Stable transformation of tobacco by electroporation: Evidence for plasmid concatenation, Proc. Natl. Acad. Sci., vol. 83, pp. 5602-5606, 1986.

Sanfacon, et al., A dissection of the cauliflower mosaic virus polyadenylation signal, CSH Press, Genes, and Development, 1991, vol. 5, pp. 141-149.

Schena, et al., a steroid-inducible gene expression system for plant cells, Proc. Natl. Acad. Sci, vol. 88, pp. 10421-10425, 1991.

Schmidt, et al., A Novel Operon Organization Involving the Genes for Chorismate Synthase (Aromatic Biosynthesis Pathway) and Ribosomal GTPase Center Proteins (L11, L1, L10, L12: rpIKAJL) in Cyanobacterium Synechocystis PCC 6803, The Journal of Biological Chemistry, vol. 265, No. 36, pp. 27447-27467.

Schnell, et al., Signal Peptide analogs Derived from two Chloroplast Precursors Interact with the Signal Recognition System of the Chloroplast Envelope, The Journal of Biological Chemistry, 1991, vol. 266, No. 5, pp. 3335-3342.

Swideski, et al., The Arabidopsis PBS1 resistance gene encodes a member of a novel protein kinase subfamily, The Plant Journal, 2001, vol. 26, No. 1, pp. 101-112.

Teeri, et al., Gene fusions to lacZ reveal new expression patterns of chimeric genes in transgenic plants, The EMBO Journal, vol. 8, No. 2, pp. 343-350, 1989.

Van Tunen, et al., Cloning of the two chalcone flavanone isomerase genes from *Petunia hybrida*: coordinate, light-regulated and differential expression of flavonoid genes, The EMBO Journal, vol. 7, No. 5, pp. 1257-1263, 1988.

Walker, et al., DNA sequences required for anaerobic expression of the maize alchhol dehydrogenase 1 gene, Proc. Natl. Acad. Sci., vol. 84, pp. 6624-6628, 1987.

Wandelt, et al., Vicilin with carboxy-erminal KDEL is retained in the endoplasmic reticulum and accumulates to high levels in the leaves of transgenic plants, The Plant Journal, 1992, vol. 2, No. 2, pp. 181-192.

Weeks, et al., Rapid Production of Multiple Independent Lines of Fertile Transgenic Wheat (*Triticum aestivum*), Plant Physiol., 1993, vol. 102, pp. 1077-1084.

Wyborski, et al., Analysis of inducers of the *E.coli* lac repressor system in mammalian cells and whole animals, 1991, Nucleic Acids Research, vol. 19, No. 17, pp. 4647-4653.

Yamamoto, et al., Root-specific genes from tobacco and *Arabidopsis* homologous to an evolutionarily conserved gene family of membrane channel proteins, Nucleic Acids Research, vol. 18, No. 24, pp. 7449.

Yang, et al., Maize sucrose synthase-1 promoter directs phloem cell-specific expression of Gus gene in transgenic tobacco plants, Proc. Natl. Acad. Sci, vol. 87, pp. 4144-4148, 1990.

Yiji Xia, Proteases in pathogenesis and plant defense, Cellular Microbiology, Vo. 6, No. 10, pp. 905-913, 2004.

Zhao et al., Immunological Characterization and Chloroplast Localization of the Tryptophan Biosynthetic Enzymes of the Flowering Plant *Arabidopsis thaliana*, The Journal of Biological Chemistry, vol. 270, No. 11, 1995, pp. 6081-6087.

Ade et al., Indirect activation of a plant nucleotide binding site-leucine-rich repeat protein by a bacterial protease, Department of Biology, Indiana University, PNAS.org, 2007, vol. 107, No. 7, pp. 2531-2536.

(56) References Cited

OTHER PUBLICATIONS

Aoyama et al., A glucocorticoid-mediated transcriptional induction system in transgenic plants, The Plant Journal, 1997, vol. 11, No. 3, pp. 605-612.
Baim et al., A chimeric mammalian transactivator based on the lac repressor that is regulated by temerature and Isopropyl β-D-thiogalactopyranoside, Prox. Natl. Acad., Sci., USA, vol. 88., pp. 5072-5076, Jun. 1991.
Bansal, et al., Transient expression from cab-m1 and rbcS-m3 promoter sequences is different in mesophyll and bundle sheath cells in maize leaves, Proc. Natl. Acad. Sci., USA, vol. 89, pp. 3654-3658, Apr. 1992.
Belanger, et al.., Molecular Basis for Allelic Polymorphism of the Maize Globulin-1 Gene, 1991, Genetics Society of America, pp. 863-872.
Bogusz, et al., Nonlegume Hemoglobin Genes Retain Organ-Specific Expression in Heterologous Transgenic Plants, The Plant Cell., vol. 2, pp. 633641, Jul. 1990.
Bolte, et al., The N-myristoylated Rab-GTPase m-Rabmc is involved in post-Golgi trafficking events to the lytic vacuole in plant cells, Journal of Cell Science, vol. 117, No. 6, pp. 943-954.
Bruce, Barry D., The Paradox of Plastid transit peptides: conservation of function despite divergence in primary structure, Biochimica et Biophysica Acta, 1541, 2001, pp. 2-21.
Campbell, et al., Codon Usage in Higher Plants, Green Algae, and Cyanobacteria, Plant Physiol., 1990, vol. 92, pp. 1-11.
Canevascini, et al., Tissue-Specific Expression and Promoter Analysis of the Tobacco Itp1 Gene, Plant Physiol., 1996, vol. 1112, pp. 513-524.
Chalfie, et al., Green Fluorescent Protein as a Marker for Gene Expression, Science, vol. 263, pp. 802-805.
Chan, et al., Novel Gene Expression System for Plant Cells Based on Induction of a-Amylase Promoter by Carbohydrate Starvation, The Journal of Biological Chemistry, 1994, vol. 269, No. 25, pp. 17635-17641.
Chandler, et al., Two Regulatory Genes of the Maize Anthocyanin Pathway Are Homologous: Isolation of B Utilizing R Genomic Sequences, The Plant Cell, vol. 1, pp. 1175-1183, 1989.
Chisholm, et al., Molecular characterization of proteolytic cleavage sites of the *Pseudomonas syringae* effector AvrRpt2, PNAS, 2005, vol. 102, No. 6, pp. 2087-2092.
Christopherson, et al., Ecdysteroid-dependent regulation of genes in mammalian cells by a *Drosophila ecdysone* receptor and chimeric transactivators, Proc. Natl. Acad. Sci, USA, vol. 89, pp. 6314-6318, 1992.
Clark, et al., Mutations at teh Transit Peptide-Mature Protein Junction Separate Two Cleavage Events during Chloroplast Import of the Chlorophyll a/b-binding Protein, The Journal of Biological Chemistry, vol. 264, No. 29, 1989, pp. 17544-17550.
Clough, et al., Flroal dip: a simplified method for Agrobacterium-mediated transformation of *Arabidopsis thaliana*, The Plant Journal, 1989, vol. 16. No. 6, pp. 735-743.
Copeland, et al., Recombineering: A Powerful New Tool for Mouse Functional Genomics, Nature Reviews, Genetics, vol. 2, 2001, pp. 769-779.
Cordero, et al., Expresion of a maize proteinase inbibitor gene is induced in response to wounding and fungal infection: systemic wound-response of a monocot gene, The Plant Journal, 1994, vol. 6, No. 2, pp. 141-150.
Dangl, et al., Pivoting the Plant Immune System from Dissection to Deployment, Science, vol. 341, pp. 746-751.
Day, et al., Molecular Basis for the RIN4 Negative Regulation ofRPS2 Disease Resistance, The Plant Cell, vol. 17, 2005, pp. 1292-1305.
Degenkolb, et al., Structural Requirements of Tetracycline-Tet Repressor Interaction: Determination of Equilibrium Binding Constants for Tetracycline Analogs with the Tet Repressor, Antimicrobial Agents and Chemotherapy, 1991, pp. 1591-1595.
Della-Cioppa, et al., Protein Trafficking in Plant Cells, Plant Physiol., 1987, vol. 84, pp. 965-968.
Denecke, et al., Plant and mammalian sorting signals for protein retention in the endoplasmic reticulum contain a conserved epitope, The EMBO Journal, vol. 11, No. 6, pp. 2345-2355, 1992.
Deuschle, et al., Regulated expression of foreign genes in mammalian cells under the control of coliphage T3 RNA ploymerase and lac repressor, Proc. Natl. Acad., Sci., vol. 86, pp. 5400-5404, 1989.
Deyoung, et al., Activation of a plant nucleotide binding-leucine rich repeat disease resistance protein by a modified self protein, Cell Microbiol., 2012, vol. 14, No. 7, pp. 1071-1084.
Ebert et al., Identification of an essential upstream element in the nopaline synthase promoter by stable and transient assays, Proc. Natl. Acad. Sci, 1987, vol. 84, pp. 5745-5749.
Elroy-Stein, et al., Cap-independent translation of mRNA conferred by encephalomyocarditis virus 5' sequence improves the performance of the vaccinia virus/bacteriophage T7 hybrid expression system, Proc. Natl. Acad. Sci, 1989, vol. 86, pp. 6126-6130.
Emanuelsson, et al., Prediction of organellar targeting signals, Biochimica et Biophysica Acta 1541, 2001, pp. 114-119.
Fetter, et al., Interactions between Plasma Membrane Aquaporins Modulate Their Water Channel Activity, The Plant Cell, vol. 16, pp. 215-228, 2004.
Fodor, et al., Light-Directed, Spatially Addressable Parallel Chemical Synthesis, Research Article, 1991, pp. 767-773.
Franken, et al., The duplicated chalcone synthase genes C2 and Whp (white pollen) of *Zea mays* are independently regulated; evidence for translational control of Whp expression by the anthocyanin intensifying gene in, The EMBO Journal, vol. 10, No. 9, pp. 5605-2612, 1991.
Freyssinet, et al., Plants a a factory to produce molecules, Pure & Appl. Chem., vol. 70, No. 1, pp. 61-66, 1998.
Fuerst, et al., Transfer of the inducible lac repressor/operator system from *Escherichia coli* to a vaccinia virus expression vector, Proc. Natl. Acad. Sci, vol. 86., pp. 2549-2553, 1989.
Gordon-Kamm, et al., Transforation of Maize Cells and Regeneration of Fertile Transgenic Plants, The Plant Cell, vol. 2, pp. 603-618, 1990.
Gossen, et al., Tight control of gene expression in mammalian cells by tetracycline-responsive promoters, Proc. Natl. Acad. Sci., vol. 89, pp. 5547-5551, 1992.
Gotor, et al., Analysis of three tissue-specific elements from the wheat Cab-1 enhancer, The Plant Journal, 1993, vol. 3, No. 4, pp. 509-518.
Hush, et al., Quantification of microtubule dynamics in living plant cells using fluorescence redistribution after photobleaching, Journal of Cell Science 107, pp. 775-794, 1994.
Innes, et al., Molecular Analysis of Avirulence Gene avrRpt2 and Identification of a Putative Regulatory Sequence Common to All Known *Pseudomonas syringae* Avirulence Genes, Journal of Bacteriology, 1993, pp. 4859-4869.
Jefferson, Richard A., Assaying Chimeric Genes in Plants: The GUS Gene Fusion System, 1987, Plant Molecular Biology Reporter, vol. 5, No. 4, pp. 387-405.
Joshi, C.P., Putative polyadenylation signals in nuclear genes of higher plants: a compilation and analysis, Nucleic Acids Research, vol. 15, No. 23, 1987, pp. 9627-9640.
Kato, et al., Spectral Profiling for the Simultaneous Observation of Four Distinct Fluorescent Proteins and Detection of Protein-Protein Interaction via Fluorescence Resonance Energy Transfer in Tobacco Leaf Neclei, Breakthrough Technologies, Plant Physiology, 2002, pp. 931-942.
Kawamata, et al., Temporal and Spatial Pattern of Expression fo the Pea Phenylalanine Ammonia-Lyase Genet1 Promoter in Transgenic Tobacco, Plant Cell Physiol., vol. 38, No. 7, pp. 792-803, 1997.
Keller, et al., Specific expression of a novel cell wall hyroxyproline-rich glycoprotein gene in lateral root initiation, Genes & Development, vol. 3, pp. 1639-1646, 1989.
Keller, et al., Vascular-Specific Expression of the Bean GRP 1.8 Gene Is Negatively Regulated, The Plant Cell, vol. 3, pp. 1051-1061, 1991.
Kwon ,et al., Identification of a Light-Responseive Region of the Nuclear Gene Encoding the B Subunit of Chloroplast Glyceraldehyde 3-Phosphate Dehydrogenase from *Arabidopsis thaliana*, Plant Physiol, 1994, vol. 105, pp. 357-367.

(56) References Cited

OTHER PUBLICATIONS

Labow, et al., Conversion of the lac Repressor into an Allosterically Regulated Transcriptional Activator for Mammalian Cells, Molecular and Cellular Biology, 1990, pp. 3343-3356.

Lamppa, et al., The Chlorophyll a/b-binding Protein Inserts into the Thylakoids Independent of Its Cognate Transit Peptide, Teh Journal of Biological Chemistry, vol. 263, pp. 14996-14999, 1988.

Lawrence, et al., Alterations in the Chlamydomonas Plastocyanin Transit Peptide Have Distinct Effects on in Vitro Import and in Vivo Protein Accumulation, The Journal of Biological Chemistry, vol. 272, No. 33, pp. 20357-20363, 1997.

Lorito, et al., Genes from mycoparasitic fungi as a source for improving plant resistance to fungal pathogens, Proc. Natl. Acad. Sci, vol. 95, pp. 7860-7865, 1998.

* cited by examiner

COMPOSITIONS AND SYSTEMS FOR CONFERRING DISEASE RESISTANCE IN PLANTS AND METHODS OF USE THEREOF

CROSS-REFERENCE TO RELATED APPLICATIONS

This application claims priority to International Publication Number WO 2014/042923, filed on Sep. 4, 2013, which claims priority to U.S. Provisional Patent Application No. 61/700,500, filed on Sep. 13, 2012, which is incorporated by reference herein in its entirety.

STATEMENT REGARDING FEDERALLY SPONSORED RESEARCH OR DEVELOPMENT

This invention was made with government support under GM046451 awarded by the National Institutes of Health. The Government has certain rights in the invention.

INCORPORATION OF SEQUENCE LISTING

A paper copy of the Sequence Listing and a computer readable form of the sequence containing the file named "IURTC_2013-057-05_ST25", which is 17899 bytes in size (as measured in Microsoft WINDOWS® Explorer), are provided herein and are herein incorporated by reference. This Sequence Listing consists of SEQ ID NOs:1-28.

BACKGROUND

The present disclosure relates generally to plant genetics and plant molecular biology, and more particularly relates to compositions, systems and methods of conferring disease resistance to plant pathogens that express pathogen-specific proteases based on recognition of the pathogen-specific proteases in a plant cell.

Plant diseases are a serious limitation on agricultural productivity and influence the development and history of agricultural practices. A variety of plant pathogens are responsible for plant diseases including bacteria, fungi, insects, nematodes and viruses.

Incidence of plant diseases can be controlled by agronomic practices that include conventional breeding techniques, crop rotation and use of synthetic agrochemicals. Conventional breeding methods, however, are time-consuming and require continuous effort to maintain disease resistance as plant pathogens evolve. See, Grover & Gowthaman (2003) *Curr. Sci.* 84:330-340. Likewise, agrochemicals increase costs to farmers and cause harmful effects on the ecosystem. Because of such concerns, regulators have banned or limited the use of some of the most harmful agrochemicals.

Agricultural scientists now can enhance plant pathogen resistance by genetically engineering plants to express anti-pathogen polypeptides. For example, potatoes and tobacco plants have been developed that exhibit an increased resistance to foliar and soil-borne fungal pathogens. See, Lorito et al. (1998) *Proc. Natl. Acad. Sci. USA* 95:7860-7865. In addition, transgenic barley has been developed that exhibit an increased resistance to fungal pathogens. See, Horvath et al. (2003) *Proc. Natl. Acad. Sci. USA* 100:364-369. Moreover, transgenic corn and cotton plants have been developed to produce Cry endotoxins. See, e.g., Aronson (2002) *Cell Mol. Life Sci.* 59:417-425; and Schnepf et al. (1998) *Microbiol. Mol. Biol. Rev.* 62:775-806. Other crops, including potatoes, have been genetically engineered to contain similar endotoxins. See, Hussein et al. (2006) *J. Chem. Ecol.* 32:1-8; Kalushkov & Nedved (2005) *J. Appl. Entomol.* 129:401-406 and Dangl et al. (2013) *Science* 341: 746-751.

In light of the significant impact of plant pathogens on the yield and quality of plants, additional compositions, systems and methods are needed for protecting plants from plant pathogens.

BRIEF SUMMARY

Compositions, systems and methods are provided for conferring disease resistance to plant pathogens that express pathogen-specific proteases by modifying at least one member of a protein pair used by plants to detect the pathogen-specific proteases. These protein pairs enable plants to activate endogenous defense systems in response to the pathogen-specific proteases. Briefly, the compositions, systems and methods are based upon a protein pair in which one member of the pair is a nucleotide binding-leucine rich repeat (NB-LRR) disease resistance protein and the other member of the pair is a substrate protein of a pathogen-specific protease that physically associates with its native/corresponding NB-LRR protein and that activates the NB-LRR protein when cleaved by the pathogen-specific protease. The specificity of such pairs for a given pathogen-specific protease can be engineered by replacing an endogenous protease recognition sequence in the substrate protein with a recognition sequence for a pathogen-specific protease of interest (i.e., a heterologous protease recognition sequence).

The compositions include recombinant nucleic acid molecules having a nucleotide sequence that encodes a modified substrate protein of a pathogen-specific protease, where the modified substrate protein has a heterologous protease recognition sequence. The heterologous protease recognition sequence can be within, for example, an exposed loop of the modified substrate protein. Optionally, the recombinant nucleic acid molecule can have a nucleotide sequence that encodes a NB-LRR protein so that the nucleic acid molecule encodes the protein pair. For example, in one embodiment, a recombinant nucleic acid molecule having a nucleotide sequence that encodes the NB-LRR protein can be co-transformed with the recombinant nucleic acid molecules having a nucleotide sequence that encodes a modified substrate protein of a pathogen-specific protease so that the modified substrate protein and the NB-LRR protein are co-expressed. The NB-LRR protein can associate with, and can be activated by, the modified substrate protein of the pathogen-specific protease.

The compositions also include isolated, modified substrate proteins of pathogen-specific proteases as described herein, as well as active fragments and variants thereof.

The compositions also include nucleic acid constructs, such as expression cassettes and vectors, having a nucleotide sequence that encodes a modified substrate protein of a pathogen-specific protease as described herein operably linked to a promoter that drives expression in a plant cell, plant part or plant. Such a nucleic acid construct can be used to provide a modified substrate protein to a plant cell, plant part or plant that natively expresses the corresponding NB-LRR protein. The modified substrate protein can associate with, and can activate, the NB-LRR protein.

Optionally, the constructs, including expression cassettes and vectors, can include a nucleotide sequence that encodes a NB-LRR protein operably linked to a promoter that drives expression in a plant cell, plant part or plant. The nucleic acid constructs having a nucleotide sequence that encodes a modified substrate protein of a pathogen-specific protease and the nucleic acid constructs having a nucleotide sequence that encodes a NB-LRR protein can be co-expressed in a plant cell, plant part or plant. The NB-LRR protein can associate with, and can be activated by, the modified substrate protein of the pathogen-specific protease. Such a nucleic acid construct can be used to provide the protein pair to a plant cell, plant part or plant that does not natively express both members of the protein pair.

The compositions also include transformed plant cells, plant parts and plants having a nucleotide sequence that encodes at least one modified substrate protein of a pathogen-specific protease as described herein operably linked to a promoter that drives expression in a plant cell, plant part or plant. Optionally, the plant cells, plant parts and plants are transformed to include a nucleotide sequence that encodes a NB-LRR protein operably linked to a promoter that drives expression in the plant cell, plant part or plant. The NB-LRR protein can associate with, and can be activated by, the modified substrate protein of the pathogen-specific protease.

The systems include a nucleic acid construct having a nucleotide sequence for a first promoter that drives expression in a plant cell, plant part or plant operably linked to a nucleotide sequence that encodes a modified substrate protein of a pathogen-specific protease as described herein and a nucleotide sequence for a second promoter that drives expression in a plant cell, plant part or plant operably linked to a nucleotide sequence that encodes a NB-LRR protein. The NB-LRR protein can associate with, and can be activated by, the modified substrate protein. Such systems can be used to provide the protein pair to a plant cell, plant part or plant that does not natively express both members of the protein pair.

The systems also include a first nucleic acid construct having nucleotide sequence for a promoter that drives expression in a plant cell, plant part or plant operably linked to a nucleotide sequence that encodes a modified substrate protein of a pathogen-specific protease as described herein, and a second nucleic acid construct having a nucleotide sequence for a promoter that drives expression in a plant cell, plant part or plant operably linked to a nucleotide sequence that encodes a NB-LRR protein. Additional nucleic acid constructs also can be included in the system, where each construct has a nucleotide sequence that encodes a distinct modified substrate protein, each having a heterologous recognition sequence for a separate pathogen-specific protease. Although each modified substrate protein has a heterologous recognition sequence distinct from one another, each can associate with, and can activate, the NB-LRR protein. Alternatively, the first nucleic acid construct can encode more than one modified substrate protein, where each modified substrate protein has a heterologous recognition sequence distinct from one another and where each can associate with, and can activate, the NB-LRR protein. Alternatively, the second nucleic acid construct can encode one or more modified substrate proteins, where each modified substrate protein has a heterologous recognition sequence distinct from one another and where each can associate with, and can activate, the NB-LRR protein. Such systems can be used to provide the protein pair to a plant cell, plant part or plant that does not natively express the protein pair or can be used to provide more than one modified substrate protein to a plant cell, plant part or plant.

By way of example, the substrate protein of the pathogen-specific protease can be a PBS1 or a RIN4 homolog from *Arabidopsis thaliana*, and the NB-LRR protein can be a RPS5 or a RPS2 from *A. thaliana*, where the PBS1 or RIN4 homolog is modified to include a heterologous protease recognition sequence. As understood by those skilled in the art, "PBS1" refers to avrPphB susceptible 1. As understood by those skilled in the art, "RIN4" refers to Resistance To *Pseudomonas syringae* pv. *maculicola* 1 ("RPM1") Interacting Protein 4. As understood by those skilled in the art, "avrRpt2" refers to the bacterial avirulence gene from *Pseudomonas syringae* that encodes the "AvrRpt2" polypeptide having a role in plant-*P. syringae* interactions (see, Innes et al. (1993) *J. Bacteriol* 175:4859-4869). As understood by those skilled in the art, "avrPphB" refers to the bacterial avirulence gene from *P. syringae* that encodes the "AvrPphB" polypeptide having a role in plant—*P. syringae* interactions.

In view of the foregoing, the methods include introducing into a plant cell, plant part or plant at least one nucleic acid molecule, construct, expression cassette or vector as described herein to confer disease resistance to plant pathogens that express pathogen-specific proteases.

The compositions, systems and methods therefore find use in conferring disease resistance to plant pathogens by transferring to plant cells, plant parts or plants nucleotide sequences that encode at least one modified substrate protein of a pathogen-specific protease and optionally that encode a NB-LRR protein when such NB-LRR protein is not native to the plant cell, plant part or plant. The pair is thus engineered to be specific for a plant pathogen-specific protease by including in the modified substrate protein a heterologous protease recognition sequence for that plant pathogen-specific protease. When activated by the plant pathogen-specific protease, the pair initiates host defense responses thereto, including programmed cell death.

These and other features, objects and advantages of the present disclosure will become better understood from the description that follows. In the description, reference is made to the accompanying drawings, which form a part hereof.

BRIEF DESCRIPTION OF THE DRAWINGS

The features, objects and advantages other than those set forth above will become more readily apparent when consideration is given to the detailed description below. Such detailed description makes reference to the following drawings, wherein:

FIG. 1 is a photograph showing that RPS5 (a NB-LRR disease resistance protein) can be activated by AvrRpt2 (a plant pathogen-specific protease) when co-expressed with a modified PBS1 (a substrate protein for a plant pathogen-specific protease) containing an AvrRpt2 cleavage site. Indicated nucleic acid molecules were transiently expressed in *Nicotiana glutinosa* leaves by injecting *Agrobacterium tumefaciens* strains carrying the indicated nucleic acid molecules. Each nucleic acid molecule was under control of a dexamethasone-inducible promoter, and leaves were photographed about 24 hours after dexamethasone application. Visible leaf collapse indicates activation of programmed cell death.

FIG. 2 is a graph illustrating electrolyte leakage from *N. glutinosa* leaf disks inoculated with the same strains as used in FIG. 1. Increases in electrolyte leakage indicate loss of plasma membrane integrity due to cell death. PBS1$^{RCS2}$ indicates PBS1 in which its AvrPphB (a plant pathogen-specific protease) cleavage site (GDKSHVS; SEQ ID NO:1) was replaced with the AvrRpt2 cleavage site (VPKFGDW; SEQ ID NO:2).

FIG. 3 shows photographs of infected leaves from transgenic *A. thaliana* expressing PBS1$^{RCS2}$ (i.e., PBS1 in which the AvrPphB cleavage site was replaced with the AvrRpt2 cleavage site). Shown are leaves from five different primary transformants inoculated on the right side with *Pseudomonas syringae* strain DC3000(AvrRpt2). The photographs were taken 24 hours after inoculation, a time point at which untransformed *A. thaliana* leaves do not display cell death. The *A. thaliana* accession used for this experiment contained mutations in RIN4 and RPS2, which prevent activation of cell death by AvrRpt2 in the absence of modified PBS1.

Figure 8:
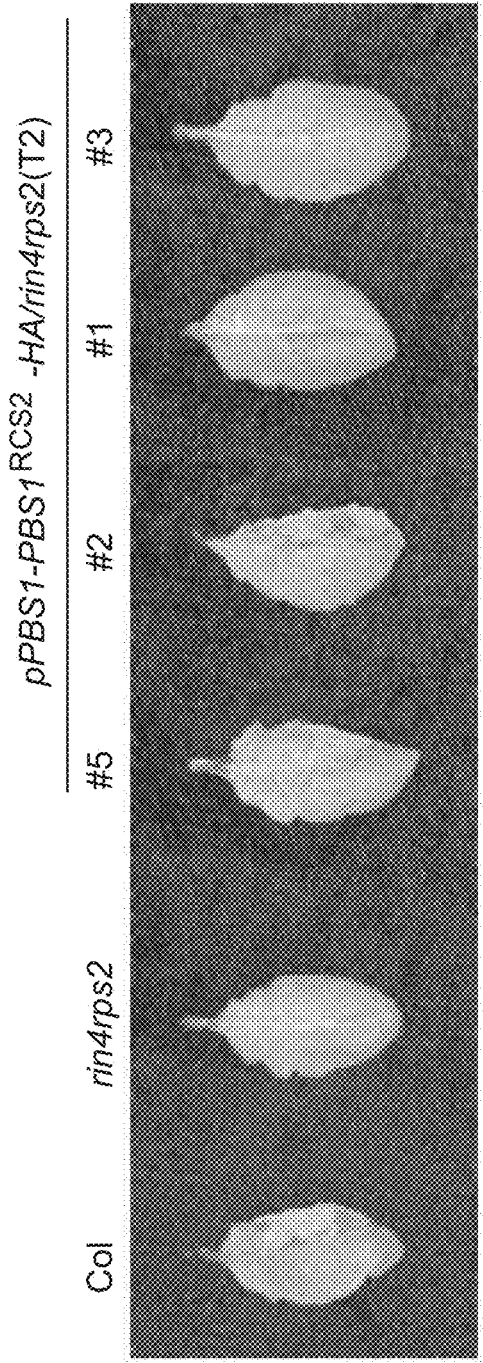

FIG. 8 is a photograph showing the induction of HR in transgenic lines 2 and 5 in response to inoculation with *P. syringae*, whereas lines 1 and 3 did not as discussed in Example 5. "Col" indicates the wild-type *Arabidopsis* parent.

Figure 9:
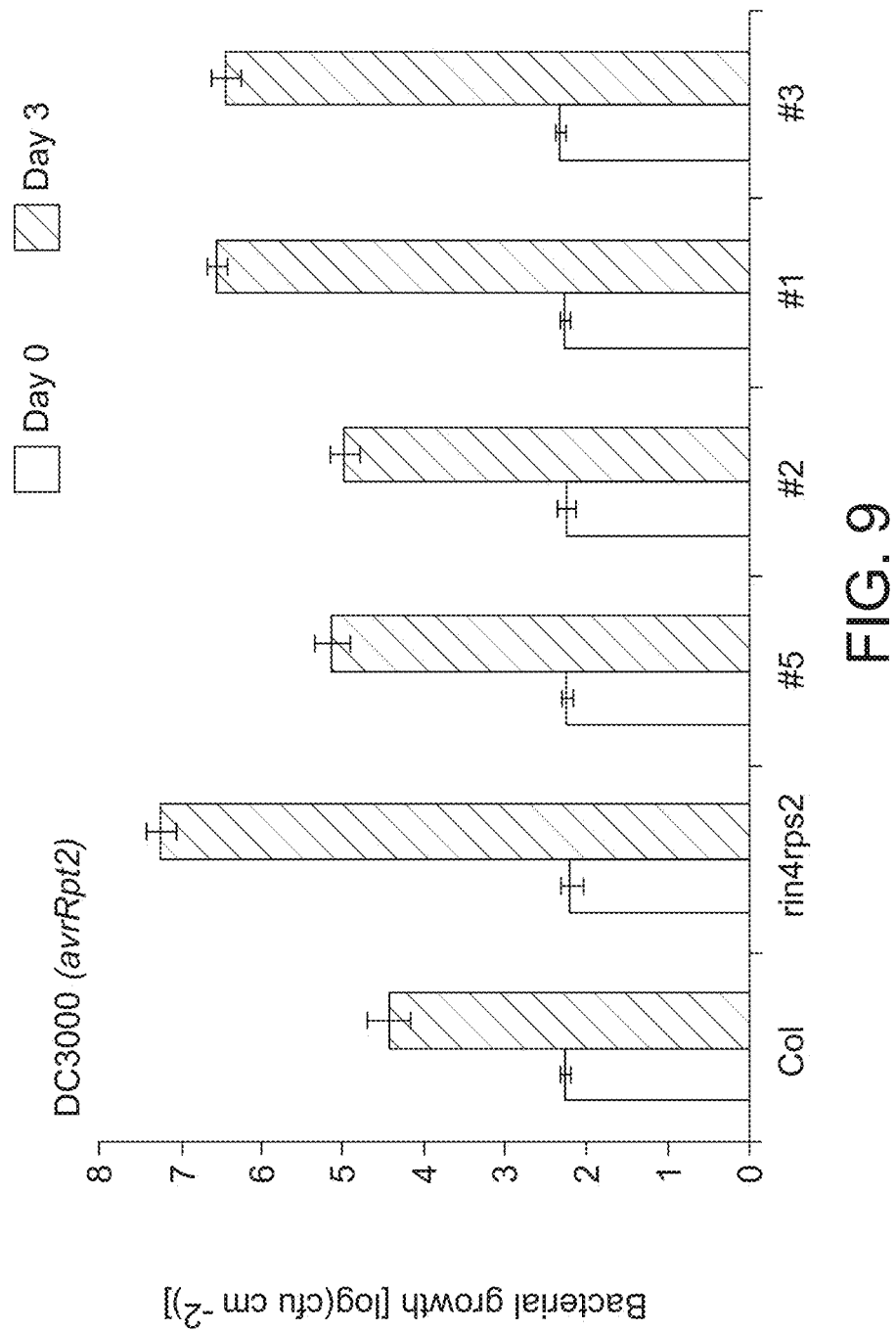

FIG. 9 is a graph illustrating that PBS1$^{RCS2}$ confers resistance to bacterial growth of DC3000(avrRpt2) in *Arabidopsis* as discussed in Example 5. Data represent mean cfu cm$^{-2}$ (n=4), and error bars denote standard deviation.

Figure 10:
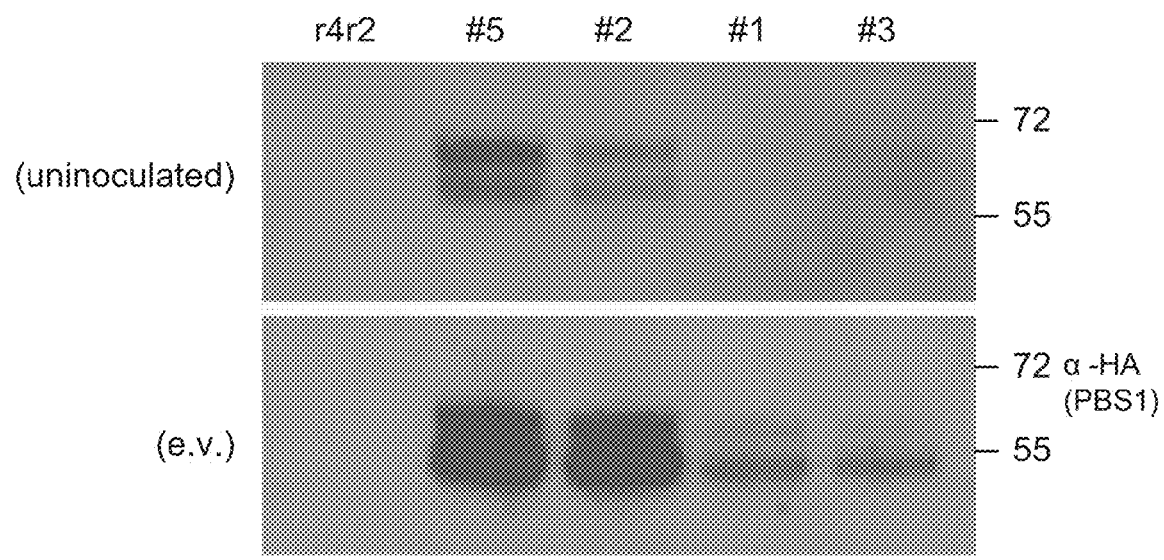

FIG. 10 contains immunoblots showing that resistance to bacterial growth of DC3000(avrRpt2) correlated with expression of PBS1$^{RCS2}$ as discussed in Example 5.

Figure 11:
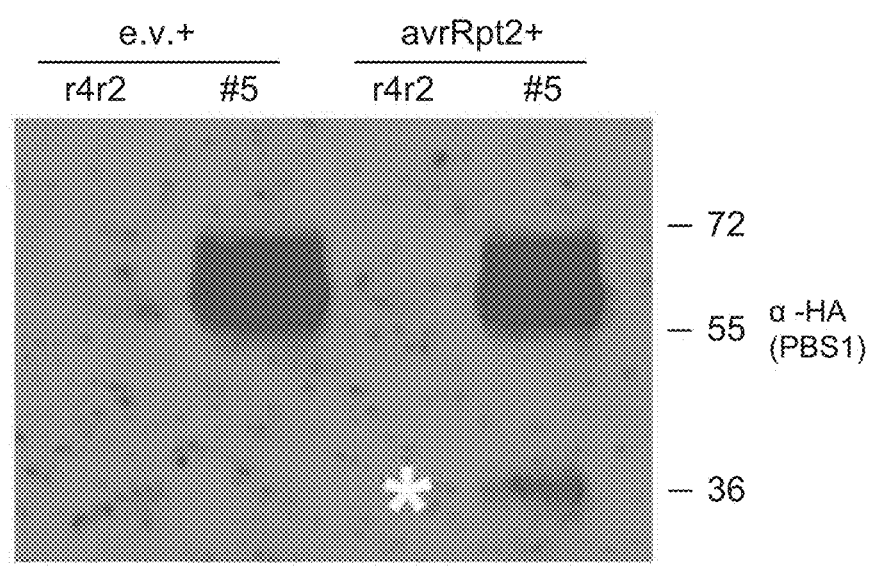

FIG. 11 is an immunoblot showing cleavage of PBS1$^{RCS2}$ expressed in transgenic *Arabidopsis* by AvrRpt2 delivered by DC3000 as discussed in Example 5. The asterisk indicates the expected size of the C-terminal PBS1$^{RCS2}$ cleavage product.

Figure 12:

FIG. 12 is a photograph showing that PBS1$^{RCS2}$ transgenic *Arabidopsis* also displayed HR 21 hours after injection with DC3000(avrPphB), demonstrating that native recognition specificity of RPS5 was retained in these transgenic lines as discussed in Example 5.

Figure 13:
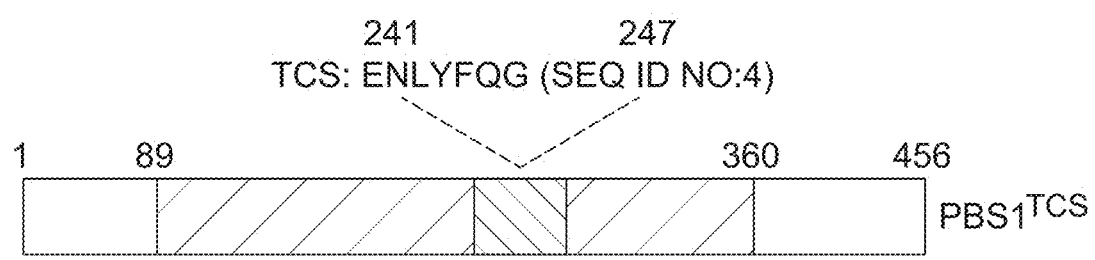

FIG. 13 is a representation of a PBS1$^{TCS}$ construct illustrating the replacement of the seven amino acids flanking the AvrPphB cleavage site with a TEV cleavage site as discussed in Example 5.

Figure 14:
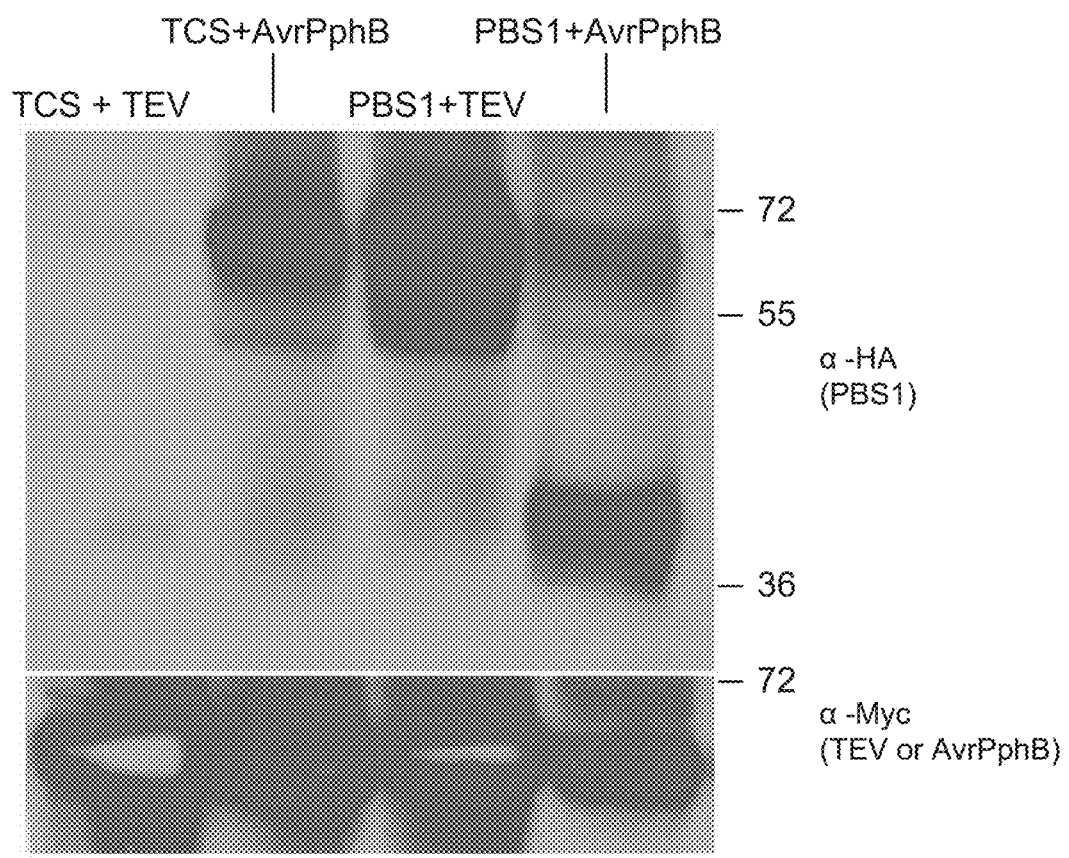

FIG. 14 contains immunoblots showing cleavage of PBS1$^{TCS}$-HA as detected by anti-HA (upper panel) as discussed in Example 5.

Figure 15:
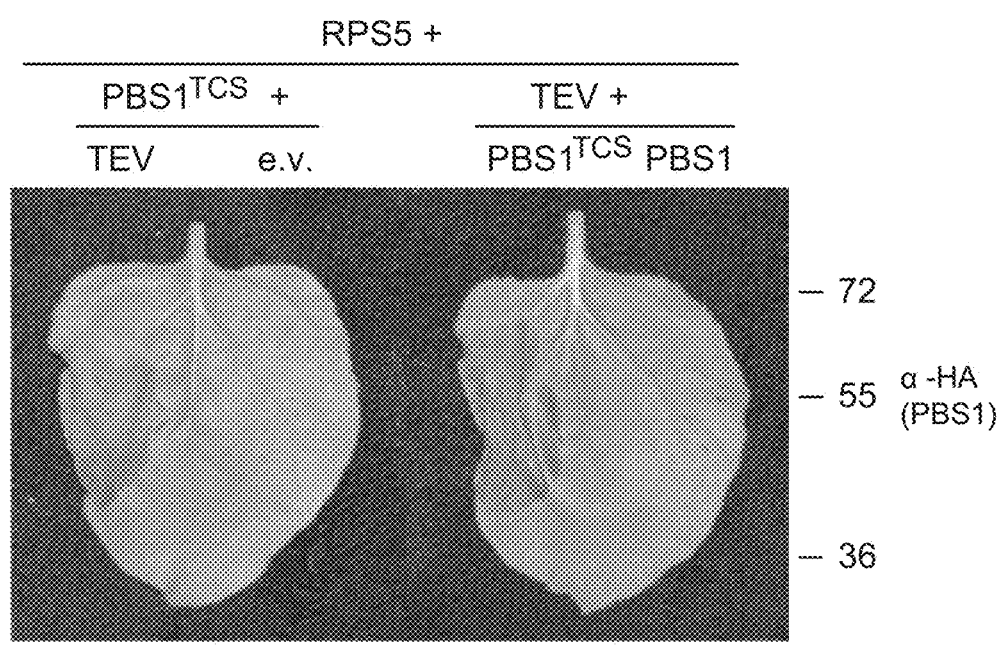

FIG. 15 is a photograph of *N. benthamiana* co-expressing PBS1$^{TCS}$ with TEV protease activated RPS5 as discussed in Example 5. The left side of each leaf was infiltrated with *Agrobacterium* strains that delivered PBS1$^{TCS}$, TEV protease and RPS5.

Figure 16:
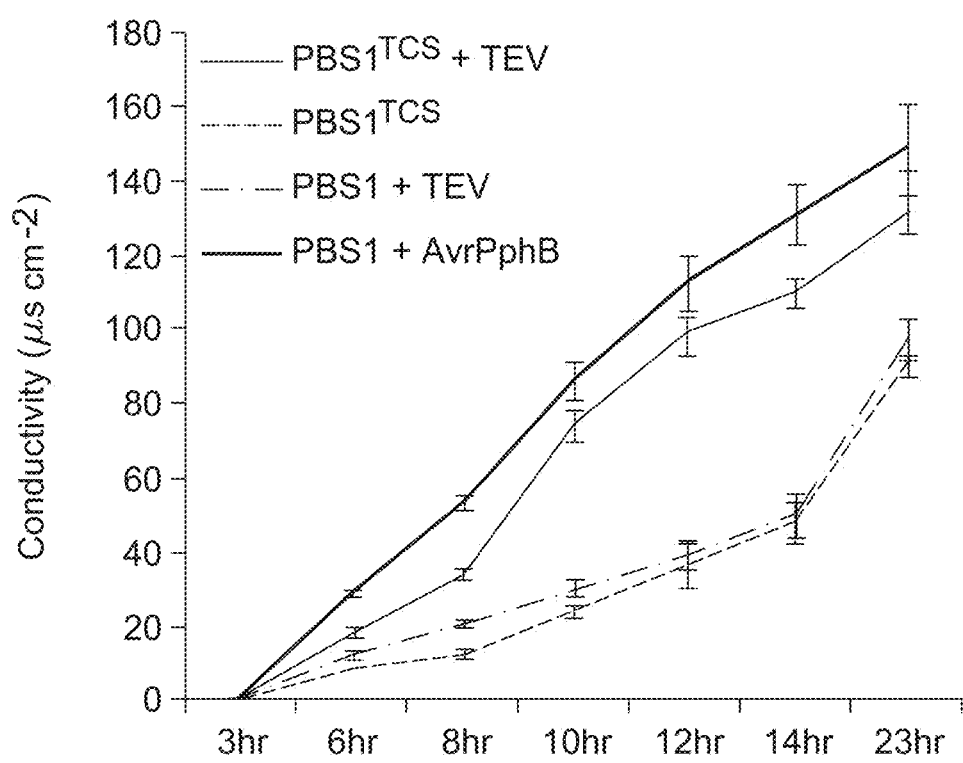

FIG. 16 is a graph illustrating that PBS1$^{TCS}$ with TEV protease induced RPS5-mediated cell death as indicated by electrolyte leakage. The level of electrolyte leakage was similar to that induced by wild-type PBS1 cleaved by AvrPphB as discussed in Example 5. Data represents the mean and standard deviation (n=4).

Figure 17:
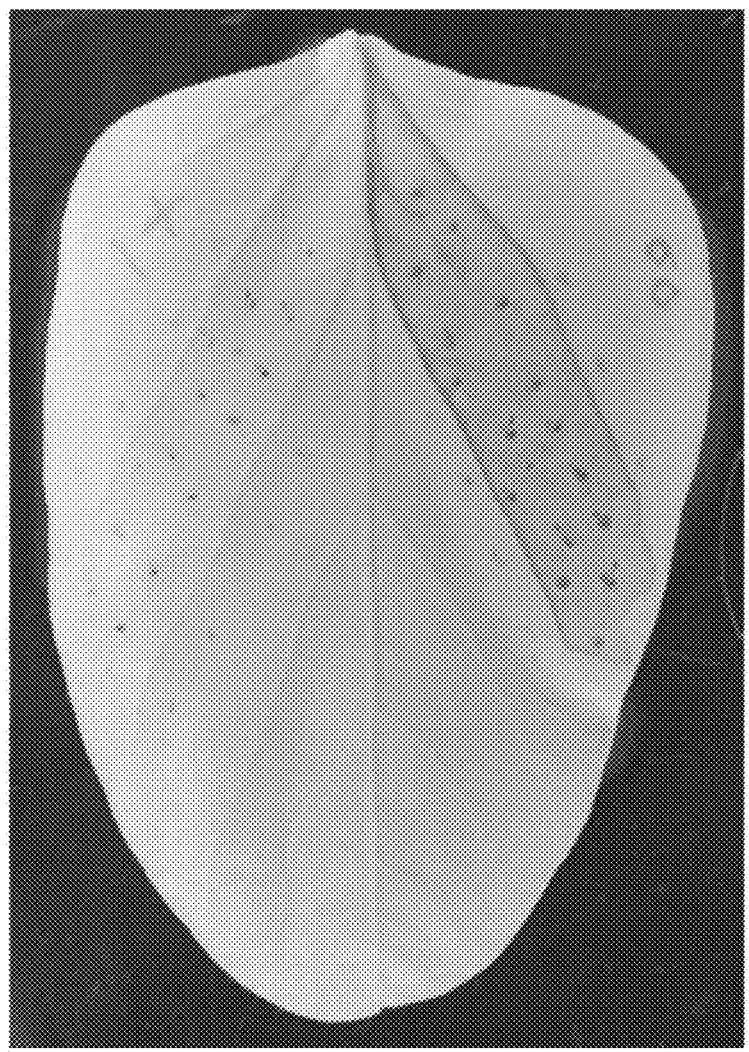

FIG. 17 is a photograph showing AvrPphB recognition by soybean as discussed in Example 6.

While the present disclosure is susceptible to various modifications and alternative forms, exemplary embodiments thereof are shown by way of example in the drawings and are herein described in detail. It should be understood, however, that the description of exemplary embodiments is not intended to limit the disclosure to the particular forms disclosed, but on the contrary, the intention is to cover all modifications, equivalents and alternatives falling within the scope of the disclosure as defined by the embodiments above and the claims below. Reference should therefore be made to the embodiments above and claims below for interpreting the scope of the present disclosure.

DETAILED DESCRIPTION

The compositions, systems and methods now will be described more fully hereinafter with reference to the accompanying drawings, in which some, but not all embodiments of the present disclosure are shown. Indeed, the present disclosure may be embodied in many different forms and should not be construed as limited to the embodiments set forth herein; rather, these embodiments are provided so that this disclosure will satisfy applicable legal requirements.

Likewise, many modifications and other embodiments of the compositions, systems and methods described herein will come to mind to one of skill in the art to which the invention pertains having the benefit of the teachings presented in the foregoing descriptions and the associated drawings. Therefore, it is to be understood that the present disclosure is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present disclosure, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually includes "at least one."

Many plant pathogens employ proteases as virulence factors, including bacteria, fungi and viruses. As used herein, "plant pathogen" or "pathogen" means an organism that interferes with or is harmful to plant development and/or growth. Examples of plant pathogens include, but are not limited to, bacteria (e.g., *Xanthomonas* spp. and *Pseudomonas* spp.), fungi (e.g., members in the phylum Ascomycetes or Basidiomycetes, and fungal-like organisms including Oomycetes such as *Pythium* spp. and *Phytophthora* spp.), insects, nematodes (e.g., soil-transmitted nematodes including *Clonorchis* spp., *Fasciola* spp., *Heterodera* spp., *Globodera* spp., *Opisthorchis* spp. and *Paragonimus* spp.), protozoans (e.g., *Phytomonas* spp.), and viruses (e.g., *Comovirus* spp., *Cucumovirus* spp., *Cytorhab-*

*dovirus* spp., *Luteovirus* spp., *Nepovirus* spp., *Potyvirus* spp., *Tobamovirus* spp., *Tombusvirus* spp. and *Tospovirus* spp.)

Plants, however, contain innate disease resistance against a majority of plant pathogens. Natural variation for resistance to plant pathogens has been identified by plant breeders and pathologists and can be bred into many plants. These natural disease resistance genes provide high levels of resistance (or immunity) to plant pathogens and represent an economical and environmentally friendly form of plant protection.

Innate disease resistance in plants to plant pathogens typically is governed by the presence of dominant or semidominant resistance (R) genes in the plant and dominant avirulence (avr) genes in the pathogen. The largest group of R genes encodes proteins characterized by the presence of a NB-LRR. This form of innate disease resistance typically initiates programmed cell death in infected plant cells/tissues.

*A. thaliana*, for example, uses R genes to confer resistance to *P. syringae* strains that express the avr gene, avrPphB. Specific recognition of AvrPphB requires at least two genes, RPS5 and PBS1. RPS5 encodes a NB-LRR disease resistance protein, and PBS1 encodes a serine/threonine protein kinase.

The work described herein is the first to show that an endogenous *P. syringae* AvrPphB protease recognition sequence within the activation loop of PBS1 (an exposed loop on the surface of the PBS1 protein) can be replaced with a heterologous protease recognition sequence. In particular, it is shown that the endogenous AvrPphB cleavage site (GDKSHVS; SEQ ID NO:1) of PBS1 can be replaced with a heterologous AvrRpt2 cleavage site (VPKFGDW; SEQ ID NO:2) from the *Arabidopsis* RPM1 Interacting Protein 4 (RIN4), thereby producing a modified PBS1 (SEQ ID NO:6) that can be used in connection with RPS5 to confer resistance to pathogens that express AvrRpt2 instead of AvrPphB. It also is shown that the endogenous AvrPphB cleavage site (GDKSHVS; SEQ ID NO:1) of PBS1 can be replaced with a heterologous TEV protease cleavage site (VPKFGDW; SEQ ID NO:4) of a TEV polyprotein, thereby producing another modified PBS1 (SEQ ID NO:8) that can be used in connection with RPS5 to confer resistance to pathogens that express TEV protease instead of AvrPphB. It is further contemplated that that an endogenous *P. syringae* AvrRpt2 cleavage site (VPKFGDW; SEQ ID NO:2) of RIN4 can be replaced with a cleavage site of other pathogen-specific proteases, leading to the activation of its corresponding NB-LRR protein, RPS2, in the presence of such pathogen-specific proteases. It is also contemplated that a Soybean Mosaic Virus cleavage recognition site (SMV NIa protease; EPVSTQG; SEQ ID NO:27) can replace the AvrPphB cleavage site, thereby producing another modified PBS1. It is further contemplated that a Bean Pod Mottle Virus cleavage recognition site (BPMV NIa protease; PVVQAQS; SEQ ID NO:28) can replace the AvrPphB cleavage site, thereby producing another modified PBS1.

The present disclosure therefore provides compositions, systems and methods for conferring additional disease resistance to plant pathogens that express specific proteases in plant cells, plant parts or plants by using a modified substrate of a pathogen-specific protease that has a heterologous protease recognition sequence in connection with its corresponding NB-LRR protein.

Compositions
Recombinant Nucleic and Amino Acid Molecules

Compositions of the present disclosure include recombinant nucleic and amino acid sequences for modified substrate proteins of pathogen-specific proteases in which an endogenous protease recognition sequence within the substrates are replaced with a heterologous protease recognition sequence.

In one aspect, the present disclosure is directed to a recombinant nucleic acid molecule comprising a nucleotide sequence that encodes at least one substrate protein of a plant pathogen-specific protease having a heterologous pathogen-specific protease recognition sequence within the substrate protein. The substrate protein can be, for example, AvrPphB susceptible 1 (PBS1) and Resistance To *Pseudomonas syringae* pv. *maculicola* 1 (RPM1) Interacting Protein 4 (RIN4). Particularly suitable substrate proteins can be, for example, *Arabidopsis thaliana* AvrPphB susceptible 1 (PBS1) and *Arabidopsis thaliana* Resistance To *Pseudomonas syringae* pv. *maculicola* 1 (RPM1) Interacting Protein 4 (RIN4).

As used herein, a "nucleic acid" sequence means a DNA or RNA sequence. The term encompasses sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

As used herein, "recombinant," when used in connection with a nucleic acid molecule, means a molecule that has been created or modified through deliberate human intervention such as by genetic engineering. For example, a recombinant nucleic acid molecule is one having a nucleotide sequence that has been modified to include an artificial nucleotide sequence or to include some other nucleotide sequence that is not present within its native (non-recombinant) form.

Further, a recombinant nucleic acid molecule has a structure that is not identical to that of any naturally occurring nucleic acid molecule or to that of any fragment of a naturally occurring genomic nucleic acid molecule spanning more than one gene. A recombinant nucleic acid molecule also includes, without limitation, (a) a nucleic acid molecule having a sequence of a naturally occurring genomic or extrachromosomal nucleic acid molecule, but which is not flanked by the coding sequences that flank the sequence in its natural position; (b) a nucleic acid molecule incorporated into a construct, expression cassette or vector, or into a host cell's genome such that the resulting polynucleotide is not identical to any naturally occurring vector or genomic DNA; (c) a separate nucleic acid molecule such as a cDNA, a genomic fragment, a fragment produced by polymerase chain reaction (PCR) or a restriction fragment; and (d) a recombinant nucleic acid molecule having a nucleotide sequence that is part of a hybrid gene (i.e., a gene encoding a fusion protein). As such, a recombinant nucleic acid molecule can be modified (chemically or enzymatically) or unmodified DNA or RNA, whether fully or partially single-stranded or double-stranded or even triple-stranded.

A nucleic acid molecule (or its complement) that can hybridize to any of the uninterrupted nucleotide sequences described herein, under either highly stringent or moderately stringent hybridization conditions, also is within the scope of the present disclosure.

As used herein, "stringent conditions" means conditions under which one nucleic acid molecule will hybridize to its target to a detectably greater degree than to other sequences (e.g., at least two-fold over background). Stringent conditions can be sequence-dependent and will be different in different circumstances. By controlling the stringency of the hybridization and/or washing conditions, target sequences that are 100% complementary to the nucleic acid molecule can be identified (i.e., homologous probing). Alternatively, the stringent condition can be adjusted to allow some mismatching in sequences so that lower degrees of similarity are detected (i.e., heterologous probing).

Typically, stringent conditions can be one in which the salt concentration is less than about 1.5 M $Na^+$, typically about 0.01 M to 1.0 M $Na^+$ (or other salts) at about pH 7.0 to 8.3, and a temperature of at least about 30° C. for short molecules (e.g., 10 to 50 nucleotides) and of at least about 60° C. for long molecules (e.g., greater than 50 nucleotides). Stringent conditions also can be achieved by adding destabilizing agents such as formamide.

As used herein, "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

An exemplary low stringent condition includes hybridizing with a buffer solution of about 30% to about 35% formamide, 1 M NaCl, 1% SDS (sodium dodecyl sulphate) at about 37° C., and washing in about 1× to 2×SSC (20× SSC=3.0 M NaCl/0.3 M trisodium citrate) at about 50° C. to about 55° C. Wash buffers optionally can comprise about 0.1% to about 1% SDS.

An exemplary moderate stringent condition includes hybridizing in about 40% to about 45% formamide, 1.0 M NaCl, 1% SDS at about 37° C., and washing in about 0.5× to 1×SSC at about 55° C. to about 60° C. Wash buffers optionally can comprise about 0.1% to about 1% SDS.

An exemplary high stringent condition includes hybridizing in about 50% formamide, 1 M NaCl, 1% SDS at about 37° C., and washing in about 0.1×SSC at about 60° C. to about 65° C. Wash buffers optionally can comprise about 0.1% to about 1% SDS.

The duration of hybridizing generally can be less than about 24 hours, usually about 4 hours to about 12 hours. The duration of the washing can be at least a length of time sufficient to reach equilibrium. Additional guidance regarding such conditions is readily available in the art, for example, in *Molecular Cloning: A Laboratory Manual*, 3rd ed. (Sambrook & Russell eds., Cold Spring Harbor Press 2001); and *Current Protocols in Molecular Biology* (Ausubel et al. eds., John Wiley & Sons 1995).

The heterologous pathogen-specific protease recognition sequence can be from about 5 amino acids to about 15 amino acids. A list of plant pathogen-specific proteases, plant pathogens of origin, protease substrate proteins and the endogenous protease recognition sequences are listed in Table 1, which can be used as a source for heterologous protease recognition sequences.

TABLE 1

Plant Pathogen-Specific Proteases, Plant Pathogen of Origin, Protease Substrate Proteins and Endogenous Protease Recognition Sequence.

| Plant Pathogen-Specific Protease | Plant Pathogen of Origin | Protease Substrate Protein and Protease Recognition Sequence (amino acid sequence) |
|---|---|---|
| AvrPphB | P. syringae | PBS1; GDKSHVS (SEQ ID NO: 1) |
| AvrRpt2 | P. syringae | RIN4; VPKFGDW (SEQ ID NO: 2) |
| HopN1 | P. syringae | PsbQ; QEHGCQL (SEQ ID NO: 3) |
| TEV protease | Tobacco Etch Virus | TEV polyprotein; ENLYFQG (SEQ ID NO: 4) |
| SMV NIa protease | Soybean Mosaic Virus | SMV polyprotein; EPVSTQG (SEQ ID NO: 27) |
| BPMV NIa protease | Bean Pod Mottle Virus | BPMV polyprotein; PVVQAQS (SEQ ID NO: 28) |

Additional avirulence and disease resistance pairs can be found in, for example, Jones et al. (1994) *Science* 266:789-793; Martin et al. (1993) *Science* 262:1432-1436; and Mindrinos et al. (1994) *Cell* 78:1089-1099).

The examples below relate to the RPS5 substrate protein and PBS1 NB-LRR protein pair of *A. thaliana*. Nucleic and amino acids sequences for RPS5 are known and characterized. See, e.g., GenBank® Accession Nos. NM_001198041.1, NM_101094.2 and 064973.2. See also, Warren et al. (1998) *Plant Cell* 10:1439-1452; and DeYoung et al. (2012) *Cell. Microbiol.* 14:1071-1084. Likewise, nucleic and amino acids sequences for PBS1 are known and characterized, see, e.g., GenBank® Accession Nos.

NM_121319.4, NM_115403.3, AF314176.1, NP_196820 and AAG38109.1. See also, Swiderski & Innes (2001) *Plant J.* 26:101-112; and DeYoung et al. (2012), supra, as well as U.S. Pat. No. 5,648,599. The pathogen-specific protease natively related to this pair is AvrPphB (GenBank® Accession No. CAI36057.1).

Other examples relate to the RIN4 substrate protein and RPS2 NB-LRR protein pair of *A. thaliana*. Nucleic and amino acid sequences for RIN4 and RPS2 are known and characterized. See, e.g., GenBank® Accession Nos. Q8GYN5.1 and AAA21874.1. The pathogen-specific protease natively related to this pair is AvrRpt2 (GenBank® Accession No. Q6LAD6.1).

An example of a recombinant nucleic acid molecule encoding a modified substrate protein of a pathogen-specific protease therefore includes a nucleotide sequence that encodes PBS1 in which its endogenous AvrPphB cleavage site (SEQ ID NO:1) is replaced with a heterologous AvrRpt2 cleavage site (SEQ ID NO:2), as is shown in SEQ ID NO:5. Another example of a recombinant nucleic acid molecule encoding a modified substrate protein of a pathogen-specific protease includes a nucleotide sequence that encodes PBS1 in which its endogenous AvrPphB cleavage site (SEQ ID NO:1) is replaced with a heterologous TEV protease cleavage site (SEQ ID NO:4), as is shown in SEQ ID NO:7. Another example of a recombinant nucleic acid molecule encoding a modified substrate protein of a pathogen-specific protease includes a nucleotide sequence that encodes PBS1 in which its endogenous AvrPphB cleavage site (SEQ ID NO:1) is replaced with a heterologous HopN1 cleavage site (SEQ ID NO:3). Another example of a recombinant nucleic acid molecule encoding a modified substrate protein of a pathogen-specific protease includes a nucleotide sequence that encodes RIN4 in which its endogenous AvrRpt2 cleavage site (SEQ ID NO:2) is replaced with a heterologous AvrPphB cleavage site (SEQ ID NO:1). Another example of a recombinant nucleic acid molecule encoding a modified substrate protein of a pathogen-specific protease includes a nucleotide sequence that encodes RIN4 in which its endogenous AvrRpt2 cleavage site (SEQ ID NO:2) is replaced with a heterologous TEV protease cleavage site (SEQ ID NO:4). Another example of a recombinant nucleic acid molecule encoding a modified substrate protein of a pathogen-specific protease includes a nucleotide sequence that encodes RIN4 in which its endogenous AvrRpt2 cleavage site (SEQ ID NO:2) is replaced with a heterologous HopN1 cleavage site (SEQ ID NO:3). Another example of a recombinant nucleic acid molecule encoding a modified substrate protein of a pathogen-specific protease includes a nucleotide sequence that encodes PBS1 in which its endogenous AvrPphB cleavage site (SEQ ID NO:1) is replaced with a heterologous SMV cleavage site (SEQ ID NO:27). Another example of a recombinant nucleic acid molecule encoding a modified substrate protein of a pathogen-specific protease includes a nucleotide sequence that encodes PBS1 in which its endogenous AvrPphB cleavage site (SEQ ID NO:1) is replaced with a heterologous BPMV cleavage site (SEQ ID NO:28). Another example of a recombinant nucleic acid molecule encoding a modified substrate protein of a pathogen-specific protease includes a nucleotide sequence that encodes RIN4 in which its endogenous AvrRpt2 cleavage site (SEQ ID NO:2) is replaced with a heterologous SMV cleavage site (SEQ ID NO:27). Another example of a recombinant nucleic acid molecule encoding a modified substrate protein of a pathogen-specific protease includes a nucleotide sequence that encodes RIN4 in which its endogenous AvrRpt2 cleavage site (SEQ ID NO:2) is replaced with a heterologous BPMV cleavage site (SEQ ID NO:28). The endogenous protease cleavage sequence, which is a preferred location for the heterologous protease recognition sequence, can be located in an exposed loop of the substrate protein, for example. In one particularly suitable embodiment of the substrate protein, the endogenous protease cleavage sequence can be located, for example, between about amino acid position 240 to about amino acid position 250 when the substrate protein is PBS1. In another particularly suitable embodiment of the substrate protein, the endogenous protease cleavage sequence can be located, for example, between about amino acid position 142 to about amino acid position 165 when the substrate protein is RIN4.

Methods for synthesizing nucleic acid molecules are well known in the art, such as cloning and digestion of the appropriate sequences, as well as direct chemical synthesis (e.g., ink-jet deposition and electrochemical synthesis). Methods of cloning nucleic acid molecules are described, for example, in Ausubel et al. (1995), supra; Copeland et al. (2001) *Nat. Rev. Genet.* 2:769-779; *PCR Cloning Protocols*, 2nd ed. (Chen & Janes eds., Humana Press 2002); and Sambrook & Russell (2001), supra. Methods of direct chemical synthesis of nucleic acid molecules include, but are not limited to, the phosphotriester methods of Reese (1978) *Tetrahedron* 34:3143-3179 and Narang et al. (1979) *Methods Enzymol.* 68:90-98; the phosphodiester method of Brown et al. (1979) *Methods Enzymol.* 68:109-151; the diethylphosphoramidate method of Beaucage et al. (1981) *Tetrahedron Lett.* 22:1859-1862; and the solid support methods of Fodor et al. (1991) *Science* 251:767-773; Pease et al. (1994) *Proc. Natl. Acad. Sci. USA* 91:5022-5026; and Singh-Gasson et al. (1999) *Nature Biotechnol.* 17:974-978; as well as U.S. Pat. No. 4,485,066. See also, Peattie (1979) *Proc. Natl. Acad. Sci. USA* 76:1760-1764; as well as EP Patent No. 1 721 908; Int'l Patent Application Publication Nos. WO 2004/022770 and WO 2005/082923; US Patent Application Publication No. 2009/0062521; and U.S. Pat. Nos. 6,521,427; 6,818,395 and 7,521,178.

In addition to the full-length nucleotide sequence of a nucleic acid molecule encoding a modified substrate protein, it is intended that the nucleic acid molecule can be a fragment or variant thereof that is capable of functioning as a substrate. For nucleotide sequences, "fragment" means a portion of a nucleotide sequence of a nucleic acid molecule, for example, a portion of the nucleotide sequence encoding a modified substrate protein. Fragments of a nucleotide sequence may retain the biological activity of the reference nucleic acid molecule. For example, less than the entire sequence disclosed in SEQ ID NO:5 or 7 can be used and will encode a modified substrate protein that interacts with a pathogen-specific protease and that retains its ability to interact with its corresponding NB-LRR protein. Likewise, a fragment of a nucleotide sequence encoding the modified substrate protein can be used if that fragment encodes a modified substrate protein that interacts with a pathogen-specific protease and that retains its ability to interact with its corresponding NB-LRR protein. Alternatively, fragments of a nucleotide sequence that can be used as hybridization probes generally do not need to retain biological activity. Thus, fragments of the nucleic acid molecules can be at least about 10, 15, 20, 25, 50, 75, 100, 125, 150, 175, 200, 250, 300, 350, 400, 450, 500, 550, 600, 650, 700, 750, 800, 850 or 900 nucleotides, or up to the number of nucleotides present in a full-length nucleic acid molecule.

A fragment of the nucleic acid molecule therefore can include a functionally/biologically active portion, or it can include a fragment that can be used as a hybridization probe or PCR primer. A biologically active portion of the nucleic acid molecule can be prepared by isolating part of the sequence of the nucleic acid molecule, operably linking that fragment to a promoter, expressing the nucleotide sequence encoding the protein, and assessing the amount or activity of the protein. Methods of assaying protein expression are well known in the art. See, e.g., Chan et al. (1994) *J. Biol. Chem.* 269:17635-17641; Freyssinet & Thomas (1998) *Pure & Appl. Chem.* 70:61-66; and Kirby et al. (2007) *Adv. Clin. Chem.* 44:247-292; as well as US Patent Application Publication Nos. 2009/0183286 and 2009/0217424; and U.S. Pat. Nos. 7,294,711 and 7,408,055. Likewise, kits for assaying protein expression are commercially available, for example, from Applied Biosystems, Inc. (Foster City, Calif.), Caliper Life Sciences (Hopkinton, Mass.), Promega (Madison, Wis.), and SABiosciences (Frederick, Md.). Protein expression also can be assayed using other methods well known in the art, including, but not limited to, Western blot analysis, enzyme-linked immunosorbent assay, and the like. See, e.g., Sambrook & Russel (2001), supra. Moreover, methods of assaying pathogen-specific protease substrate protein activity are well known in the art. See, DeYoung et al. (2012), supra.

For nucleotide sequences, "variant" means a substantially similar nucleotide sequence to a nucleotide sequence of a recombinant nucleic acid molecule as described herein, for example, a substantially similar nucleotide sequence encoding a modified substrate protein. For nucleotide sequences, a variant comprises a nucleotide sequence having deletions (i.e., truncations) at the 5' and/or 3' end, deletions and/or additions of one or more nucleotides at one or more internal sites compared to the nucleotide sequence of the recombinant nucleic acid molecules as described herein; and/or substitution of one or more nucleotides at one or more sites compared to the nucleotide sequence of the recombinant nucleic acid molecules described herein. One of skill in the art understands that variants are constructed in a manner to maintain the open reading frame.

Conservative variants include those nucleotide sequences that, because of the degeneracy of the genetic code (see, Table 2), result in a functionally active modified substrate protein as described herein. Naturally occurring allelic variants can be identified by using well-known molecular biology techniques such as, for example, polymerase chain reaction (PCR) and hybridization techniques. Variant nucleotide sequences also can include synthetically derived sequences, such as those generated, for example, by site-directed mutagenesis but which still provide a functionally active modified substrate protein. Generally, variants of a nucleotide sequence of the recombinant nucleic acid molecules as described herein will have at least about 70%, 75%, 80%, 85%, 90%, 91%, 92%, 93%, 94%, 95%, 96%, 97%, 98%, 99% or more sequence identity to the nucleotide sequence of the recombinant nucleic acid molecules as determined by sequence alignment programs and parameters as described elsewhere herein.

When making recombinant nucleic acid molecules as described herein and variants thereof, one of skill in the art can be further guided by knowledge of redundancy in the genetic code as shown below in Table 2.

TABLE 2

Redundancy in Genetic Code.

| Residue | Triplet Codons Encoding the Residue |
| --- | --- |
| Ala (A) | GCU, GCC, GCA, GCG |
| Arg (R) | CGU, CGC, CGA, CGG, AGA, AGG |

TABLE 2-continued

Redundancy in Genetic Code.

| Residue | Triplet Codons Encoding the Residue |
| --- | --- |
| Asn (N) | AAU, AAC |
| Asp (D) | GAU, GAC |
| Cys (C) | UGU, UGC |
| Gln (Q) | CAA, CAG |
| Glu (E) | GAA, GAG |
| Gly (G) | GGU, GGC, GGA, GGG |
| His (H) | CAU, CAC |
| Ile (I) | AUU, AUC, AUA |
| Leu (L) | UUA, UUG, CUU, CUC, CUA, CUG |
| Lys (K) | AAA, AAG |
| Met (M) | AUG |
| Phe (F) | UUU, UUC |
| Pro (P) | CCU, CCC, CCA, CCG |
| Ser (S) | UCU, UCC, UCA, UCG, AGU, AGC |
| Thr (T) | ACU, ACC, ACA, ACG |
| Trp (W) | UGG |
| Tyr (Y) | UAU, UAC |
| Val (V) | GUU, GUC, GUA, GUG |
| START | AUG |
| STOP | UAG, UGA, UAA |

Deletions, insertions and/or substitutions of the nucleotide sequence of the recombinant nucleic acid molecules are not expected to produce radical changes in their characteristics. However, when it is difficult to predict the exact effect of the substitution, deletion or insertion in advance of doing so, one of skill in the art will appreciate that the effect can be evaluated by expression assays.

Variant nucleic acid molecules also encompass nucleotide sequences derived from a mutagenic and recombinogenic procedure such as DNA shuffling. With such a procedure, the nucleotide sequences of the recombinant nucleic acid molecules described herein can be manipulated to create a new nucleic acid molecule possessing the desired properties. In this manner, libraries of recombinant nucleic acid molecules can be generated from a population of related nucleic acid molecules comprising sequence regions that have substantial sequence identity and can be homologously recombined in vitro or in vivo. For example, using this approach, sequence motifs encoding a domain of interest can be shuffled between the nucleic acid molecules described herein and other known promoters to obtain a new nucleic acid molecule with an improved property such as increased promoter activity.

Methods of mutating and altering nucleotide sequences, as well as DNA shuffling, are well known in the art. See, Crameri et al. (1997) *Nature Biotech.* 15:436-438; Crameri et al. (1998) *Nature* 391:288-291; Kunkel (1985) *Proc. Natl. Acad. Sci. USA* 82:488-492; Kunkel et al. (1987) *Methods in Enzymol.* 154:367-382; Moore et al. (1997) *J. Mol. Biol.* 272:336-347; Stemmer (1994) *Proc. Natl. Acad. Sci. USA* 91:10747-10751; Stemmer (1994) *Nature* 370:389-391; Zhang et al. (1997) *Proc. Natl. Acad. Sci. USA* 94:4504-4509; and *Techniques in Molecular Biology* (Walker & Gaastra eds., MacMillan Publishing Co. 1983) and the references cited therein; as well as U.S. Pat. Nos. 4,873,192; 5,605,793 and 5,837,458. As such, the nucleic acid molecules as described herein can have many modifications.

Variants of the recombinant nucleic acid molecules described herein also can be evaluated by comparing the percent sequence identity between the polypeptide encoded by a variant and the polypeptide encoded by a reference nucleic acid molecule. Thus, for example, an isolated nucleic acid molecule can be one that encodes a polypeptide with a given percent sequence identity to the polypeptide of interest. Percent sequence identity between any two polypeptides can be calculated using sequence alignment programs and parameters described elsewhere herein. Where any given pair of polynucleotides of the present disclosure is evaluated by comparison of the percent sequence identity shared by the two polypeptides they encode, the percent sequence identity between the two encoded polypeptides can be at least about 70%, 75%, 80%, 85%, 90%, 91%, 92%, 93%, 94%, 95%, 96%, 97%, 98%, 99% or more sequence identity.

Determining percent sequence identity between any two sequences can be accomplished using a mathematical algorithm. Non-limiting examples of such mathematical algorithms include, but are not limited to, the algorithm of Myers & Miller (1988) *CABIOS* 4:11-17; the local alignment algorithm of Smith et al. (1981) *Adv. Appl. Math.* 2:482-489; the global alignment algorithm of Needleman & Wunsch (1970) *J. Mol. Biol.* 48:443-453; the search-for-local alignment method of Pearson & Lipman (1988) *Proc. Natl. Acad. Sci. USA* 85:2444-2448; the algorithm of Karlin & Altschul (1990) *Proc. Natl. Acad. Sci. USA* 87:2264-2268, modified as in Karlin & Altschul (1993) *Proc. Natl. Acad. Sci. USA* 90:5873-5877.

The present disclosure therefore includes recombinant nucleic acid molecules having a nucleotide sequence that encodes a modified substrate protein of a pathogen-specific protease, where the modified substrate protein has a heterologous protease recognition sequence and can be incorporated into nucleic acid constructs such as expression cassettes and vectors.

Nucleic Acid Constructs

Compositions of the present disclosure also include nucleic acid constructs, such as expression cassettes or vectors, having plant promoters operably linked with a nucleic acid molecule that encodes a substrate protein of a pathogen-specific protease with a heterologous pathogen-specific protease recognition sequence for use in transforming plant cells, plant parts and plants. In addition, the constructs can include a nucleic acid molecule that encodes a NB-LRR protein, particularly when such NB-LRR protein is not native/not endogenous to the plant cell, plant part or plant to be transformed.

As used herein, "nucleic acid construct" means an oligonucleotide or polynucleotide composed of deoxyribonucleotides, ribonucleotides or combinations thereof having incorporated therein the nucleotide sequences described herein. The nucleotide construct can be used for transforming organisms such as plants. In this manner, plant promoters operably linked to a nucleotide sequence for a modified substrate protein of a pathogen-specific protease as described herein are provided in nucleic acid constructs for expression in a plant cell, plant part or plant.

As used herein, "expression cassette" means a nucleic acid molecule having at least a control sequence operably linked to a coding sequence.

As used herein, "operably linked" means that the elements of the expression cassette are configured so as to perform their usual function. Thus, control sequences (i.e., promoters) operably linked to a coding sequence are capable of effecting expression of the coding sequence. The control sequences need not be contiguous with the coding sequence, so long as they function to direct the expression thereof. Thus, for example, intervening untranslated, yet transcribed, sequences can be present between a promoter and a coding sequence, and the promoter sequence still can be considered "operably linked" to the coding sequence.

As used herein, a "coding sequence" or "coding sequences" means a sequence that encodes a particular polypeptide, and is a nucleotide sequence that is transcribed (in the case of DNA) and translated (in the case of mRNA) into a polypeptide in vitro or in vivo when placed under the control of appropriate regulatory sequences. The boundaries of the coding sequence are determined by a start codon at a 5' (amino) terminus and a translation stop codon at a 3' (carboxy) terminus. A coding sequence can include, but is not limited to, viral nucleic acid sequences, cDNA from prokaryotic or eukaryotic mRNA, genomic DNA sequences from prokaryotic or eukaryotic DNA, and even synthetic DNA sequences. A transcription termination sequence will usually be located 3' to the coding sequence. Examples of coding sequences for use herein include nucleotide sequence that encodes a modified substrate protein of a pathogen-specific protease, a NB-LRR protein or both.

As used herein, "control sequence" or "control sequences" means promoters, polyadenylation signals, transcription and translation termination sequences, upstream regulatory domains, origins of replication, internal ribosome entry sites ("IRES"), enhancers, and the like, which collectively provide for replication, transcription and translation of a coding sequence in a recipient host cell. Not all of these control sequences need always be present so long as the selected coding sequence is capable of being replicated, transcribed and translated in an appropriate host cell.

As used herein, a "promoter" means a nucleotide region comprising a nucleic acid (i.e., DNA) regulatory sequence, wherein the regulatory sequence is derived from a gene or synthetically created that is capable of binding RNA polymerase and initiating transcription of a downstream (3'-direction) coding sequence. A number of promoters can be used in the expression cassette, including the native promoter of the modified substrate protein or NB-LRR protein.

Alternatively, promoters can be selected based upon a desired outcome. Such promoters include, but are not limited to, "constitutive promoters" (where expression of a polynucleotide sequence operably linked to the promoter is unregulated and therefore continuous), "inducible promoters" (where expression of a polynucleotide sequence operably linked to the promoter is induced by an analyte, cofactor, regulatory protein, etc.), and "repressible promoters" (where expression of a polynucleotide sequence operably linked to the promoter is repressed by an analyte, cofactor, regulatory protein, etc.).

As used herein, "plant promoter" means a promoter that drives expression in a plant such as a constitutive, inducible (e.g., chemical-, environmental-, pathogen- or wound-inducible), repressible, tissue-preferred or other promoter for use in plants.

Examples of constitutive promoters include, but are not limited to, the rice actin 1 promoter (Wang et al. (1992) *Mol. Cell. Biol.* 12:3399-3406; and U.S. Pat. No. 5,641,876), the CaMV 19S promoter (Lawton et al. (1987) *Plant Mol. Biol.* 9:315-324), the CaMV 35S promoter (Odell et al. (1985) *Nature* 313:810-812), the nos promoter (Ebert et al. (1987) *Proc. Natl. Acad. Sci. USA* 84:5754-5749), the Adh promoter (Walker et al. (1987) *Proc. Natl. Acad. Sci. USA* 84:6624-6628), the sucrose synthase promoter (Yang & Russell (1990) *Proc. Natl. Acad. Sci. USA* 87:4144-4148), the ubiquitin promoters, and the like. See also, U.S. Pat. Nos. 5,608,149; 5,608,144; 5,604,121; 5,569,597; 5,466,785; 5,399,680; 5,268,463; 5,608,142 and 6,177,611.

Examples of chemical-inducible promoters include, but are not limited to, the maize Tn2-2 promoter, which is activated by benzenesulfonamide herbicide safeners; the maize GST promoter, which is activated by hydrophobic electrophilic compounds that are used as pre-emergent herbicides; and the tobacco PR-1a promoter, which is activated by salicylic acid. Other chemical-inducible promoters of interest include steroid-responsive promoters (e.g., the glucocorticoid-inducible promoters in Aoyama & Chua (1997) *Plant J.* 11:605-612; McNellis et al. (1998) *Plant J.* 14:247-257; and Schena et al. (1991) *Proc. Natl. Acad. Sci. USA* 88:10421-10425); tetracycline-inducible and tetracycline-repressible promoters (Gatz et al. (1991) *Mol. Gen. Genet.* 227:229-237; as well as U.S. Pat. Nos. 5,814,618 and 5,789,156); ABA- and turgor-inducible promoters, the auxin-binding protein gene promoter (Schwob et al. (1993) *Plant J.* 4:423-432), the UDP glucose flavonoid glycosyltransferase gene promoter (Ralston et al. (1988) *Genetics* 119:185-187), the MPI proteinase inhibitor promoter (Cordero et al. (1994) *Plant J.* 6:141-150), and the glyceraldehyde-3-phosphate dehydrogenase gene promoter (Kohler et al. (1995) *Plant Mol. Biol.* 29:1293-1298; Martinez et al. (1989) *J. Mol. Biol.* 208:551-565; and Quigley et al. (1989) *J. Mol. Evol.* 29:412-421). Also included are the benzene sulphonamide-inducible (U.S. Pat. No. 5,364,780) and alcohol-inducible (Int'l Patent Application Publication Nos. WO 97/06269 and WO 97/06268) systems and glutathione S-transferase promoters. Chemical-inducible promoters therefore can be used to modulate the expression of a nucleotide sequence of interest in a plant by applying an exogenous chemical regulator. Depending upon the objective, the promoter can be a chemical-inducible promoter, whereby application of the chemical induces gene expression, or a chemical-repressible promoter, whereby application of the chemical represses gene expression. See also, Gatz (1997) *Annu. Rev. Plant Physiol. Plant Mol. Biol.* 48:89.

Other inducible promoters include promoters from genes inducibly regulated in response to environmental stress or stimuli such as drought, pathogens, salinity and wounds. See, Graham et al. (1985) *J. Biol. Chem.* 260:6555-6560; Graham et al. (1985) *J. Biol. Chem.* 260:6561-6564; and Smith et al. (1986) *Planta* 168:94-100. Wound-inducible promoters include the metallocarboxypeptidase-inhibitor protein promoter (Graham et al. (1981) *Biochem. Biophys. Res. Comm.* 101:1164-1170).

Examples of tissue-preferred promoters include, but are not limited to, the rbcS promoter, the ocs, nos and mas promoters that have higher activity in roots or wounded leaf tissue, a truncated (−90 to +8) 35S promoter that directs enhanced expression in roots, an α-tubulin gene promoter that directs expression in roots, as well as promoters derived from zein storage protein genes that direct expression in endosperm. Additional examples of tissue-preferred promoters include, but are not limited to, the promoters of genes encoding the seed storage proteins (e.g., β-conglycinin, cruciferin, napin and phaseolin), zein or oil body proteins (e.g., oleosin), or promoters of genes involved in fatty acid biosynthesis (e.g., acyl carrier protein, stearoyl-ACP desaturase and fatty acid desaturases (e.g., fad 2-1)), and promoters of other genes expressed during embryo development (e.g., Bce4; Kridl et al. (1991) *Seed Sci. Res.* 1:209-219). Further examples of tissue-specific promoters include, but are not limited to, the lectin promoter (Lindstrom et al. (1990) *Dev. Genet.* 11:160-167; and Vodkin (1983) *Prog. Clin. Biol. Res.* 138:87-98), the corn alcohol dehydrogenase 1 promoter (Dennis et al. (1984) *Nucleic Acids Res.* 12:3983-4000; and Vogel et al. (1989) *J. Cell. Biochem.* 13:Part D, M350 (Abstract)), corn light harvesting complex (Bansal et al. (1992) *Proc. Natl. Acad. Sci. USA* 89:3654-3658; and Simpson (1986) *Science* 233:34-380), corn heat shock protein (Odell et al. (1985) *Nature* 313:810-812; and Rochester et al. (1986) *EMBO J.* 5:451-458), the pea small subunit RuBP carboxylase promoter (Cashmore, "Nuclear genes encoding the small subunit of ribulose-1,5-bisphosphate carboxylase" 29-38 In: Gen. Eng. of Plants (Plenum Press 1983); and Poulsen et al. (1986) *Mol. Gen. Genet.* 205:193-200), the Ti plasmid mannopine synthase promoter (Langridge et al. (1989) *Proc. Natl. Acad. Sci. USA* 86:3219-3223), the Ti plasmid nopaline synthase promoter (Langridge et al. (1989), supra), the *petunia* chalcone isomerase promoter (van Tunen et al. (1988) *EMBO J.* 7:1257-1263), the bean glycine rich protein 1 promoter (Keller et al. (1989) *Genes Dev.* 3:1639-1646), the truncated CaMV 35s promoter (Odell et al. (1985), supra), the potato patatin promoter (Wenzler et al. (1989) *Plant Mol. Biol.* 13:347-354), the root cell promoter (Yamamoto et al. (1990) *Nucleic Acids Res.* 18:7449), the maize zein promoter (Langridge et al. (1983) *Cell* 34:1015-1022; Kriz et al. (1987) *Mol. Gen. Genet.* 207:90-98; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), the globulin-1 gene (Belanger et al. (1991) *Genetics* 129:863-872), the α-tubulin, cab promoter (Sullivan et al. (1989) *Mol. Gen. Genet.* 215:431-440), the PEPCase promoter (Hudspeth & Grula (1989) *Plant Mol. Biol.* 12:579-589), the R gene complex-associated promoters (Chandler et al. (1989) *Plant Cell* 1:1175-1183), and the chalcone synthase promoters (Franken et al. (1991) *EMBO J.* 10:2605-2612). See also, Canevascini et al. (1996) *Plant Physiol.* 112:513-524; Guevara-Garcia et al. (1993) *Plant J.* 4:495-505; Hansen et al. (1997) *Mol. Gen. Genet.* 254:337-343; Kawamata et al. (1997) *Plant Cell Physiol.* 38:792-803; Lam (1994) *Results Probl. Cell Differ.* 20:181-196; Matsuoka et al. (1993) *Proc. Natl. Acad. Sci. USA* 90:9586-9590; Orozco et al. (1993) *Plant Mol. Biol.* 23:1129-1138; Rinehart et al. (1996) *Plant Physiol.* 112:1331-1341; Russell et al. (1997) *Transgenic Res.* 6:157-168; Van Camp et al. (1996) *Plant Physiol.* 112:525-535; Yamamoto et al. (1994) *Plant Cell Physiol.* 35:773-778; and Yamamoto et al. (1997) *Plant J.* 12:255-265.

In some instances, the tissue-preferred promoter can be a leaf-preferred promoter. See, Gan et al. (1995) *Science* 270:1986-1988; Gotor et al. (1993) *Plant J.* 3:509-518; Kwon et al. (1994) *Plant Physiol.* 105:357-367; Matsuoka et al. (1993), supra; Orozco et al. (1993), supra; Yamamoto et al. (1994), supra; and Yamamoto et al. (1997), supra.

In some instances, the tissue-preferred promoter can be a root-preferred promoter. See, Capana et al. (1994) *Plant Mol. Biol.* 25:681-691 (rolB promoter); Hire et al. (1992) *Plant Mol. Biol.* 20:207-218 (soybean root-specific glutamine synthetase gene); Keller & Baumgartner (1991) *Plant Cell* 3:1051-1061 (root-specific control element in the GRP 1.8 gene of French bean); Kuster et al. (1995) *Plant Mol. Biol.* 29:759-772 (VfENOD-GRP3 gene promoter) Miao et al. (1991) *Plant Cell* 3:11-22 (full-length cDNA clone encoding cytosolic glutamine synthetase (GS), which is expressed in roots and root nodules of soybean); and Sanger et al. (1990) *Plant Mol. Biol.* 14:433-443 (root-specific promoter of the mannopine synthase (MAS) gene of *A. tumefaciens*); see also, U.S. Pat. Nos. 5,837,876; 5,750,386; 5,633,363; 5,459,252; 5,401,836; 5,110,732; and 5,023,179. Likewise, Bogusz et al. (1990) *Plant Cell* 2:633-641 describes two root-specific promoters isolated from hemoglobin genes from the nitrogen-fixing nonlegume *Parasponia andersonii* and the related non-nitrogen-fixing nonlegume *Trema tomentosa*. Leach & Aoyagi (1991) *Plant Sci.*

79:69-76 describes an analysis of the promoters of the highly expressed rolC and rolD root-inducing genes of *Agrobacterium rhizogenes*. Teeri et al. (1989) *EMBO J.* 8:343-335 describes a gene fusion to lacZ to show that the *Agrobacterium* T-DNA gene encoding octopine synthase is especially active in the epidermis of the root tip and that the TR2' gene is root specific in the intact plant and stimulated by wounding in leaf tissue.

In some instances, the tissue-preferred promoter can be a seed-preferred promoter, which includes both "seed-specific" promoters (i.e., promoters active during seed development such as promoters of seed storage proteins) and "seed-germinating" promoters (i.e., promoters active during seed germination). See, Thompson et al. (1989) *BioEssays* 10:108-113. Examples of seed-preferred promoters include, but are not limited to, the Cim1 promoter (cytokinin-induced message); the cZ19B1 promoter (maize 19 kDa zein); the myo-inositol-1-phosphate synthase (milps) promoter (Int'l Patent Application Publication No. WO 00/11177; and U.S. Pat. No. 6,225,529); the γ-zein promoter; and the globulin 1 (Glb-1) promoter. For monocots, seed-specific promoters include, but are not limited to, promoters from maize 15 kDa zein, 22 kDa zein, 27 kDa zein, γ-zein, waxy, shrunken 1, shrunken 2 and Glb-1. See also, Int'l Patent Application Publication No. WO 00/12733, which discloses seed-preferred promoters from end1 and end2 genes. For dicots, seed-specific promoters include, but are not limited to, promoters from bean β-phaseolin, napin, β-conglycinin, soybean lectin, cruciferin and pea vicilin (Czako et al. (1992) *Mol. Gen. Genet.* 235:33-40). See also, U.S. Pat. No. 5,625,136.

In some instances, the tissue-preferred promoter can be a stalk-preferred promoter. Examples of stalk-preferred promoters include, but are not limited to, the maize MS8-15 gene promoter (Int'l Patent Application Publication No. WO 98/00533; and U.S. Pat. No. 5,986,174), and the promoters disclosed in Graham et al. (1997) *Plant Mol. Biol.* 33:729-735.

In some instances, the tissue-preferred promoter can be a vascular tissue-preferred promoter. For example, a vascular tissue-preferred promoter can be used to express the modified substrate protein in polypexylem and phloem tissue. Examples of vascular tissue-preferred promoters include, but are not limited to, the *Prunus serotina* prunasin hydrolase gene promoter (Int'l Patent Application Publication No. WO 03/006651), and the promoters disclosed in U.S. Pat. No. 6,921,815.

As an alternative to the promoters listed above, in some instances a low level of expression is desired and can be achieved by using a weak promoter. As used herein, "weak promoter" means a promoter that drives expression of a coding sequence at a low level. As used herein, "low level" means at levels of about 1/1000 transcripts to about 1/100,000 transcripts to about 1/500,000 transcripts. Alternatively, it is recognized that weak promoter also encompasses promoters that are expressed in only a few cells and not in others to give a total low level of expression. Where a promoter is expressed at unacceptably high levels, portions of the promoter sequence can be deleted or modified to decrease expression levels.

Examples of weak constitutive promoters include, but are not limited to, the core promoter of the Rsyn7 promoter (Int'l Patent Application Publication No. WO 99/43838 and U.S. Pat. No. 6,072,050), the core 35S CaMV promoter, and the like. Other weak constitutive promoters are described, for example, in U.S. Pat. Nos. 5,608,149; 5,608,144; 5,604,121; 5,569,597; 5,466,785; 5,399,680; 5,268,463; 5,608,142 and 6,177,611.

Weak promoters can be used when designing expression cassettes for NB-LRR proteins, as NB-LRR genes preferably are constitutively expressed at low levels because high levels can lead to cell death in the absence of pathogens.

The expression cassette can include other control sequences 5' to the coding sequence. For example, the expression cassette can include a 5' leader sequence, which can act to enhance translation. Examples of 5' leader sequences include, but are not limited to, picornavirus leaders (e.g., encephalomyocarditis virus (EMCV) leader; Elroy-Stein et al. (1989) *Proc. Natl. Acad. Sci. USA* 86:6126-6130); potyvirus leaders (e.g., tobacco etch virus (TEV) leader; Gallie et al. (1995) *Gene* 165:233-238); maize dwarf mosaic virus (MDMV) leader (Allison et al. (1986) *Virology* 154:9-20); human immunoglobulin heavy-chain binding protein (BiP; Macejak et al. (1991) *Nature* 353:90-94); untranslated leader from the coat protein mRNA of alfalfa mosaic virus (AMV RNA 94; Jobling et al. (1987) *Nature* 325:622-625); tobacco mosaic virus (TMV) leader (Gallie et al., "Eukaryotic viral 5'-leader sequences act as translational enhancers in eukaryotes and prokaryotes" 237-256 In: Molecular Biology of RNA (Cech ed., Liss 1989)); and maize chlorotic mottle virus (MCMV) leader (Lommel et al. (1991) *Virology* 81:382-385). See also, Della-Cioppa et al. (1987) *Plant Physiol.* 84:965-968; and Gallie (1996) *Plant Mol. Biol.* 32:145-158. Other methods or sequences known to enhance translation also can be used, for example, introns, and the like.

The expression cassette also can include a coding sequence for the modified substrate protein of the pathogen-specific protease and/or NB-LRR protein. As discussed above, the modified substrate protein includes a heterologous protease recognition sequence. The heterologous protease recognition sequence can be located within, for example, an exposed loop of the substrate protein. As noted above, nucleic and amino acid sequences are well known in the art for many protease recognition sequences that can be inserted into the substrate protein such as PBS1. In addition, nucleic and amino acid sequences are known in the art for various NB-LRR proteins. These sequences can be used when constructing the expression cassette(s).

For example, the coding sequence can be SEQ ID NO:5 (modified PBS1 having an AvrRpt2 protease recognition sequence) operably linked to the native PBS1 promoter (SEQ ID NO:9). Alternatively, the coding sequence can be SEQ ID NO:7 (modified PBS1 having a TEV protease recognition sequence) operably linked to the native PBS1 promoter. Likewise, the coding sequence can include a NB-LRR protein such as RPS5 when the modified substrate protein is based upon PBS1 (or RPS2 when the modified substrate protein is based upon RIN4).

The control sequence(s) and/or the coding sequence therefore can be native/analogous to the host cell or to each other. Alternatively, the control sequence(s) and/or coding sequence can be heterologous to the host cell or to each other. As used herein, "heterologous" means a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

The expression cassette also can include a transcriptional and/or translational termination region that is functional in plants. The termination region can be native with the transcriptional initiation region (i.e., promoter), can be native with the operably linked coding sequence, can be native with the plant of interest, or can be derived from another source (i.e., foreign or heterologous to the promoter, the coding sequence, the plant host cell, or any combination thereof). Termination regions are typically located downstream (3'-direction) from the coding sequence. Termination regions include, but are not limited to, the potato proteinase inhibitor (Pin II) gene or the Ti-plasmid of *A. tumefaciens*, such as the octopine synthase and nopaline synthase termination regions. See e.g., Ballas et al. (1989) *Nucleic Acids Res.* 17:7891-7903; Guerineau et al. (1991) *Mol. Gen. Genet.* 262:141-144; Joshi et al. (1987) *Nucleic Acid Res.* 15:9627-9639; Mogen et al. (1990) *Plant Cell* 2:1261-1272; Munroe et al. (1990) *Gene* 91:151-158; Proudfoot (1991) *Cell* 64:671-674; and Sanfacon et al. (1991) *Genes Dev.* 5:141-149.

The expression cassette also can include one or more linkers. As used herein, "linker" means a nucleotide sequence that functions to link one element of the expression cassette with another without otherwise contributing to the transcription or translation of a nucleotide sequence of interest when present in the expression cassette. The linker can include plasmid sequences, restriction sequences and/or sequences of a 5'-untranslated region (5'-UTR). Alternatively, the linker further can include nucleotide sequences encoding the additional amino acid residues that naturally flank the heterologous protease recognition sequence in the substrate protein from which it was isolated. The length and sequence of the linker can vary and can be about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, 500, 600, 700, 800, 900, 1000 nucleotides or greater in length.

Just as expression of the modified substrate protein and/or NB-LRR protein can be targeted to specific tissues or cell types by appropriate use of promoters, it also can be targeted to different locations within a cell of a plant host by appropriate use of signal and/or targeting peptide sequences. Unlike a promoter, which acts at the transcriptional level, signal and/or targeting peptide sequences are part of the initial translation product. Therefore, the expression cassette also can include a signal and/or targeting peptide sequence. Examples of such sequences include, but are not limited to, the transit peptide for the acyl carrier protein, the small subunit of RUBISCO, plant EPSP synthase, and the like. See, Archer et al. (1990) *J. Bioenerg. Biomemb.* 22:789-810; Clark et al. (1989) *J. Biol. Chem.* 264:17544-17550; Daniell (1999) *Nat. Biotech.* 17:855-856; de Castro Silva Filho et al. (1996) *Plant Mol. Biol.* 30:769-780; Della-Cioppa et al. (1987) *Plant Physiol.* 84:965-968; Lamppa et al. (1988) *J. Biol. Chem.* 263:14996-14999; Lawrence et al. (1997) *J. Biol. Chem.* 272:20357-20363; Romer et al. (1993) *Biochem. Biophys. Res. Commun.* 196:1414-1421; Schmidt et al. (1993) *J. Biol. Chem.* 268:27447-27457; Schnell et al. (1991) *J. Biol. Chem.* 266:3335-3342; Shah et al. (1986) *Science* 233:478-481; Von Heijne et al. (1991) *Plant Mol. Biol. Rep.* 9:104-126; and Zhao et al. (1995) *J. Biol. Chem.* 270:6081-6087; as well as U.S. Pat. No. 6,338,168.

It may be desirable to locate the modified substrate protein and/or NB-LRR protein on specific plant membranes such as the plasma membrane or tonoplast membrane. This can be accomplished, for example, by adding specific amino acid sequences to the N-terminus of these proteins by adding specific sequences to the expression cassette as described in Raikhel & Chrispeels, "Protein sorting and vesicle traffic" In: Biochemistry and Molecular Biology of Plants (Buchanan et al. eds., American Society of Plant Physiologists 2000). See also, Denecke et al. (1992) *EMBO J.* 11:2345-2355; Denecke et al. (1993) *J. Exp. Bot.* 44:213-221; Gomord et al. (1996) *Plant Physiol. Biochem.* 34:165-181; Lehmann et al. (2001) *Plant Physiol.* 127:436-449; Munro & Pelham (1986) *Cell* 46:291-300; Munro & Pelham (1987) *Cell* 48:899-907; Vitale et al. (1993) *J. Exp. Bot.* 44:1417-1444; and Wandelt et al. (1992) *Plant J.* 2:181-192.

Additional guidance on subcellular targeting of proteins in plants can be found, for example, in Bruce (2001) *Biochim Biophys Acta* 1541:2-21; Emanuelsson et al. (2000) *J. Mol. Biol.* 300:1005-1016; Emanuelsson & von Heijne (2001) *Biochim Biophys Acta* 1541:114-119; Hadlington & Denecke (2000) *Curr. Opin. Plant Biol.* 3:461-468; Nicchitta (2002) *Curr. Opin. Cell Biol.* 14:412-416; and Silva-Filho (2003) *Curr. Opin. Plant Biol.* 6:589-595.

The expression cassette also can include nucleotide sequences encoding agronomic and pesticidal polypeptides, and the like. Such sequences can be stacked with any combination of nucleotide sequences to create plant cells, plants parts and plants with a desired phenotype. For example, the nucleic acid molecule encoding modified substrate protein and/or NB-LRR protein can be stacked with nucleotide sequences encoding a pesticidal polypeptide such as a δ-endotoxin. The combinations generated also can include multiple copies of any one of the nucleotide sequences of interest. Examples of other nucleotide sequences of interest include, but are not limited to, sequences encoding for high oil (U.S. Pat. No. 6,232,529); balanced amino acids (hordothionins; U.S. Pat. Nos. 5,703,409; 5,885,801; 5,885,802 and 5,990,389); barley high lysine (Williamson et al. (1987) *Eur. J. Biochem.* 165:99-106; and Int'l Patent Application Publication No. WO 98/20122); high methionine proteins (Pedersen et al. (1986) *J. Biol. Chem.* 261:6279-6284; Kirihara et al. (1988) *Gene* 71:359-370; and Musumura et al. (1989) *Plant Mol. Biol.* 12:123-130); increased digestibility (modified storage proteins; U.S. Pat. No. 6,858,778); and thioredoxins (U.S. Pat. No. 7,009,087).

The nucleotide sequence encoding the modified substrate protein and/or NB-LRR disease resistance protein also can be stacked with nucleotide sequences encoding polypeptides for herbicide resistance (e.g., glyphosate or HPPD resistance; see, e.g., EPSPS genes, GAT genes (Int'l Patent Application Publication Nos. WO 02/36782 and WO 03/092360; and US Patent Application Publication No. 2004/0082770); lectins (Van Damme et al. (1994) *Plant Mol. Biol.* 24:825-830); fumonisin detoxification (U.S. Pat. No. 5,792,931); acetolactate synthase (ALS) mutants that lead to herbicide resistance such as the S4 and/or Hra mutations; inhibitors of glutamine synthase such as phosphinothricin or basta (e.g., bar gene); modified starches (ADPG pyrophosphorylases (AGPase), starch synthases (SS), starch branching enzymes (SBE) and starch debranching enzymes (SDBE)); and polymers or bioplastics (U.S. Pat. No. 5,602,321); beta-ketothiolase, polyhydroxybutyrate synthase and acetoacetyl-CoA reductase (Schubert et al. (1988) *J. Bacteriol.* 170:5837-5847).

The nucleotide sequence encoding the modified substrate protein and/or NB-LRR disease resistance protein also can be stacked with nucleotide sequences encoding for agronomic traits such as male sterility (U.S. Pat. No. 5,583,210), stalk strength, flowering time or transformation technology traits such as cell cycle regulation or gene targeting (Int'l Patent Application Publication Nos. and WO 99/25821; WO 99/61619 and WO 00/17364).

These stacked combinations can be created by any method including, but not limited, to cross breeding plants by any conventional or TopCross™ methodology (DuPont Specialty Grains; Des Moines, Iowa), zinc finger nucleases (ZFNs), transcription activator-like effector nucleases (TAL-ENs) or other genetic transformation. If the traits are stacked by genetically transforming the plants, the nucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate expression cassettes (trans) or contained on the same transformation cassette (cis). Expression of the sequences can be driven by the same promoter or by different promoters. In certain instances, it may be desirable to introduce an expression cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, Int'l Patent Application Publication Nos. WO 99/25821; WO 99/25840; WO 99/25853; WO 99/25854 and WO 99/25855.

In addition to the above, it is contemplated that the nucleic acid constructs can be used in the form of a system, particularly when used in plant cells, plant parts and plants that lack a substrate protein of a pathogen-specific protease and NB-LRR protein pair. Such systems can include one or more nucleic acid constructs, such as expression cassettes or vectors, having a promoter that drives expression in a plant, plant part or plant cell operably linked to a coding sequence for a modified substrate protein of a pathogen-specific protease, where the substrate protein has a heterologous protease recognition sequence, and a sequence for a promoter that drives expression in a plant, plant part or plant cell operably linked to a coding sequence for a NB-LRR protein. The promoters can be the same or can be distinct. For example, the first promoter can be an inducible promoter and the second promoter can be a constitutive promoter, especially a weak constitutive promoter. Alternatively, both the first and second promoters can be inducible, repressible or constitutive. The NB-LRR protein can associate with, and can be activated by, the modified substrate. Such systems therefore can be used to provide the protein pair to a plant cell, plant part or plant that does not natively express the protein pair.

Alternatively, the system can include a first nucleic acid construct having nucleotide sequence for a promoter that drives expression in a plant cell, plant part or plant operably linked to a coding sequence for a modified substrate protein of a pathogen-specific protease as described herein, and a second nucleic acid construct having a nucleotide sequence for a promoter that drives expression in a plant cell, plant part or plant operably linked to a coding sequence for a NB-LRR protein.

Additional nucleic acid constructs also can be included in the system, where each construct has a nucleotide sequence that encodes a distinct modified substrate protein, each having a heterologous recognition sequence for a separate pathogen-specific protease. Although each modified substrate protein has a heterologous recognition sequence distinct from one another, each can associate with, and can activate, the NB-LRR protein. For example, the nucleic acid construct(s) can encode (1) a PBS1 in which its endogenous AvrPphB cleavage site (SEQ ID NO:1) is replaced with a heterologous AvrRpt2 cleavage site (SEQ ID NO:2), (2) a PBS1 in which its endogenous AvrPphB cleavage site (SEQ ID NO:1) is replaced with a heterologous TEV protease cleavage site (SEQ ID NO:4) and/or (3) a PBS1 in which its endogenous AvrPphB cleavage site (SEQ ID NO:1) is replaced with a heterologous HopN1 cleavage site (SEQ ID NO:3). Similarly, the nucleic acid construct(s) can encode (1) a PBS1 in which its endogenous AvrPphB cleavage site (SEQ ID NO:1) is replaced with a heterologous SMV cleavage site (SEQ ID NO:27) and/or (2) a PBS1 in which its endogenous AvrPphB cleavage site (SEQ ID NO:1) is replaced with a heterologous BPMV protease cleavage site (SEQ ID NO:28). Although each of these modified substrate proteins would be targets for distinct pathogen-specific proteases, all would be expected to associate with and activate a RPS5 protein. In another example, the nucleic acid construct(s) can encode (1) a RIN4 in which its endogenous AvrRpt2 cleavage site (SEQ ID NO:2) is replaced with a heterologous AvrPphB cleavage site (SEQ ID NO:1). (2) a RIN4 in which its endogenous AvrRpt2 cleavage site (SEQ ID NO:2) is replaced with a heterologous TEV protease cleavage site (SEQ ID NO:4) and/or (3) a RIN4 in which its endogenous AvrRpt2 cleavage site (SEQ ID NO:2) is replaced with a heterologous HopN1 cleavage site (SEQ ID NO:3). Similarly, the nucleic acid construct(s) can encode (1) a RIN4 in which its endogenous AvrRpt2 cleavage site (SEQ ID NO:2) is replaced with a heterologous SMV cleavage site (SEQ ID NO:27) and/or (2) a RIN4 in which its endogenous AvrRpt2 cleavage site (SEQ ID NO:2) is replaced with a heterologous BPMV protease cleavage site (SEQ ID NO:28). Although each of these modified substrate proteins would be targets for distinct pathogen-specific proteases, all would be expected to associate with and activate a RPS2 protein.

As such, the first nucleic acid construct can encode more than one modified substrate protein, where each modified substrate protein has a heterologous recognition sequence distinct from one another and where each can associate with, and can activate, the NB-LRR protein. Alternatively, the second nucleic acid construct can encode one or more modified substrate proteins, where each modified substrate protein has a heterologous recognition sequence distinct from one another and where each can associate with, and can activate, the NB-LRR protein. As above, the promoters can be the same or can be distinct. Such systems can be used to provide the protein pair to a plant cell, plant part or plant that does not natively express the protein pair or can be used to provide more than one modified substrate to a plant cell, plant part or plant.

Regardless of whether used as individual nucleic acid constructs or systems, and where appropriate, the nucleotide sequences can be optimized for increased expression in plants. That is, the nucleotide sequences can be synthesized using plant-preferred codons for improved expression. Methods for optimizing nucleotide sequences for expression in plants are well known in the art. See, Campbell & Gowri (1990) *Plant Physiol.* 92:1-11; Murray et al. (1989) *Nucleic Acids Res.* 17:477-498; and Wada et al. (1990) *Nucl. Acids*

Res. 18:2367-2411; as well as U.S. Pat. Nos. 5,096,825; 5,380,831; 5,436,391; 5,625,136; 5,670,356 and 5,874,304.

Likewise, additional sequence modifications are known to enhance nucleotide sequence expression in plants. These include elimination of sequences encoding spurious polyadenylation signals, exon-intron splice site signals, transposon-like repeats, and other such well-characterized sequences that may be deleterious to gene expression. The G-C content of the sequence can be adjusted to levels average for a given cellular host, as calculated by reference to known genes expressed in the host plant. When possible, the nucleotide sequence can be modified to avoid predicted hairpin secondary mRNA structures.

Methods of constructing expression cassettes are well known in the art and can be found, for example, in Balbás & Lorence, *Recombinant Gene Expression: Reviews and Protocols,* 2nd ed. (Humana Press 2004); Davis et al., *Basic Methods in Molecular Biology* (Elsevier Press 1986); Sambrook & Russell (2001), supra; Tijssen, *Laboratory Techniques in Biochemistry and Molecular Biology—Hybridization with Nucleic Acid Probes* (Elsevier 1993); Ausubel et al. (1995), supra; as well as U.S. Pat. Nos. 6,664,387; 7,060,491; 7,345,216 and 7,494,805.

The expression cassette therefore can include at least, in the direction of transcription (i.e., 5' to 3' direction), a plant promoter that is functional in a plant cell, plant part or plant operably linked to a nucleotide sequence encoding a modified substrate protein having a heterologous protease recognition sequence. In some instances, the expression cassette also can include a nucleotide sequence encoding a NB-LRR disease resistance protein.

To assist in introducing the nucleotide sequences of interest into the appropriate host cells, the expression cassette can be incorporated or ligated into a vector. As used herein, "vector" means a replicon, such as a plasmid, phage or cosmid, to which another nucleic acid segment may be attached so as to bring about the replication of the attached segment. A vector is capable of transferring nucleic acid molecules to the host cells. Bacterial vectors typically can be of plasmid or phage origin.

Typically, the terms "vector construct," "expression vector," "gene expression vector," "gene delivery vector," "gene transfer vector," and "expression cassette" all refer to an assembly that is capable of directing the expression of a sequence or gene of interest. Thus, the terms include cloning and expression vehicles.

Vectors typically contain one or a small number of restriction endonuclease recognition sites where a nucleic acid molecule of interest can be inserted in a determinable fashion without loss of essential biological function of the vector, as well as a selectable marker that can be used for identifying and selecting cells transformed with the vector.

A vector therefore can be capable of transferring nucleic acid molecule to target cells (e.g., bacterial plasmid vectors, particulate carriers and liposomes). The selection of vector will depend upon the preferred transformation technique and the target specie for transformation. The most commonly used plant transformation vectors are binary vectors because of their ability to replicate in intermediate host cells such as *E. coli* and *A. tumefaciens.* The intermediate host cells allow one to increase the copy number of the cloning vector and/or to mediate transformation of a different host cell. With an increased copy number, the vector containing the expression cassette of interest can be isolated in significant quantities for introduction into the desired plant. General descriptions of plant vectors can be found, for example, in Gruber et al., "Vectors for plant transformation" 89-119 In: Methods in Plant Molecular Biology & Biotechnology (Glich et al. eds., CRC Press 1993). Examples of vectors for use with *A. tumefaciens* can be found, for example, in U.S. Pat. No. 7,102,057.

Restriction enzymes can be used to introduce cuts into the target nucleic acid molecule (e.g., nucleotide sequence encoding a modified substrate protein and/or NB-LRR protein) and the plasmid to facilitate insertion of the target into the vector such as a plasmid. Moreover, restriction enzyme adapters such as EcoRI/NotI adapters can be added to the target mRNA when the desired restriction enzyme sites are not present within it. Methods of adding restriction enzyme adapters are well known in the art. See, Krebs et al. (2006) *Anal. Biochem.* 350:313-315; and Lönneborg et al. (1995), supra. Likewise, kits for adding restriction enzyme sites are commercially available, for example, from Invitrogen (Carlsbad, Calif.).

Alternatively, viruses such as bacteriophages can be used as the vector to deliver the target mRNA to competent host cells. Vectors can be constructed using standard molecular biology techniques as described, for example, in Sambrook & Russell (2001), supra.

As noted above, selectable markers can be used to identify and select transformed plants, plant parts or plant host cells. Selectable markers include, but are not limited to, nucleotide sequences encoding antibiotic resistance, such as those encoding neomycin phosphotransferase II (NEO), hygromycin phosphotransferase (HPT), as well as nucleotide sequences encoding resistance to ampicillin, kanamycin, spectinomycin or tetracycline, and even nucleotide sequences encoding herbicidal compounds such as glufosinate ammonium, bromoxynil, imidazolinones and 2,4-dichlorophenoxyacetate (2,4-D).

Additional selectable markers can include phenotypic markers such as nucleic acid sequences encoding β-galactosidase, β-glucoronidase (GUS; Jefferson (1987) *Plant Mol. Biol. Rep.* 5:387-405); luciferase (Teeri et al. (1989) *EMBO J.* 8:343-350); anthocyanin production (Ludwig et al. (1990) *Science* 247:449-450), and fluorescent proteins such as green fluorescent protein (GFP; Chalfie et al. (1994) *Science* 263:802-805; Fetter et al. (2004) *Plant Cell* 16:215-228; and Su et al. (2004) *Biotechnol. Bioeng.* 85:610-619); cyan fluorescent protein (CYP; Bolte et al. (2004) *J. Cell Science* 117:943-954; and Kato et al. (2002) *Plant Physiol.* 129:913-942), and yellow fluorescent protein (PhiYFP™, available from Evrogen (Moscow, Russia); Bolte et al. (2004) *J. Cell Science* 117:943-954). For additional selectable markers, Baim et al. (1991) *Proc. Natl. Acad. Sci. USA* 88:5072-5076; Barkley & Bourgeois, "Repressor recognition of operator and effectors" 177-120 In: The Operon (Miller & Reznikoff eds., Cold Spring Harbor Laboratory Press 1980); Bonin (1993) Ph.D. Thesis, University of Heidelberg; Brown et al. (1987) *Cell* 49:603-612; Christopherson et al. (1992) *Proc. Natl. Acad. Sci. USA* 89:6314-6318; Degenkolb et al. (1991) *Antimicrob. Agents Chemother.* 35:1591-1595; Deuschle et al. (1989) *Proc. Natl. Acad. Sci. USA* 86:5400-5404; Deuschle et al. (1990) *Science* 248:480-483; Figge et al. (1988) *Cell* 52:713-722; Fuerst et al. (1989) *Proc. Natl. Acad. Sci. USA* 86:2549-2553; Gill et al. (1988) *Nature* 334:721-724; Gossen et al. (1992) *Proc. Natl. Acad. Sci. USA* 89:5547-5551; Gossen (1993) Ph.D. Thesis, University of Heidelberg; Hillenand-Wissman (1989) *Topics Mol. Struc. Biol.* 10:143-162; Hlavka et al., *Handbook of Experimental Pharmacology,* Vol. 78 (Springer-Verlag 1985); Hu et al. (1987) *Cell* 48:555-566; Kleinschnidt et al. (1988) *Biochemistry* 27:1094-1104; Labow et al. (1990) *Mol. Cell. Biol.* 10:3343-

3356; Oliva et al. (1992) *Antimicrob. Agents Chemother.* 36:913-919; Reines et al. (1993) *Proc. Natl. Acad. Sci. USA* 90:1917-1921; Reznikoff (1992) *Mol. Microbiol.* 6:2419-2422; Yao et al. (1992) *Cell* 71:63-72; Yarranton (1992) *Curr. Opin. Biotech.* 3:506-511; Wyborski et al. (1991) *Nucleic Acids Res.* 19:4647-4653; and Zambretti et al. (1992) *Proc. Natl. Acad. Sci. USA* 89:3952-3956. The above list of selectable markers is not intended to be limiting, as any selectable marker can be used.

The vector therefore can be selected to allow introduction of the expression cassette into the appropriate host cell such as a plant host cell. Bacterial vectors are typically of plasmid or phage origin. Appropriate bacterial cells are infected with phage vector particles or transfected with naked phage vector DNA. If a plasmid vector is used, the cells are transfected with the plasmid vector DNA.

The present disclosure therefore includes nucleotide constructs such as expression cassettes and vectors having a nucleotide sequence encoding a modified substrate protein of a pathogen-specific protease, where the modified substrate protein has a heterologous protease recognition sequence. In addition, the nucleic acid constructs can include a nucleotide sequence encoding a NB-LRR protein. The nucleic acid constructs can be introduced into an organism such as a plant to confer resistance to plant pathogens expressing specific proteases.

Recombinant Peptides, Polypeptides and Proteins

Compositions of the present disclosure also include isolated or purified, modified substrate proteins of a pathogen-specific protease, where the substrate proteins have heterologous protease recognition sequences, as well as fragments and/or variants thereof. Methods for producing peptide, polypeptides and proteins in plant cells, plant parts and plants are discussed elsewhere herein.

Methods of isolating or purifying peptides, polypeptides and proteins are well known in the art. See, Ehle & Horn (1990) *Bioseparation* 1:97-110; Hengen (1995) *Trends Biochem Sci.* 20:285-286; *Basic Methods in Protein Purification and Analysis: A Laboratory Manual* (Simpson et al. eds., Cold Spring Harbor Laboratory Press 2008); Regnier (1983) *Science* 222:245-252; Shaw, "Peptide purification by reverse-phase HPLC" 257-287 In: Methods in Molecular Biology, Vol. 32 (Walker ed., Humana Press 1994); as well as US Patent Application Publication No. 2009/0239262; and U.S. Pat. Nos. 5,612,454; 7,083,948; 7,122,641; 7,220,356 and 7,476,722.

As used herein, "peptide," "polypeptide" and "protein" are used interchangeably to mean a polymer of amino acid residues. The terms apply to amino acid polymers in which one or more amino acid residues is an artificial chemical analogue of a corresponding naturally occurring amino acid, as well as to naturally occurring amino acid polymers.

As used herein, "residue," "amino acid residue" and "amino acid" are used interchangeably to mean an amino acid that is incorporated into molecule such as a peptide, polypeptide or protein. The amino acid can be a naturally occurring amino acid and, unless otherwise limited, may encompass known analogues of natural amino acids that can function in a similar manner as naturally occurring amino acids.

As used herein, "recombinant," when used in connection with a peptide, polypeptide or protein, means a molecule that has been created or modified through deliberate human intervention such as by protein engineering. For example, a recombinant polypeptide is one having an amino acid sequence that has been modified to include an artificial amino acid sequence or to include some other amino acid sequence that is not present within its native/endogenous/non-recombinant form.

Further, a recombinant peptide, polypeptide or protein has a structure that is not identical to that of any naturally occurring peptide, polypeptide or protein. As such, a recombinant peptide, polypeptide or protein can be prepared by synthetic methods such as those known to one of skill in the art.

If, and when, modified substrate proteins are to be isolated, complete purification is not required. For example, the modified substrate proteins described herein can be isolated and purified from normally associated material in conventional ways, such that in the purified preparation, the proteins are the predominant species in the preparation. At the very least, the degree of purification is such that extraneous material in the preparation does not interfere with use of the proteins in the manner disclosed herein. The peptide, polypeptide or protein can be at least about 80%, at least about 85%, at least about 90%, at least about 91%, at least about 92%, at least about 93%, at least about 94%, at least about 95%, at least about 96%, at least about 97%, at least about 98% or at least about 99% pure. Alternatively stated, the polypeptide is substantially free of cellular material such that preparations of the polypeptide can contain less than about 30%, 25%, 20%, 15%, 10%, 9%, 8%, 7%, 6%, 5%, 4%, 3%, 2%, or 1% (dry weight) of contaminating protein. When the polypeptide or an active variant or fragment thereof is recombinantly produced, culture medium represents less than about 30%, 25%, 20%, 15%, 10%, 9%, 8%, 7%, 6%, 5%, 4%, 3%, 2%, or 1% (dry weight) of chemical precursors or non-protein-of-interest chemicals.

It is known in the art that amino acids within the same conservative group can typically substitute for one another without substantially affecting the function of a protein. For the purpose of the present disclosure, such conservative groups are set forth in Table 3 and are based on shared properties. See also, Alberts et al., "Small molecules, energy, and biosynthesis" 56-57 In: Molecular Biology of the Cell (Garland Publishing Inc. $3^{rd}$ ed. 1994).

TABLE 3

Amino Acid Conservative Substitutions.

| Residue | Side Chain Polarity | Side Chain pH | Hydropathy Index | Preferred Conservative Substitution |
|---------|---------------------|---------------|------------------|-------------------------------------|
| Ala (A) | Non-polar | Neutral | 1.8 | Ser |
| Arg (R) | Polar | Basic (strongly) | −4.5 | Lys, Gln |
| Asn (N) | Polar | Neutral | −3.5 | Gln, His |
| Asp (D) | Polar | Acidic | −3.5 | Glu |
| Cys (C) | Non-polar | Neutral | 2.5 | Ser |
| Gln (Q) | Polar | Neutral | −3.5 | Asn, Lys |
| Glu (E) | Polar | Acidic | −3.5 | Asp |
| Gly (G) | Non-polar | Neutral | −0.4 | Pro |
| His (H) | Polar | Basic (weakly) | −3.2 | Asn, Gln |
| Ile (I) | Non-polar | Neutral | 4.5 | Leu, Val |
| Leu (L) | Non-polar | Neutral | 3.8 | Ile, Val |
| Lys (K) | Polar | Basic | −3.9 | Arg, Gln |
| Met (M) | Non-polar | Neutral | 1.9 | Leu, Ile |
| Phe (F) | Non-polar | Neutral | 2.8 | Met, Leu, Tyr |
| Pro (P) | Non-polar | Neutral | −1.6 | Gly |
| Ser (S) | Polar | Neutral | −0.8 | Thr |
| Thr (T) | Polar | Neutral | −0.7 | Ser |
| Trp (W) | Non-polar | Neutral | −0.9 | Tyr |
| Tyr (Y) | Polar | Neutral | −1.3 | Trp, Phe |
| Val (V) | Non-polar | Neutral | 4.2 | Ile, Leu |

The following six groups each contain amino acids that are typical but not necessarily exclusive conservative substitutions for one another: 1. Alanine (A), Serine (S), Threonine (T); 2. Aspartic acid (D), Glutamic acid (E); 3. Asparagine (N), Glutamine (Q); 4. Arginine (R), Lysine (K); 5. Isoleucine (I), Leucine (L), Methionine (M), Valine (V); and 6. Phenylalanine (F), Tyrosine (Y), Tryptophan (W).

Substantial changes in function of a peptide, polypeptide or protein can be made by selecting substitutions that are less conservative than those listed in the table above, that is, by selecting residues that differ more significantly in their effect on maintaining (a) the structure of the polypeptide backbone in the area of substitution, (b) the charge or hydrophobicity of the polypeptide at the target site, or (c) the bulk of a side chain. The substitutions that in general can be expected to produce the greatest changes in the polypeptide's properties will be those in which (a) a hydrophilic residue, for example, seryl or threonyl, is substituted by a hydrophobic residue, for example, leucyl, isoleucyl, phenylalanyl, valyl or alanyl; (b) a cysteine or proline is substituted by any other residue; (c) a residue having an electropositive side chain, for example, lysyl, arginyl or histidyl, is substituted by an electronegative side chain, for example, glutamyl or aspartyl; (d) a residue having a bulky side chain, for example, phenylalanyl, is substituted by a residue not having a side chain, for example, glycyl; or (e) by increasing the number of sulfation or glycosylation.

In one aspect, the present disclosure is directed to an isolated polypeptide encoded by the recombinant nucleic acid molecule comprising about 90% identity to an amino acid sequence selected from the group consisting of SEQ ID NO:6 and SEQ ID NO:8, wherein the polypeptide is a substrate protein of a plant pathogen-specific protease. In another embodiment, the isolated polypeptide can comprise about 95% identity to an amino acid sequence selected from SEQ ID NO:6 and SEQ ID NO:8, wherein the polypeptide is a substrate protein of a plant pathogen-specific protease. In other embodiments, the isolated polypeptide can comprise about 96% identity, about 97% identity, about 98% identity and about 99% identity to an amino acid sequence selected from SEQ ID NO:6 and SEQ ID NO:8, wherein the polypeptide is a substrate protein of a plant pathogen-specific protease.

An example of a modified substrate protein of a pathogen-specific protease therefore includes SEQ ID NO:6 (modified PBS1 having an AvrRpt2 protease recognition sequence). Another example of a modified substrate protein of a pathogen-specific protease as described herein includes SEQ ID NO:8 (modified PBS1 having a TEV protease recognition sequence). Another example of a modified substrate protein of a pathogen-specific protease includes PBS1 in which its endogenous AvrPphB cleavage site (SEQ ID NO:1) is replaced with a heterologous HopN1 cleavage site (SEQ ID NO:3). Another example of a modified substrate protein of a pathogen-specific protease includes PBS1 in which its endogenous AvrPphB cleavage site (SEQ ID NO:1) is replaced with a heterologous SMV cleavage site (SEQ ID NO:27). Another example of a modified substrate protein of a pathogen-specific protease includes PBS1 in which its endogenous AvrPphB cleavage site (SEQ ID NO:1) is replaced with a heterologous BPMV cleavage site (SEQ ID NO:28). Another example of a modified substrate protein of a pathogen-specific protease includes RIN4 in which its endogenous AvrRpt2 cleavage site (SEQ ID NO:2) is replaced with a heterologous AvrPphB cleavage site (SEQ ID NO:1). Another example of a modified substrate protein of a pathogen-specific protease includes RIN4 in which its endogenous AvrRpt2 cleavage site (SEQ ID NO:2) is replaced with a heterologous TEV protease cleavage site (SEQ ID NO:4). Another example of a modified substrate protein of a pathogen-specific protease includes RIN4 in which its endogenous AvrRpt2 cleavage site (SEQ ID NO:2) is replaced with a heterologous HopN1 cleavage site (SEQ ID NO:3). Another example of a modified substrate protein of a pathogen-specific protease includes RIN4 in which its endogenous AvrRpt2 cleavage site (SEQ ID NO:2) is replaced with a heterologous SMV cleavage site (SEQ ID NO:27). Another example of a modified substrate protein of a pathogen-specific protease includes RIN4 in which its endogenous AvrRpt2 cleavage site (SEQ ID NO:2) is replaced with a heterologous BPMV cleavage site (SEQ ID NO:28). As noted above, the endogenous protease cleavage sequence, which is a preferred location for the heterologous protease recognition sequence, typically can be located in an exposed loop of the substrate protein.

In addition to the full-length amino acid sequence of the modified substrate protein of the pathogen-specific protease, it is intended that the modified substrate protein can be a fragment or variant thereof that is capable of being recognized by the plant pathogen protease and/or its corresponding NB-LRR protein. For amino acid sequences, "fragment" means a portion of the amino acid sequence of a reference polypeptide or protein. Fragments of an amino acid sequence may retain the biological activity of the reference polypeptide or protein. For example, less than the entire amino acid sequence of the modified substrate protein can be used and may have substrate protein activity and/or NB-LRR protein binding activity. Thus, fragments of the reference polypeptide or protein can be at least about 150, 200, 250, 300, 350, 400 or 450 amino acid residues, or up to the number of amino acid residues present in a full-length modified substrate protein. For example, about 80 amino acids can be deleted from the N-terminus of PBS1 while retaining function. See, DeYoung et al. (2012), supra. Alternatively, about 100 amino acids can be deleted from the C-terminus of PBS1 while retaining function. Id.

Likewise, a "variant" peptide, polypeptide or protein means a substantially similar amino acid sequence to the amino acid sequence of a reference peptide, polypeptide or protein. For amino acid sequences, a variant comprises an amino acid sequence derived from a reference peptide, polypeptide or protein by deletion (so-called truncation) of one or more amino acids at the N-terminal and/or C-terminal end of the amino acid sequence of the reference; deletion and/or addition of one or more amino acids at one or more internal sites in the amino acid sequence of the reference; or substitution of one or more amino acids at one or more sites in the amino acid sequence of the reference. Variant peptides, polypeptides or proteins encompassed by the present disclosure are biologically active, that is, they continue to possess the desired biological activity of the reference peptide, polypeptide or protein as described herein. Such variants may result from, for example, genetic polymorphism or human manipulation. Biologically active variants will have at least about 70%, 75%, 80%, 85%, 90%, 91%, 92%, 93%, 94%, 95%, 96%, 97%, 98%, 99% or more sequence identity to the amino acid sequence of the reference peptide polypeptide or protein as determined by sequence alignment programs and parameters described above. For example, a biologically active variant of a modified substrate protein may differ by as few as 1-15 amino acid residues, as few as 1-10, such as 6-10, as few as 5, as few as 4, 3, 2, or even 1 amino acid residue. It is contemplated that PBS1 orthologues from other plant species can be substituted for *Arabidopsis* PBS1, which typically have about 90% or higher identity.

Deletions, insertions and substitutions of the modified substrate proteins are not expected to produce radical changes in the characteristics of the polypeptides. However, when it is difficult to predict the exact effect of the substitution, deletion or insertion in advance of doing so, one of skill in the art will appreciate that the effect can be evaluated by routine activity assays as described herein.

As above, variant peptides, polypeptides and proteins also encompass sequences derived from a mutagenic and recombinogenic procedure such as DNA shuffling. With such a procedure, one or more nucleic acid molecules can be manipulated to encode new modified substrate proteins possessing the desired properties. In this manner, libraries of recombinant nucleic acid molecules can be generated from a population of related nucleic acid molecules comprising sequence regions that have substantial sequence identity and can be homologously recombined in vitro or in vivo. For example, using this approach, sequence motifs encoding a domain of interest can be shuffled between the nucleic acid molecules identified by the methods described herein and other known substrate protein-encoding nucleic acid molecules to obtain a new nucleic acid molecule that encodes a modified substrate protein with an improved property such as increased activity or an expanded pH or temperature range. As such, a peptide, polypeptide or protein of the present disclosure can have many modifications.

The present disclosure therefore includes recombinant modified substrate proteins of pathogen-specific proteases, where the substrate proteins have heterologous protease recognition sequences, as well as active fragments or variants thereof.

Transformed Plant Cells, Plant Parts and Plants

Compositions of the present disclosure also include transformed plant cells, plant parts and plants (i.e., subject plant cells, plant parts or plants) having a resistance to an increased number of plant pathogens when compared with control/native plant cells, plant parts or plants.

The transformed plant cells, plant parts or plants can have at least one nucleic acid molecule, nucleic acid construct, expression cassette or vector as described herein that encodes a modified substrate protein of a pathogen-specific protease, where the modified substrate protein has a heterologous protease recognition sequence.

As used herein, "subject plant cell," "subject plant part" or "subject plant" means one in which a genetic alteration, such as transformation, has been effected as to a nucleic acid molecule of interest, or is a plant cell, plant part or plant that descended from a plant cell, plant part or plant so altered and that comprises the alteration.

As used herein, "control plant cell," "control plant part" or "control plant" means a reference point for measuring changes in phenotype of the subject plant cell, plant part or plant. A control plant cell, plant part or plant can comprise, for example: (a) a wild-type plant cell, plant part or plant (i.e., of the same genotype as the starting material for the genetic alteration that resulted in the subject plant cell, plant part or plant); (b) a plant cell, plant part or plant of the same genotype as the starting material, but which has been transformed with a null construct (i.e., with a construct that has no known effect on the trait of interest, such as a construct comprising a marker gene); (c) a plant cell, plant part or plant that is a non-transformed segregant among progeny of a subject plant cell, plant part or plant; (d) a plant cell, plant part or plant genetically identical to the subject plant cell, plant part or plant, but which is not exposed to conditions or stimuli that would induce expression of the gene of interest; or (e) the subject plant cell, plant part or plant itself, under conditions in which the nucleic acid molecule/construct of interest is not expressed.

Methods of introducing nucleotide sequences into plants, plant parts or plant host cells are well known in the art and are discussed in greater detail below.

As used herein, "plant cell" or "plant cells" means a cell obtained from or found in seeds, suspension cultures, embryos, meristematic regions, callus tissue, leaves, roots, shoots, gametophytes, sporophytes, pollen and microspores. Plant cell also includes modified cells, such as protoplasts, obtained from the aforementioned tissues, as well as plant cell tissue cultures from which plants can be regenerated, plant calli and plant clumps.

As used herein, "plant part" or "plant parts" means organs such as embryos, pollen, ovules, seeds, flowers, kernels, ears, cobs, leaves, husks, stalks, stems, roots, root tips, anthers, silk and the like.

As used herein, "plant" or "plants" means whole plants and their progeny. Progeny, variants and mutants of the regenerated plants also are included, provided that they comprise the introduced nucleic acid molecule.

As used herein, "grain" means mature seed produced by commercial growers for purposes other than growing or reproducing the species. The class of plants that can be used in the methods described herein is generally as broad as the class of higher plants amenable to transformation techniques, including both monocotyledonous (monocots) and dicotyledonous (dicots) plants.

Examples of plant species of interest herein include, but are not limited to, corn (*Zea mays*), *Brassica* spp. (e.g., *B. napus, B. rapa, B. juncea*), particularly those *Brassica* species useful as sources of seed oil, alfalfa (*Medicago sativa*), rice (*Oryza sativa*), rye (*Secale cereale*), *sorghum* (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (0/ea *europaea*), *papaya* (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats (*Avena sativa*), barley (*Hordeum vulgare*), vegetables, ornamentals, and conifers.

Vegetables of interest include, but are not limited to, tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*).

Ornamentals of interest include, but are not limited to, azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers of interest include, but are not limited to, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow cedar (*Chamaecyparis nootkatensis*).

In some instances, the plant cells, plant parts or plants of interest are crop plants (e.g., corn, alfalfa, sunflower, *Brassica*, soybean, cotton, safflower, peanut, *sorghum*, wheat, millet, tobacco, etc.).

Other plants of interest include grain plants that provide seeds of interest, oil-seed plants, and leguminous plants. Seeds of interest include grain seeds, such as corn, wheat, barley, rice, *sorghum*, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

The present disclosure therefore includes transgenic plant cells, plant parts and plants having incorporated therein at least one nucleic acid molecule that encodes a modified substrate protein of a pathogen-specific protease, where the modified substrate protein has a heterologous protease sequence, to confer disease resistance to plant pathogens expressing specific proteases.

Methods

Methods of the present disclosure include introducing and expressing in a plant cell, plant part or plant a nucleic acid molecule or construct as described herein. As used herein, "introducing" means presenting to the plant cell, plant part or plant, a nucleic acid molecule or construct in such a manner that it gains access to the interior of a cell of the plant. The methods do not depend on the particular method for introducing the nucleic acid molecule or nucleic acid construct into the plant cell, plant part or plant, only that it gains access to the interior of at least one cell of the plant or plant part. Methods of introducing nucleotide sequences, selecting transformants and regenerating whole plants, which may require routine modification in respect of a particular plant species, are well known in the art. The methods include, but are not limited to, stable transformation methods, transient transformation methods, virus-mediated methods and sexual breeding. As such, the nucleic acid molecule or construct can be carried episomally or integrated into the genome of the host cell.

As used herein, "stable transformation" means that the nucleic acid molecule or construct of interest introduced into the plant integrates into the genome of the plant and is capable of being inherited by the progeny thereof. As used herein, "transient transformation" means that the nucleic acid molecule or construct of interest introduced into the plant is not inherited by progeny.

Methods of transforming plants and introducing a nucleotide sequence of interest into plants can and will vary depending on the type of plant, plant part or plant host cell (i.e., monocotyledonous or dicotyledonous) targeted for transformation. Methods of introducing nucleotide sequences into plant host cells therefore include *Agrobacterium*-mediated transformation (e.g., *A. rhizogenes* or *A. tumefaciens*; U.S. Pat. Nos. 5,563,055 and 5,981,840), calcium chloride, direct gene transfer (Paszkowski et al. (1984) *EMBO J.* 3:2717-2722), electroporation (Riggs et al. (1986) *Proc. Natl. Acad. Sci. USA* 83:5602-5606), microinjection (Crossway et al. (1986) *Biotechniques* 4:320-334), microprojectile bombardment/particle acceleration (McCabe et al. (1988) *Biotechnology* 6:923-926; and Tomes et al., "Direct DNA transfer into intact plant cells via microprojectile bombardment" In: Plant Cell, Tissue, and Organ Culture: Fundamental Methods (Gamborg & Phillips eds., Springer-Verlag 1995); as well as U.S. Pat. Nos. 4,945,050; 5,879,918; 5,886,244 and 5,932,782), polyethylene glycol (PEG), phage infection, viral infection, and other methods known in the art. See also, EP Patent Nos. 0 295 959 and 0 138 341.

A nucleic acid molecule or construct as described above herein can be introduced into the plant cell, plant part or plant using a variety of transient transformation methods. Methods of transiently transforming plant cells, plant parts or plants include, but are not limited to, *Agrobacterium* infection, microinjection or particle bombardment. See, Crossway et al. (1986) *Mol. Gen. Genet.* 202:179-185; Hepler et al. (1994) *Proc. Natl. Acad. Sci. USA* 91:2176-2180; Hush et al. (1994) *J. Cell Sci.* 107:775-784; and Nomura et al. (1986) *Plant Sci.* 44:53-58. Alternatively, the plant cell, plant part or plant can be transformed by viral vector systems or by precipitation of the nucleic acid molecule or construct in a manner that precludes subsequent release of the DNA. Thus, transcription from the particle-bound nucleotide sequence can occur, but the frequency with which it is released to become integrated into the genome is greatly reduced. Such methods include the use of particles coated with polyethylimine (PEI; Sigma; St. Louis, Mo.).

Likewise, the nucleic acid molecules or constructs as described herein can be introduced into the plant cell, plant part or plant by contacting it with a virus or viral nucleic acids. Generally, such methods involve incorporating the nucleic acid molecule or construct within a viral DNA or RNA molecule. It is recognized that the nucleotide sequences can be initially synthesized as part of a viral polyprotein, which later can be processed by proteolysis in vivo or in vitro to produce the desired recombinant protein. Methods for introducing nucleotide sequences into plants and expressing the protein encoded therein, involving viral DNA or RNA molecules, are well known in the art. See, Porta et al. (1996) *Mol. Biotechnol.* 5:209-221; as well as U.S. Pat. Nos. 5,866,785; 5,889,190; 5,889,191 and 5,589,367.

Methods also are known in the art for the targeted insertion of a nucleic acid molecule or construct at a specific location in the plant genome. In some instances, insertion of the nucleic acid molecule or construct at a desired genomic location can be achieved by using a site-specific recombination system. See, Int'l Patent Application Publication Nos. WO 99/025821, WO 99/025854, WO 99/025840, WO 99/025855 and WO 99/025853.

Transformation techniques for monocots therefore are well known in the art and include direct gene uptake of exogenous nucleic acid molecules or constructs by protoplasts or cells (e.g., by PEG- or electroporation-mediated uptake, and particle bombardment into callus tissue). Transformation of monocots via *Agrobacterium* also has been described. See, Int'l Patent Application Publication No. WO 94/00977 and U.S. Pat. No. 5,591,616; see also, Christou et al. (1991) *Bio/Technology* 9:957-962; Datta et al. (1990) *Bio/Technology* 8:736-740; Fromm et al. (1990) *Biotechnology* 8:833-844; Gordon-Kamm et al. (1990) *Plant Cell* 2:603-618; Koziel et al. (1993) *Bio/Technology* 11:194-200; Murashige & Skoog (1962) *Physiologia Plantarum* 15:473-497; Shimamoto et al. (1989) *Nature* 338:274-276; Vasil et al. (1992) *Bio/Technology* 10:667-674; Vasil et al. (1993) *Bio/Technology* 11:1553-1558; Weeks et al. (1993) *Plant Physiol.* 102:1077-1084; and Zhang et al. (1988) *Plant Cell Rep.* 7:379-384; as well as EP Patent Application Nos. 0 292 435; 0 332 581 and 0 392 225; Int'l Patent Application Publication Nos. WO 93/07278 and WO 93/21335; and U.S. Pat. No. 7,102,057.

Transformation techniques for dicots also are well known in the art and include *Agrobacterium*-mediated techniques and techniques that do not require *Agrobacterium*. Non-*Agrobacterium*-mediated techniques include the direct uptake of exogenous nucleic acid molecules by protoplasts or cells (e.g., by PEG- or electroporation-mediated uptake, particle bombardment, or microinjection). See, Klein et al. (1987) *Nature* 327:70-73; Paszkowski et al. (1984) *EMBO J.* 3:2717-2722; Potrykus et al. (1985) *Mol. Gen. Genet.* 199:169-177; and Reich et al. (1986) *Bio/Technology* 4:1001-10041; as well as U.S. Pat. No. 7,102,057.

Plant cells that have been transformed can be grown into plants by methods well known in the art. See, McCormick et al. (1986) *Plant Cell Rep.* 5:81-84. These plants then can be grown, and either pollinated with the same transformed strain or different strains, and the resulting progeny having the desired phenotypic characteristic identified. Two or more generations can be grown to ensure that expression of the desired phenotypic characteristic is stably maintained and inherited, and then seeds harvested to ensure expression of the desired phenotypic characteristic has been achieved.

The present disclosure therefore provides methods of introducing into plants, plant parts and plant host cells the nucleic acid constructs described herein, for example, an expression cassette of the present disclosure, which encode a modified substrate protein of a pathogen-specific protease, where the substrate protein has a heterologous protease recognition sequence.

EXAMPLES

The disclosure will be more fully understood upon consideration of the following non-limiting examples, which are offered for purposes of illustration, not limitation.

Example 1

RPS5 Activation by AvrRpt2 when Transiently Co-Expressed with a Modified PBS1 Protein Containing an AvrRpt2 Cleavage Site Methods:
Transient Transformation:
PBS1$^{RCS2}$ (SEQ ID NO: 4; modified PBS1 containing an AvrRpt2 cleavage site) was inserted in a vector (pTA7002; Aoyama & Chua (1997), supra) containing a dexamethasone-inducible promoter as described in DeYoung et al. (2012), supra. This vector was transformed into *A. tumfaciens* strain GV3101(pMP90). RPS5 and AvrRpt2 genes also were inserted into pTA7002 (separate constructs) as described in DeYoung et al. (2012) and independently transformed into GV3101(pMP90). For use as controls, GV3101(pMP90) also was transformed with the empty vector pTA7002, and with pTA7002 containing the wild-type PBS1 gene, and with pTA7002 containing AvrPphB, creating a total of six strains (listed below).

To transiently express these genes in plants, the *Agrobacterium* strains were prepared as described in DeYoung et al. (2012), supra, mixed in equal ratios in the combinations shown in FIGS. 1A and 1B and injected into expanding leaves of 4-week-old *N. glutinosa* plants. Protein expression was induced by spraying leaves with 50 µM dexamethasone 40 hours after injection.

For evaluation of cell death, leaves were scored for visible collapse 24 hours after dexamethasone application. Electrolyte leakage (a quantitative indicator of cell death) was measured as described in DeYoung et al. (2012), supra.

Constructs (all in pTA7002):
1. Wild-type PBS1;
2. PBS1 with the AvrRpt2 Cleavage Site (PBS1$^{RCS2}$);
3. AvrRpt2;
4. AvrPphB;
5. RPS5; and
6. Empty Vector (pTA7002).

Figure 1:
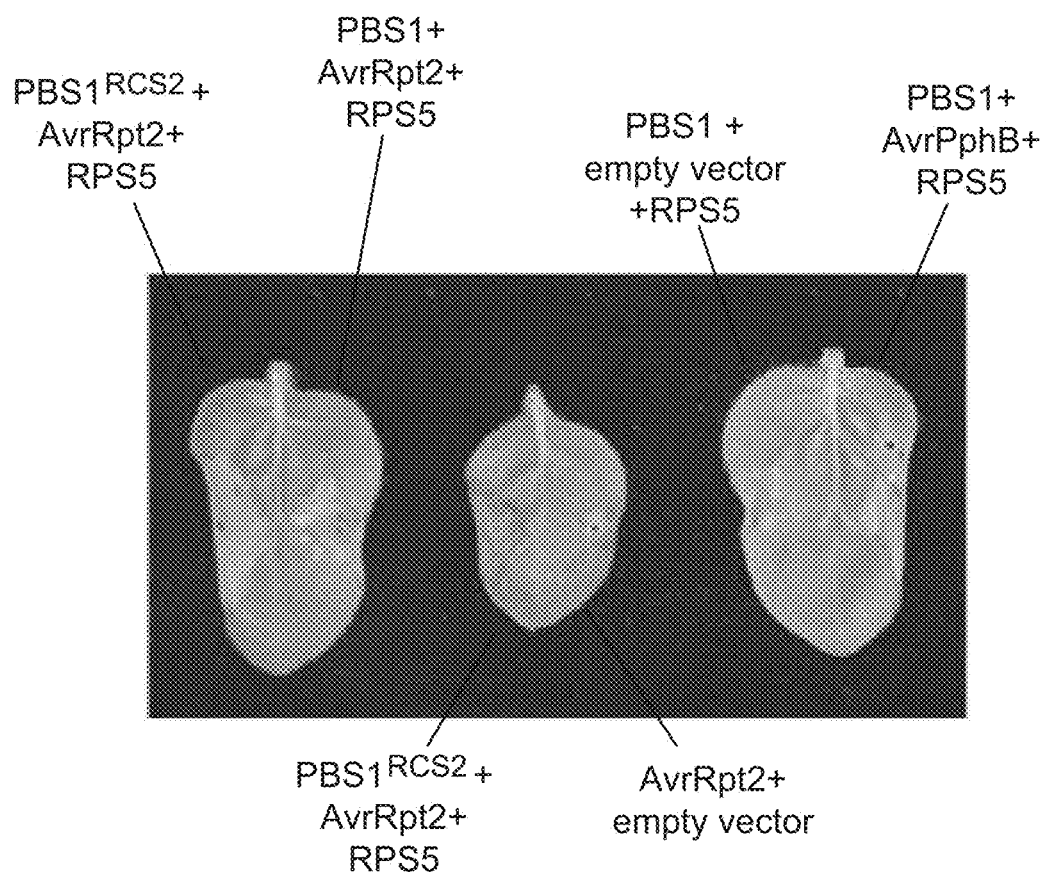

Results: As shown in FIG. 1, strong leaf collapse was induced when wild-type PBS1 was co-expressed with RPS5 and AvrPphB (far right side of figure). This is the positive control and demonstrated that *Arabidopsis* RPS5 can induce defense responses (cell death) when activated in *N. glutinosa*. Co-expression of wild-type PBS1 and RPS5 with AvrRpt2 did not induce significant collapse (left most leaf, right half), consistent with the inability of AvrRpt2 to cleave wild-type PBS1.

Figure 2:
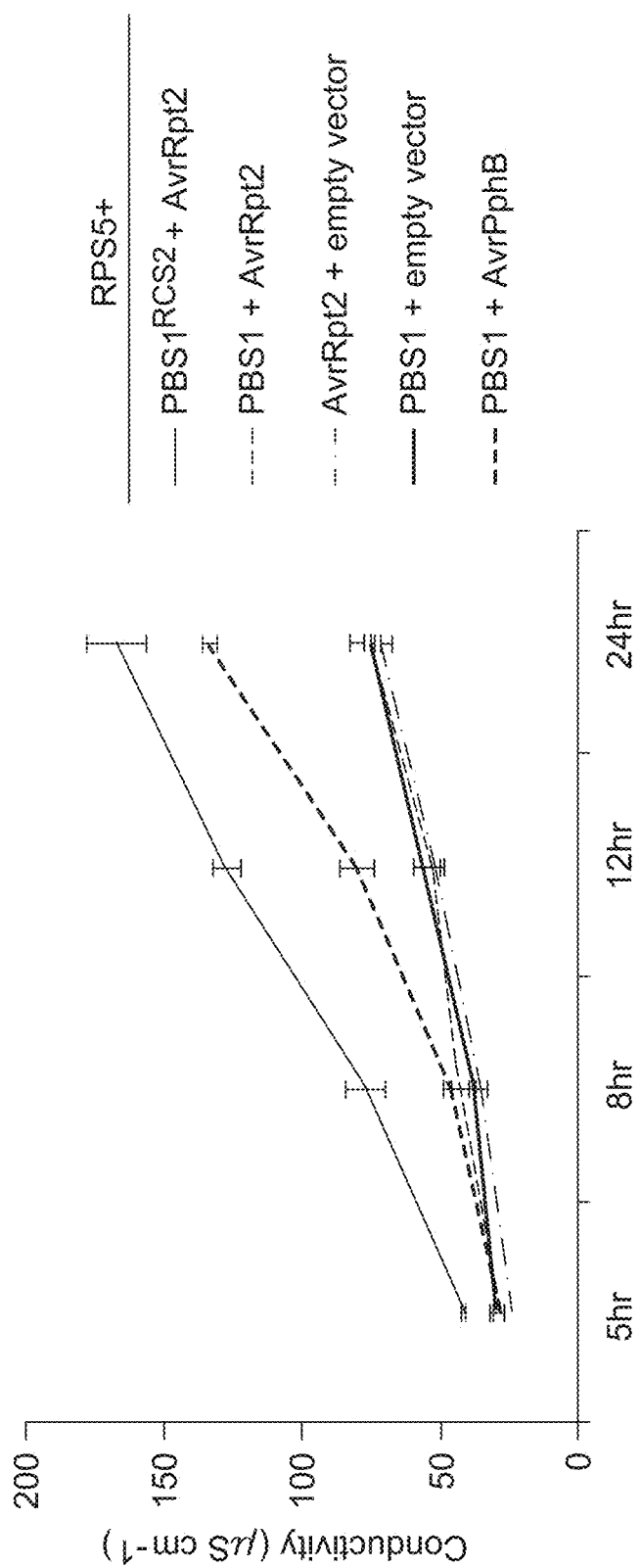

In contrast, co-expression of PBS1$^{RCS2}$ with RPS5 and AvrRpt2 induced strong leaf collapse, demonstrating that RPS5 can be activated by PBS1$^{RCS2}$ cleavage. FIG. 2 quantifies the level of cell death in each treatment, and is consistent with the visual symptoms shown in FIG. 1.

This example therefore shows that the AvrPphB cleavage site within the PBS1 activation loop can be replaced with the recognition sequence for a different protease from *P. syringae* named AvrRpt2. This replacement makes PBS1 a substrate protein for AvrRpt2 instead of AvrPphB. As such, co-expression of the modified PBS1 with AvrRpt2 and RPS5 resulted in activation of RPS5, whereas co-expression of wild-type PBS1 with AvrRpt2 and RPS5 did not.

Example 2

Transformation of *A. thaliana* with Modified PBS1 Protein Containing an AvrRpt2 Cleavage Site Confers Resistance to *P. syringae* Strains Expressing AvrRpt2

Methods:
Stable Transformation:
An *A. thaliana* mutant line containing mutations in the RPS2 and RIN4 genes (makes *A. thaliana* susceptible to infection by *P. syringae* expressing AvrRpt2) was stably transformed with a PBS1$^{RCS2}$ construct using *A. tumefaciens* strain GV3101(pMP90) following the protocol of Clough &

Bent using resistance to the herbicide glufosinate as a selectable marker. See, Clough & Bent (1998) *Plant J.* 16:735-743. Five independent transgenic plants were selected. Leaves of these individual plants were inoculated with *P. syringae* strain DC3000 expressing AvrRpt2 at a concentration of 0.5×10⁷ colony forming units (cfu) per milliliter using a needleless 1 mL syringe. Leaves were scored for visible leaf collapse (cell death) 24 hours after injection. Wild-type *A. thaliana* was used as a positive control.

Figure 3:
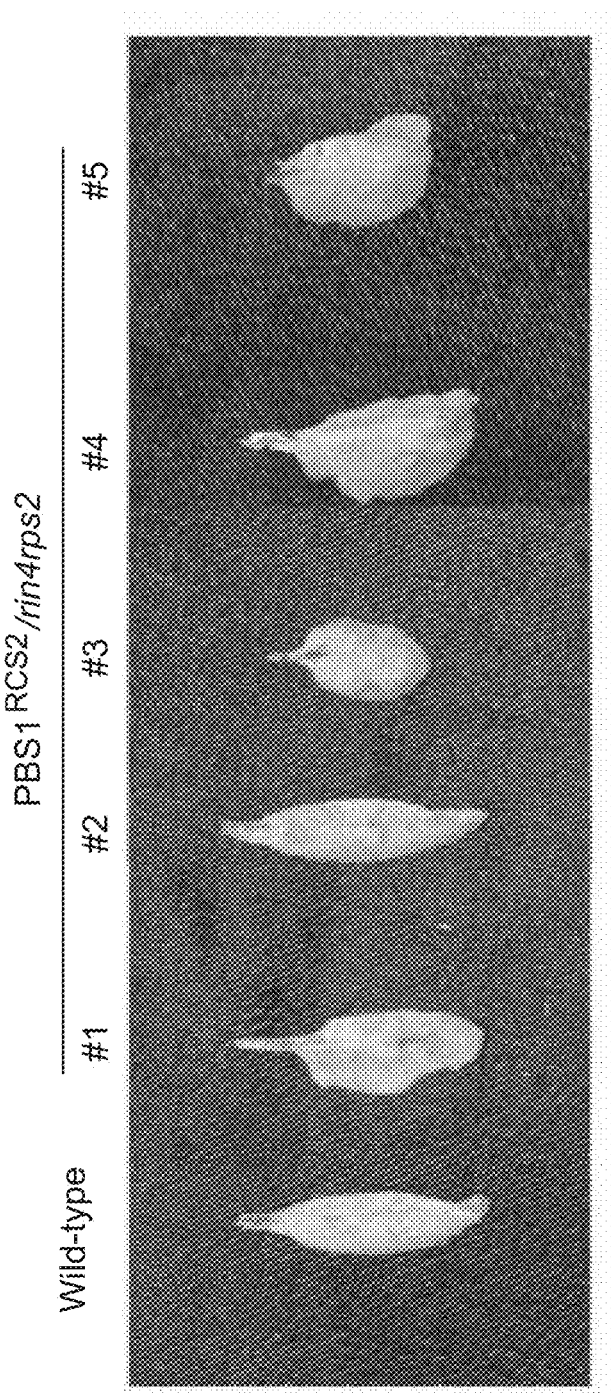

Results: As shown in FIG. 3, transgenic lines 1, 2, 4 and 5 showed leaf collapse on the right side in response to inoculation with *P. syringae* strain DC3000(AvrRpt2), which is indicative of programmed cell death activated by RPS5 in response to AvrRpt2. Line 3 did not show leaf collapse, likely due to failure of the PBS1$^{RCS2}$ transgene to express. This lack of leaf collapse demonstrates that the parent rin4rps2 mutant line does not induce cell death at this time point in response to inoculation with DC3000(AvrRpt2), which has been reported previously by Day et al. See, Day et al. (2005) Plant Cell 17:1292-1305. Activation of cell death indicates that transgenic lines 1, 2, 4 and 5 have gained disease resistance to DC3000(AvrRpt2); thus, expression of PBS1$^{RCS2}$ enables the endogenous RPS5 gene of *Arabidopsis* to confer resistance to this strain.

Example 3 (Prophetic)

RPS5 Activation by a Protease (BEC1019) from a Powdery Mildew Fungus when Co-Expressed with a Modified PBS1 Protein Containing a BEC1019 Cleavage Site.

The genome sequences of several different species of powdery mildew fungi, including species that infect wheat and barley (*Blumeria graminis*) and species that infect *Arabidopsis* (*Golovinomyces cichoracearum* and *G. orontii*) have been determined. These genomes have been analyzed for the presence of protease enzymes that are likely secreted during infection of host plants. One such protease that is conserved among these fungal species has been identified and has been named BEC1019. Silencing of the BEC1019 gene has been shown to compromise virulence of barley powdery mildew, indicating that this protease is required to cause disease, at least on barley ((Pliego, C., Nowara, D., Bonciani, G., Gheorghe, D. M., Xu, R., Surana, P., Whigham, E., Nettleton, D., Bogdanove, A. J., Wise, R. P., Schweizer, P., Bindschedler, L. V., and Spanu, P. D. 2013. Host-induced gene silencing in barley powdery mildew reveals a class of ribonuclease-like effectors. Mol Plant Microbe Interact 26:633-642).

A nucleic acid molecule for the protease recognition sequence for BEC1019 will be inserted into the activation loop of PBS1. The modified PBS1 nucleic acid molecule then will be transformed into *Arabidopsis* plants lacking a functional PBS1 gene, but that are wild-type for RPS5. The *Arabidopsis* plants should become resistant to infection by powdery mildew species such as *G. cichoracearum* and *G. golovinomyces*. If this is confirmed, RPS5 and PBS1 containing the BEC1019 cleavage site will be transformed into various crop plants to confer resistance to powdery mildew (e.g., wheat, barley, grapevine, etc.).

Example 4 (Prophetic)

RPS5 Activation by Tobacco Etch Virus (TEV) Protease when Co-Expressed with a Modified PBS1 Protein Containing a TEV Polyprotein Cleavage Site.

Several viruses that infect plants encode proteases that are required for processing of viral polyproteins. A nucleic acid molecule encoding the protease recognition sequence for TEV protease will be inserted into the activation loop of PBS1. The modified PBS1 and wild-type RPS5 nucleic acid molecules will be used to transform the tobacco relative *Nicotiana benthamiana*. Activation of RPS5 by TEV protease will first be tested using the transient expression system described in Example 1. Assuming that RPS5 is activated, as predicted, the modified PBS1 gene and RPS5 will be transformed into *N. tabacum* and the resulting transgenic plants are tested for resistance to TEV infection. This gene pair should confer resistance.

Example 5

RPS5 Activation by AvrRpt2 when Transiently Co-Expressed with a Modified PBS1 Protein Containing an AvrRpt2 Cleavage Site.

Methods:

Construction of plasmids for transgene expression. A PBS1::RCS2 entry clone harboring the RIN4 cleavage site sequence inserted at the AvrPphB cleavage site was constructed using overlap PCR and a pBSDONR PBS1 template. A Multisite Gateway LR Clonase reaction was performed to recombine the entry clone, the pBAV154 destination vector (carrying a dexamethasone-inducible promoter) and a clone containing a 3×HA C-terminal epitope. The PBS1$^{RCS2}$ and PBS1$^{TCS}$ entry clones in which the AvrPphB cleavage site of PBS1 was replaced with the RIN4 cleavage site 2 (RCS2) and TEV cleavage site (TCS), respectively, were created from the pBSDONR PBS1 template using site-directed mutagenesis PCR. These entry clones and 3×HA were recombined into the pTA7002 destination vector (carrying a dexamethasone-inducible promoter) using LR reactions. The coding regions of AvrPphB, AvrRpt2, C122A (AvrRpt2 mutant), and TEV protease were PCR-amplified and cloned into the Gateway vector pBSDONR P1-P4 using Gateway BP Clonase to generate entry clones, which were recombined with pTA7002 and 5×Myc using LR reactions. To generate plant expression constructs for PBS1$^{RCS2}$ fused to 3×HA driven by the native PBS1 regulatory elements (pPBS1-PBS1$^{RCS}$-HA), an 875 bp ApaI/XhoI fragment spanning the PBS1 promoter and a 400 bp NotI/SacI fragment spanning the PBS1 terminator, and a 1731 bp XhoI/XbaI fragment containing the Gateway cassette were inserted into the pGreen0229 binary vector. PBS1$^{RCS2}$ and 3×HA were then recombined into this destination construct using LR clonase. All constructs were verified by sequencing. Primer sequences used in cloning are listed in Table 4 below.

TABLE 4

Primer Sequences.

| Primer Name | Sequence (5' → 3') (SEQ ID NO:) | Purpose |
|---|---|---|
| SHP5 | GTGCCTAAATTCGGTGACTGGTCTCATGTCTCCA CTAGAGT (SEQ ID NO: 11) | PBS1::RCS2 |

TABLE 4-continued

Primer Sequences.

| Primer Name | Sequence (5' → 3')(SEQ ID NO:) | Purpose |
|---|---|---|
| SHP6 | CCAGTCACCGAATTTAGGCACTTTGTCTCCCGTT GGTCC (SEQ ID NO: 12) | PBS1::RCS2 |
| SHP28 | GTGCCTAAATTCGGTGACTGGACTAGAGTTATGG GAACTTATGGT (SEQ ID NO: 13) | PBS1$^{RCS2}$ |
| SHP29 | CCAGTCACCGAATTTAGGCACCGTTGGTCCGAGT TTAGCAA (SEQ ID NO: 14) | PBS1$^{RCS2}$ |
| SHP59 | GAAAACCTGTATTTTCAGGGCACTAGAGTTATGG GAACTTATGGT (SEQ ID NO: 15) | PBS1$^{TCS}$ |
| SHP60 | GCCCTGAAAATACAGGTTTTCCGTTGGTCCGAGT TTAGCAA (SEQ ID NO: 16) | PBS1$^{TCS}$ |
| SHP61 | GGACAAGTTTGTACAAAAAAGCAGGCTCTATGGA AAGCTTGTTTAAGGGG (SEQ ID NO: 17) | TEV protease |
| SHP62 | GGACAACTTTGTATAGAAAAGTTGGGTGATTCAT GAGTTGAGTCGCTTC (SEQ ID NO: 18) | TEV protease |
| SHP15 | GGACAAGTTTGTACAAAAAAGCAGGCTCTATGAA AATTGCTCCAGTTGCCA (SEQ ID NO: 19) | AvrRpt2 or C122A |
| SHP16 | GGACAACTTTGTATAGAAAAGTTGGGTGGCGGTA GAGCATTGCGTGTGG (SEQ ID NO: 20) | AvrRpt2 or C122A |
| RB63 | GGGGACAAGTTTGTACAAAAAAGCAGGCTGCATG GGGTGTGCATCCTCTTCAGG (SEQ ID NO: 21) | AvrPphB |
| RB62 | GGGGACAACTTTGTATAGAAAAGTTGGGTGCGAA ACTCTAAACTCGTTTA (SEQ ID NO: 22) | AvrPphB |
| BD113 | AGGGCCCATAGTTTCGTTCTCTGCTTCAAG (SEQ ID NO: 23) | PBS1 promoter |
| BD115 | ACTCGAGCTCCTCCTTTACTCAATTTTC (SEQ ID NO: 24) | PBS1 promoter |
| BD131 | AGCGGCCGCAACCGGTTTGGGTCGGTCTTG (SEQ ID NO: 25) | PBS1 terminator |
| BD119 | AGAGCTCCATGTGACCCACGTTGTCCGA (SEQ ID NO: 26) | PBS1 terminator |

Plant materials and growth conditions. *Arabidopsis thaliana*, *Nicotina benthamiana*, and *N. glutinosa* plants were grown under a 9 h light/15 h dark cycle at 24° C. in Metro-Mix 360 plotting mixture (Sun Gro Horticulture, www.sungrow.com). Transfer-DNA insertion lines of PBS1 (pbs1-7; Salk_062464C) and RPS5 (rps5-3; Salk_015294C) were obtained from the Salk T-DNA Express collection via the *Arabidopsis* Biological Resource Center at Ohio State University.

Assessing resistance to bacterial infection in *Arabidopsis*. For hypersensitive response (HR) assays, *Pseudomonas syringae* strains DC3000(avrPphB) and DC3000(avrRpt2) were grown on King's medium B agar plates, and infiltrated into 5-week old *Arabidopsis* leaves using needless syringe at $10^8$ colony-forming units (cfu) per ml (OD$_{600}$=0.1). Leaves were scored and photographed 21 hours after inoculation. To measure bacterial growth within plant leaves, 5-week-old *Arabidopsis* plants were infiltrated with DC3000(avrRpt2) at $10^5$ cfu per ml. A total of 0.5 cm$^2$ of leaf tissue, collected using a cork borer, was ground in 10 mM MgCl$_2$ and plated by serial dilution on selective medium (King's medium B supplemented with 100 µg/mL rifampicin and 50 µg/mL kanamycin) in four replicates at the indicated time points.

Transient expression assays in *Nicotiana* species. For transient expression assays, the dexamethasone-inducible constructs described above were mobilized into *Agrobacterium tumefaciens* strain GV3101. After overnight culture in liquid LB media, bacterial cells were pelleted and resuspended in 10 mM MgCl$_2$ with 100 µM acetosyringone (Sigma-Aldrich), adjusted to an OD$_{600}$ of 0.1, incubated for 2 hours at room temperature and infiltrated into leaves of 4-week-old *N. benthamiana* or *N. glutinosa* plants. Leaves were sprayed with 50 µM dexamethasone 40 hours after injection. Samples were harvested for protein extraction 6 or 24 hours after dexamethasone application, and HR was evaluated 24 hours after dexamethasone application.

Electrolyte leakage assays. To measure electrolyte leakage from *Agrobacterium*-infiltrated *Nicotiana* leaves, 8 leaf discs (6 mm in diameter) were collected from four individual leaves at 2 hours post dexamethasone induction. After washing three times with distilled water, the leaf discs were floated in 5 ml of distilled water containing 0.001% Tween 20 (Sigma-Aldrich). Conductivity was monitored in four replicates at the indicated time points using a Traceable Pen Conductivity Meter (VWR).

Immunoblot analysis. *Nicotiana* leaf tissue expressing a protein of interest was ground in extraction buffer (150 mM NaCl, 50 mM Tris [pH 7.5], 0.2% Nonidet P-40 [Sigma-Aldrich], 1% plant protease inhibitor cocktail [Sigma-Aldrich]). Cell debris was pelleted at 12,000 rpm for 10 min., and the collected supernatants were separated on a 4-20% gradient Tris-Hepes-SDS polyacrylamide gel (Thermo Scientific). Proteins were detected with 1:2000 diluted peroxidase-conjugated anti-HA antibody (Sigma-Aldrich) or with 1:4000 diluted peroxidase-conjugated anti-c-Myc antibody (Roche). Total protein from transgenic *Arabidopsis* tissue expressing pDEX-PBS1::RCS2-HA was prepared 16 hours post dexamethasone induction, and subjected to immunoblot analysis. Total protein from transgenic *Arabidopsis* tissue expressing pPBS1-PBS1$^{RCS2}$-HA was prepared from healthy plants, or 12 hours post inoculation with DC3000 (e.v.) or DC3000(avrRpt2) at a density of $10^8$ cfu/ml, and immunoprecipitated using Pierce Anti-HA agarose (Thermo Scientific) for immunoblot analysis.

Figure 4:
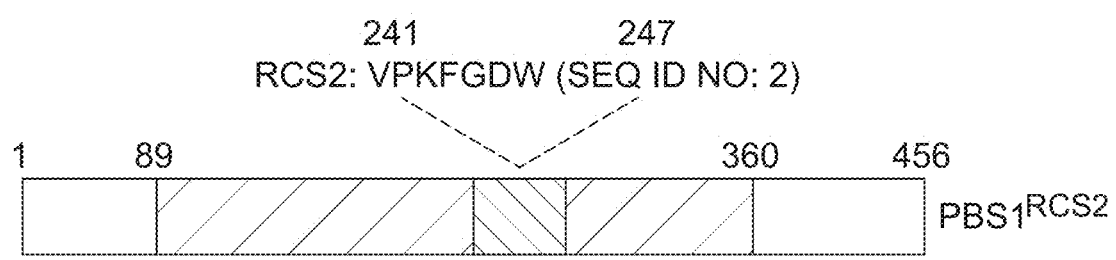
FIG. 4 is a schematic representation of a PBS1$^{RCS2}$ construct illustrating the replacement of the AvrPphB cleavage site within the PBS1 activation loop with the RIN4 cleavage site 2 (RCS2) as discussed in Example 5.
Figure 5:
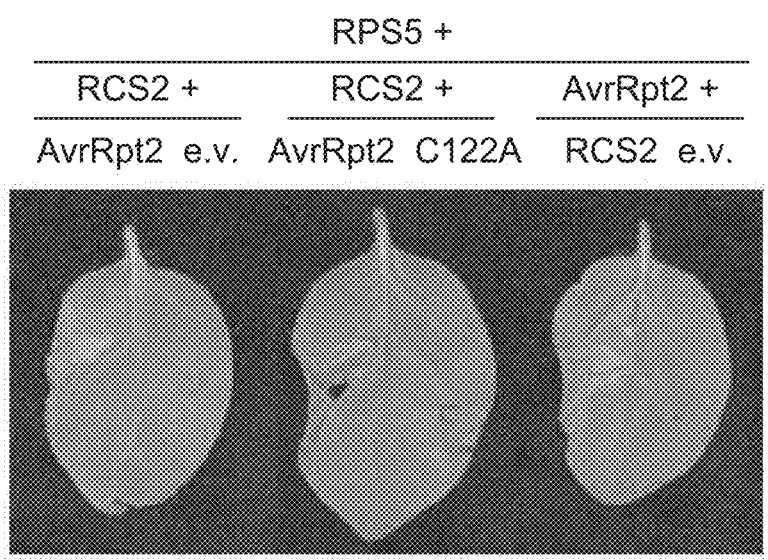
FIG. 5 is a photograph taken 24 hours post-induction showing that the co-expression of PBS1$^{RCS2}$ with AvrRpt2 and PRS5 induced an RPS5-dependent cell death response, whereas cell death was not detected in the absence of AvrRpt2 or PBS1$^{RCS2}$ as discussed in Example 5.
Figure 6:
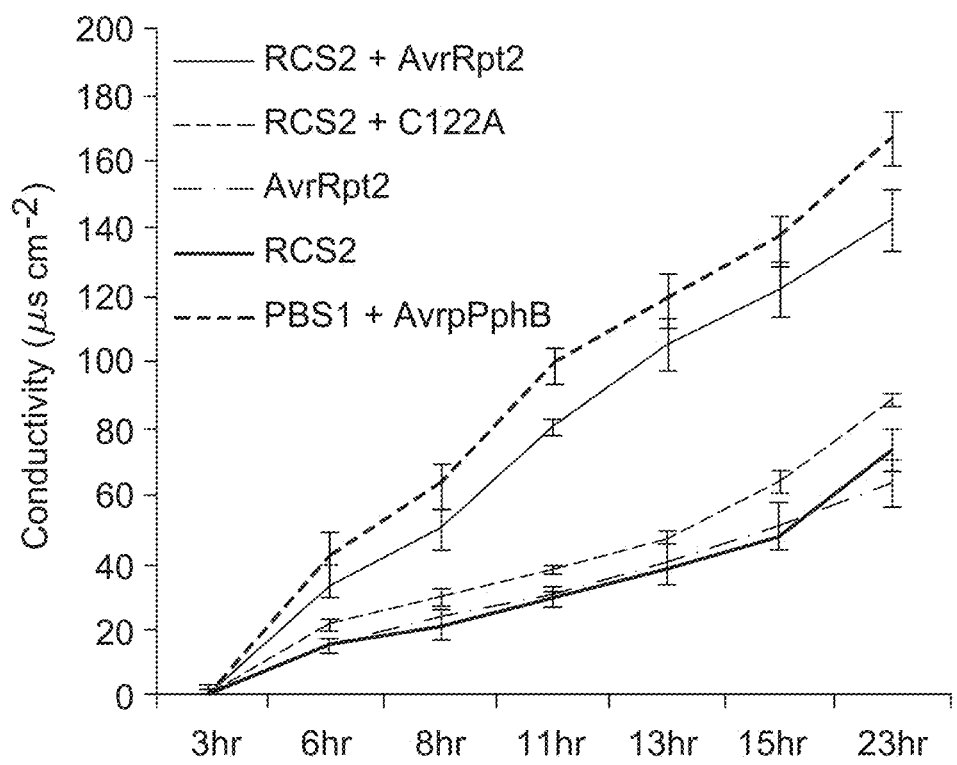
FIG. 6 is a graph illustrating that PBS1$^{RCS2}$ with AvrRpt2 induced as much electrolyte leakage as wild-type PBS1 cleaved by AvrPphB, whereas PBS1$^{RCS2}$ with C122A only weakly activated RPS5 as discussed in Example 5. Data represents the mean and standard deviation (n=4).
Figure 7:
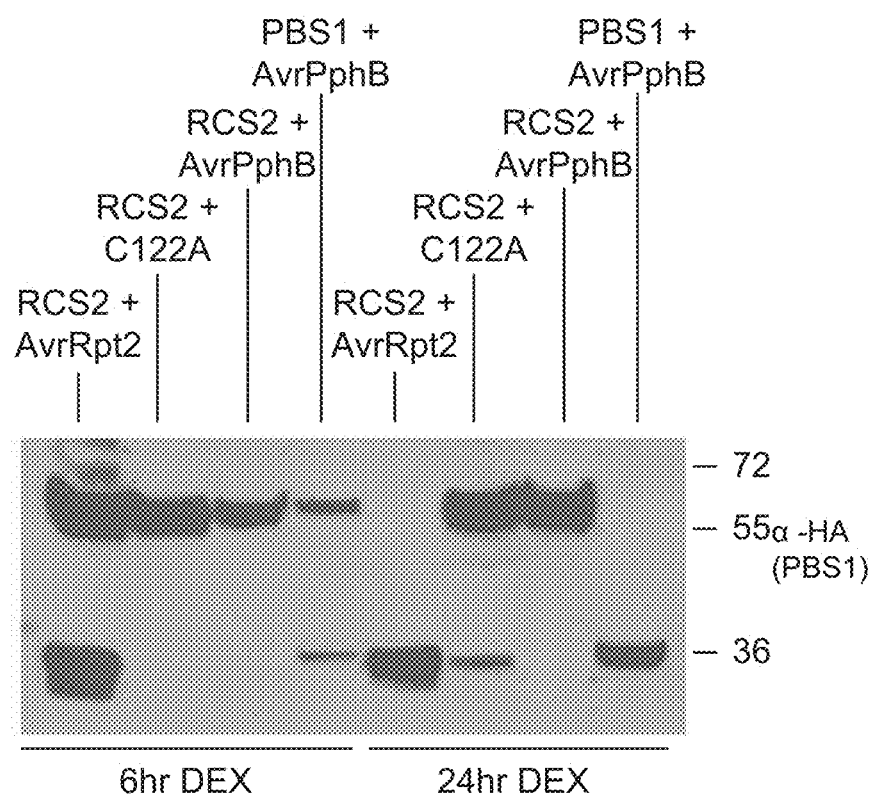
FIG. 7 is an immunoblot confirming that AvrRpt2 cleaved PBS1$^{RCS2}$ at 6 hours post-induction, whereas C122A or AvrPphB did not as discussed in Example 5.

Results: As illustrated in FIG. 4, seven amino acids flanking the AvrPphB cleavage site in PBS1 (GDKSHVS; SEQ ID NO:1) were replaced with the RIN4 cleavage site 2 (RCS2) sequence (VPKFGDW; SEQ ID NO:2). Co-expression of the PBS1$^{RCS2}$ with AvrRpt2 and PRS5 induced an RPS5-dependent cell death response, whereas cell death was not detected in the absence of AvrRpt2 or PBS1$^{RCS2}$ (FIG. 5). A protease-deficient mutant form of AvrRpt2 (C122A) induced only a very weak macroscopic response. To quantify the HR, electrolyte leakage analysis was performed as a measurement of cell death. Consistent with the macroscopic symptoms, PBS1$^{RCS2}$ with AvrRpt2 induced as much electrolyte leakage as wild-type PBS1 cleaved by AvrPphB, whereas PBS1$^{RCS2}$ with C122A only weakly activated RPS5 (FIG. 6). Immunoblot analysis confirmed that AvrRpt2 cleaved PBS1$^{RCS2}$ at 6 hours post-induction, whereas C122A or AvrPphB did not (FIG. 7). At 24 hours post-induction, AvrRpt2-induced cleavage was increased, and even C122A induced small amounts of cleavage (FIG. 7), consistent with the observed weak induction of cell death by this construct (FIGS. 5 and 6). Together, these data establish that PBS1$^{RCS2}$ is a substrate for AvrRpt2 and that AvrRpt2-mediated cleavage activates RPS5.

To assess whether AvrRpt2-mediated cleavage of PBS1$^{RCS2}$ can activate RPS5 expressed at native levels in *Arabidopsis*, an *Arabidopsis* rin4rps2 mutant was stably transformed with PBS1$^{RCS2}$ under the native PBS1 regulatory elements (pPBS1-PBS1$^{RCS2}$-HA/rin4rps2). The rin4rps2 mutant was used to avoid activation of the endogenous RPS2 disease resistance protein by AvrRpt2. As shown in FIG. 8, two independent transgenic lines (#5 and #2) showed a visible HR 21 hours after inoculation with *P. syringae* strain DC3000(avrRpt2), whereas the untransformed rin4rps2 mutant did not. In planta bacterial growth assays showed that growth of DC3000(avrRpt2) in transgenic lines #5 and #2 was restricted to levels 100- to 200-fold less compared to rin4rps2, while transgenic lines #1 and #3 had approximately 5-10 fold lower bacterial growth than rin4rps2 (FIG. 9; statistically significant differences were determined by a two-tailed Student's t-Test ($P<0.01$) or a one-way ANOVA and Tukey's HSD ($P<0.01$)). Restriction of bacterial growth correlated with expression levels of PBS1$^{RCS2}$ (FIG. 10). Proteins from transgenic lines shown in FIG. 8 were immunoprecipitated with anti-HA agarose, and immunoblots were performed with an anti-HA antibody. In addition, a cleavage product of PBS1$^{RCS2}$ was detected in transgenic line #5 twelve hours after inoculation with DC3000(avrRpt2), but not with DC3000 lacking avrRpt2 (DC3000(e.v.); FIG. 11), indicating that cleavage of PBS1$^{RCS2}$ by AvrRpt2 activates RPS5 in *Arabidopsis*. In addition, these transgenic plants also displayed HR 21 hours after injection with DC3000(avrPphB), demonstrating that native recognition specificity of RPS5 was retained in these transgenic lines (FIG. 12). Thus, RPS5-mediated disease resistance can be activated by two different protease effector proteins in the PBS1$^{RCS2}$ transgenic plants, demonstrating that the recognition specificity of RPS5 can be expanded by addition of new 'decoy' copies of PBS1.

To test whether this decoy approach could be extended to recognize pathogens beyond *P. syringae*, a PBS1 decoy was created that can be cleaved by the NIa protease of Tobacco Etch Virus (referred to as PBS1$^{TCS}$) (FIG. 13). TEV is a positive stranded RNA virus that encodes a polyprotein that must be post-translationally processed by its embedded NIa protease. This protease is essential for viral replication, thus an R protein that is triggered by its enzymatic activity should be highly durable, as it would be extremely difficult for the virus to simultaneously change the specificity of its protease and the protease cleavage sites embedded within its polyprotein.

TEV protease and RPS5 were transiently co-expressed with PBS1$^{TCS}$ in *N. benthamiana* (FIG. 14). RPS5-mediated cell death was induced only when RPS5 was co-expressed with PBS1$^{TCS}$ and TEV protease, but was not induced when either PBS1$^{TCS}$ or TEV protease was excluded (FIG. 15). Quantification of cell death using electrolyte leakage showed that PBS1$^{TCS}$ and TEV protease induced RPS5-mediated cell death equivalent to wild-type PBS1 and AvrPphB (FIG. 16). Immunoblot analysis confirmed that TEV protease cleaved PBS1$^{TCS}$ 6 hours post induction, whereas AvrPphB did not. Also, TEV protease did not cleave wild-type PBS1. These data established that PBS1 can be engineered to function as a decoy to detect the presence of proteases from two very different classes of pathogen, viruses and bacteria, and open the way to engineering resistance to a broad array of pathogens.

Example 6

Recognition of AvrPphB by Soybean.

In this Example, *P. syringae* pv. *glycinea* Race4 strains carrying AvrPphB or AvrB::Ω (a non-functional effector used as an empty vector control) were infiltrated into a unifoliolate leaf of soybean cultivar Flambeau. The leaf was removed from the plant 24 hours after injection, cleared using hot 70% ethanol and photographed.

Soybean responded to *P. syringae* expressing AvrPphB with an HR as indicated by leaf browning (dark region shown in FIG. 17). These data indicated that using the decoy approach described herein to engineer resistance in crop plants might not require transfer of the *Arabidopsis* RPS5 gene if crop plants already possess the ability to detect AvrPphB by a similar mechanism. In addition, PBS1 is highly conserved among crop plants, including soybean. It may thus be possible to engineer soybean, and other crop plants, to detect various pathogen proteases by making small changes to their endogenous PBS1 genes.

All of the patents, patent applications, patent application publications and other publications recited herein are hereby incorporated by reference as if set forth in their entirety.

The present disclosure has been described in connection with what are presently considered to be the most practical and preferred embodiments. However, the present disclosure has been presented by way of illustration and is not intended to be limited to the disclosed embodiments. Accordingly, one of skill in the art will realize that the present disclosure is intended to encompass all modifications and alternative arrangements of the compositions and methods as set forth in the appended claims.

What is claimed is:

1. A recombinant nucleic acid molecule comprising a heterologous promoter operably linked to a nucleotide sequence that encodes at least one substrate protein of a plant pathogen-specific protease expressed by the plant pathogen having a heterologous pathogen-specific protease recognition sequence, wherein the substrate protein is *Arabidopsis thaliana* AvrPphB susceptible 1 (PBS1), and wherein the endogenous AvrPphB cleavage site of SEQ ID NO:1 is replaced with a heterologous pathogen-specific protease recognition sequence selected from the group consisting of VPKFGDW (SEQ ID NO:2), OEHGCOL (SEP ID NO: 3), ENLYFOG (SEP ID NO: 4), EPVSTOG (SEP ID NO: 27) and PYVOAOS (SEP ID NO:28).

2. The recombinant nucleic acid molecule of claim 1, wherein the heterologous pathogen-specific protease recognition sequence is located between about amino acid position 240 to about amino acid position 250 in reference to SEQ ID NO:6 when the substrate protein is PBS1.

3. A modified substrate protein of a plant pathogen-specific protease expressed by the plant pathogen comprising an amino acid sequence having a heterologous protease recognition sequence, wherein the modified substrate protein is encoded by the recombinant nucleic acid molecule according to claim 1.

4. A vector comprising the recombinant nucleic acid molecule according to claim 1.

5. A transformed plant cell comprising the recombinant nucleic acid molecule according to claim 1.

6. The transformed plant cell of claim 5, wherein the plant cell is from a plant selected from the group consisting of a monocot and a dicot.

7. A transformed plant comprising the recombinant nucleic acid molecule according to claim 1.

8. The transformed plant of claim 7, wherein the plant is selected from the group consisting of a monocot and a dicot.

9. A transgenic seed of the transformed plant according to claim 7.

10. A method of protecting a plant from infection by a plant pathogen that secretes at least one specific protease, the method comprising the step of:

introducing to the plant a nucleotide sequence that encodes at least one substrate protein of a plant pathogen-specific protease secreted by the plant pathogen having a heterologous pathogen-specific protease recognition sequence within the substrate protein, wherein the substrate protein is *Arabidopsis thaliana* AvrPphB susceptible 1 (PBS1), and wherein the endogenous AvrPphB cleavage site of SEQ ID NO:1 is replaced with a heterologous pathogen-specific protease recognition sequence selected from the group consisting of VPKFGDW (SEQ ID NO:2), QEHGCQL (SEQ ID NO:3), ENLYFQG (SEQ ID NO:4), EPVSTQG (SEQ ID NO:27) and PVVQAQS (SEQ ID NO:28).

* * * * *

SEQUENCE LISTING

```
<160> NUMBER OF SEQ ID NOS: 28

<210> SEQ ID NO 1
<211> LENGTH: 7
<212> TYPE: PRT
<213> ORGANISM: Pseudomonas syringae

<400> SEQUENCE: 1

Gly Asp Lys Ser His Val Ser
1               5

<210> SEQ ID NO 2
<211> LENGTH: 7
<212> TYPE: PRT
<213> ORGANISM: Pseudomonas syringae

<400> SEQUENCE: 2

Val Pro Lys Phe Gly Asp Trp
1               5

<210> SEQ ID NO 3
<211> LENGTH: 7
<212> TYPE: PRT
<213> ORGANISM: Pseudomonas syringae

<400> SEQUENCE: 3

Gln Glu His Gly Cys Gln Leu
1               5

<210> SEQ ID NO 4
<211> LENGTH: 7
<212> TYPE: PRT
<213> ORGANISM: Tobacco etch virus

<400> SEQUENCE: 4

Glu Asn Leu Tyr Phe Gln Gly
1               5

<210> SEQ ID NO 5
<211> LENGTH: 1371
<212> TYPE: DNA
<213> ORGANISM: Artificial Sequence
<220> FEATURE:
<223> OTHER INFORMATION: Synthetic

<400> SEQUENCE: 5
atgggttgtt tctcgtgttt tgattcgagt gatgacgaga agctgaatcc agttgatgaa      60
tctaatcatg gtcagaagaa acaatcacaa ccgacagtat ccaataacat atctggactc     120
ccttcaggtg gggagaagct tagctcaaag accaatggag gatcaaaaag ggagctactg     180
cttccaaggg atggacttgg acaaattgct gctcatacat ttgctttccg cgagcttgct     240
gctgcaacta tgaactttca tcctgacact ttcttaggcg aagtggatt tggacgtgtc     300 tacaaaggaa ggcttgacag caccggtcag gttgttgctg ttaaacaact agacaggaat     360
ggtctacaag gtaacagaga atttctggta gaggttctta tgctcagtct tcttcatcat     420
cccaacttag tcaaccttat tggttattgt gctgatggag atcaacgcct cttggtctac     480
```

```
gagtttatgc cgttaggatc attggaagat cacctccacg atcttccacc ggataaggag      540
gccttagatt ggaacatgag aatgaaaata gctgctggtg cggcgaaagg attggaattt      600
ctacatgata aggcaaaccc tccggttatt tatagagatt ttaagtcatc aaatatttta      660
ctggatgagg gttccaccc taagcttcct gattttggac ttgctaaact cggaccaacg       720
gtgcctaaat tcggtgactg gactagagtt atgggaactt atggttattg tgctcccgag      780
tacgcaatga cgggacaatt gacagtaaaa tcagatgtct acagttttgg tgtggttttt      840
ctcgagctca ttactggtcg caaagctata gacagcgaga tgcctcatgg agagcagaac      900
ctggtggctt gggctcgccc attgttcaac gacaggcgaa agttcataaa actggctgat      960
ccaaggttaa agggcggttt ccaacgcgt gcactctacc aagctttagc tgtggcatca      1020
atgtgcatcc aagaacaggc ggctacacgt cctctcatag cagatgttgt cactgcactc     1080
tcctatcttg caaaccaagc ttatgatcca agtaaagatg atagtagaag aaaccgggat     1140
gaaagaggtg caaggttaat aacaaggaac gacgatggag gtggctcggg aagtaaattc     1200
gatttagaag gttcagagaa agaagattca ccgagagaga cagctcggat attgaaccga     1260
gatatcaata gggagcgtgc ggttgcagag gctaagatgt gggagagag tttgagggag      1320 aaacgaagac agagcgagca gggtacttca gagagcaaca gtaccgggta g              1371
```

<210> SEQ ID NO 6
<211> LENGTH: 456
<212> TYPE: PRT
<213> ORGANISM: Artificial Sequence
<220> FEATURE:
<223> OTHER INFORMATION: Synthetic

<400> SEQUENCE: 6

```
Met Gly Cys Phe Ser Cys Phe Asp Ser Ser Asp Glu Lys Leu Asn
1               5                   10                  15

Pro Val Asp Glu Ser Asn His Gly Gln Lys Lys Gln Ser Gln Pro Thr
            20                  25                  30

Val Ser Asn Asn Ile Ser Gly Leu Pro Ser Gly Gly Glu Lys Leu Ser
        35                  40                  45

Ser Lys Thr Asn Gly Gly Ser Lys Arg Glu Leu Leu Leu Pro Arg Asp
    50                  55                  60

Gly Leu Gly Gln Ile Ala Ala His Thr Phe Ala Phe Arg Glu Leu Ala
65                  70                  75                  80

Ala Ala Thr Met Asn Phe His Pro Asp Thr Phe Leu Gly Glu Gly Gly
                85                  90                  95

Phe Gly Arg Val Tyr Lys Gly Arg Leu Asp Ser Thr Gly Gln Val Val
            100                 105                 110

Ala Val Lys Gln Leu Asp Arg Asn Gly Leu Gln Gly Asn Arg Glu Phe
        115                 120                 125

Leu Val Glu Val Leu Met Leu Ser Leu His His Pro Asn Leu Val
    130                 135                 140

Asn Leu Ile Gly Tyr Cys Ala Asp Gly Asp Gln Arg Leu Leu Val Tyr
145                 150                 155                 160

Glu Phe Met Pro Leu Gly Ser Leu Glu Asp His Leu His Asp Leu Pro
                165                 170                 175

Pro Asp Lys Glu Ala Leu Asp Trp Asn Met Arg Met Lys Ile Ala Ala
            180                 185                 190

Gly Ala Ala Lys Gly Leu Glu Phe Leu His Asp Lys Ala Asn Pro Pro
        195                 200                 205
```

```
Val Ile Tyr Arg Asp Phe Lys Ser Ser Asn Ile Leu Leu Asp Glu Gly
            210                 215                 220

Phe His Pro Lys Leu Ser Asp Phe Gly Leu Ala Lys Leu Gly Pro Thr
225                 230                 235                 240

Val Pro Lys Phe Gly Asp Trp Thr Arg Val Met Gly Thr Tyr Gly Tyr
                245                 250                 255

Cys Ala Pro Glu Tyr Ala Met Thr Gly Gln Leu Thr Val Lys Ser Asp
                260                 265                 270

Val Tyr Ser Phe Gly Val Val Phe Leu Glu Leu Ile Thr Gly Arg Lys
            275                 280                 285

Ala Ile Asp Ser Glu Met Pro His Gly Glu Gln Asn Leu Val Ala Trp
290                 295                 300

Ala Arg Pro Leu Phe Asn Asp Arg Arg Lys Phe Ile Lys Leu Ala Asp
305                 310                 315                 320

Pro Arg Leu Lys Gly Arg Phe Pro Thr Arg Ala Leu Tyr Gln Ala Leu
                325                 330                 335

Ala Val Ala Ser Met Cys Ile Gln Glu Gln Ala Ala Thr Arg Pro Leu
                340                 345                 350

Ile Ala Asp Val Val Thr Ala Leu Ser Tyr Leu Ala Asn Gln Ala Tyr
            355                 360                 365

Asp Pro Ser Lys Asp Asp Ser Arg Arg Asn Arg Asp Glu Arg Gly Ala
370                 375                 380

Arg Leu Ile Thr Arg Asn Asp Asp Gly Gly Ser Gly Ser Lys Phe
385                 390                 395                 400

Asp Leu Glu Gly Ser Glu Lys Glu Asp Ser Pro Arg Glu Thr Ala Arg
                405                 410                 415

Ile Leu Asn Arg Asp Ile Asn Arg Glu Arg Ala Val Ala Glu Ala Lys
            420                 425                 430

Met Trp Gly Glu Ser Leu Arg Glu Lys Arg Gln Ser Glu Gln Gly
                435                 440                 445

Thr Ser Glu Ser Asn Ser Thr Gly
    450                 455

<210> SEQ ID NO 7
<211> LENGTH: 1371
<212> TYPE: DNA
<213> ORGANISM: Artificial Sequence
<220> FEATURE:
<223> OTHER INFORMATION: Synthetic

<400> SEQUENCE: 7
atgggttgtt tctcgtgttt tgattcgagt gatgacgaga agctgaatcc agttgatgaa        60
tctaatcatg gtcagaagaa acaatcacaa ccgacagtat ccaataacat atctggactc       120
ccttcaggtg gggagaagct tagctcaaag accaatggag gatcaaaaag ggagctactg       180
cttccaaggg atggacttgg acaaattgct gctcatacat ttgctttccg cgagcttgct       240
gctgcaacta tgaactttca tcctgacact ttcttaggcg aaggtggatt tggacgtgtc       300
tacaaaggaa ggcttgacag caccggtcag gttgttgctg ttaaacaact agacaggaat       360
ggtctacaag gtaacagaga atttctggta gaggttctta tgctcagtct tcttcatcat       420
cccaacttag tcaaccttat tggttattgt gctgatggag atcaacgcct cttggtctac       480
gagtttatgc cgttaggatc attggaagat cacctccacg atcttccacc ggataaggag       540
gccttagatt ggaacatgag aatgaaaata gctgctggtg cggcgaaagg attggaattt       600
```

```
ctacatgata aggcaaaccc tccggttatt tatagagatt ttaagtcatc aaatatttta      660
ctggatgagg gtttccaccc taagctttct gattttggac ttgctaaact cggaccaacg      720
gaaaacctgt attttcaggg cactagagtt atgggaactt atggttattg tgctcccgag      780
tacgcaatga cgggacaatt gacagtaaaa tcagatgtct acagttttgg tgtggttttt      840
ctcgagctca ttactggtcg caaagctata gacagcgaga tgcctcatgg agagcagaac      900
ctggtggctt gggctcgccc attgttcaac gacaggcgaa agttcataaa actggctgat      960
ccaaggttaa aggggcggtt ccaacgcgt gcactctacc aagctttagc tgtggcatca     1020
atgtgcatcc aagaacaggc ggctacacgt cctctcatag cagatgttgt cactgcactc     1080
tcctatcttg caaccaagc ttatgatcca agtaaagatg atagtagaag aaaccgggat      1140
gaaagaggtg caaggttaat aacaaggaac gacgatggag gtggctcggg aagtaaattc     1200
gatttagaag gttcagagaa agaagattca ccgagagaga cagctcggat attgaaccga     1260
gatatcaata gggagcgtgc ggttgcagag gctaagatgt ggggagagag tttgagggag     1320
aaacgaagac agagcgagca gggtacttca gagagcaaca gtaccgggta g              1371
```

<210> SEQ ID NO 8
<211> LENGTH: 456
<212> TYPE: PRT
<213> ORGANISM: Artificial Sequence
<220> FEATURE:
<223> OTHER INFORMATION: Synthetic

<400> SEQUENCE: 8

```
Met Gly Cys Phe Ser Cys Phe Asp Ser Ser Asp Asp Glu Lys Leu Asn
1               5                   10                  15

Pro Val Asp Glu Ser Asn His Gly Gln Lys Lys Gln Ser Gln Pro Thr
            20                  25                  30

Val Ser Asn Asn Ile Ser Gly Leu Pro Ser Gly Gly Glu Lys Leu Ser
        35                  40                  45

Ser Lys Thr Asn Gly Gly Ser Lys Arg Glu Leu Leu Pro Arg Asp
    50                  55                  60

Gly Leu Gly Gln Ile Ala Ala His Thr Phe Ala Phe Arg Glu Leu Ala
65                  70                  75                  80

Ala Ala Thr Met Asn Phe His Pro Asp Thr Phe Leu Gly Glu Gly Gly
                85                  90                  95

Phe Gly Arg Val Tyr Lys Gly Arg Leu Asp Ser Thr Gly Gln Val Val
            100                 105                 110

Ala Val Lys Gln Leu Asp Arg Asn Gly Leu Gln Gly Asn Arg Glu Phe
        115                 120                 125

Leu Val Glu Val Leu Met Leu Ser Leu His His Pro Asn Leu Val
    130                 135                 140

Asn Leu Ile Gly Tyr Cys Ala Asp Gly Asp Gln Arg Leu Leu Val Tyr
145                 150                 155                 160

Glu Phe Met Pro Leu Gly Ser Leu Glu Asp His Leu His Asp Leu Pro
                165                 170                 175

Pro Asp Lys Glu Ala Leu Asp Trp Asn Met Arg Met Lys Ile Ala Ala
            180                 185                 190

Gly Ala Ala Lys Gly Leu Glu Phe Leu His Asp Lys Ala Asn Pro Pro
        195                 200                 205

Val Ile Tyr Arg Asp Phe Lys Ser Ser Asn Ile Leu Leu Asp Glu Gly
    210                 215                 220

Phe His Pro Lys Leu Ser Asp Phe Gly Leu Ala Lys Leu Gly Pro Thr
```

|   |   |   | 225 |   |   |   | 230 |   |   |   | 235 |   |   |   | 240 |
|---|---|---|---|---|---|---|---|---|---|---|---|---|---|---|---|

Glu Asn Leu Tyr Phe Gln Gly Thr Arg Val Met Gly Thr Tyr Gly Tyr
            245                 250                 255

Cys Ala Pro Glu Tyr Ala Met Thr Gly Gln Leu Thr Val Lys Ser Asp
            260                 265             270

Val Tyr Ser Phe Gly Val Val Phe Leu Glu Leu Ile Thr Gly Arg Lys
            275                 280             285

Ala Ile Asp Ser Glu Met Pro His Gly Glu Gln Asn Leu Val Ala Trp
290                     295                 300

Ala Arg Pro Leu Phe Asn Asp Arg Arg Lys Phe Ile Lys Leu Ala Asp
305                 310                 315                 320

Pro Arg Leu Lys Gly Arg Phe Pro Thr Arg Ala Leu Tyr Gln Ala Leu
                325                 330                 335

Ala Val Ala Ser Met Cys Ile Gln Glu Gln Ala Ala Thr Arg Pro Leu
                340                 345                 350

Ile Ala Asp Val Val Thr Ala Leu Ser Tyr Leu Ala Asn Gln Ala Tyr
            355                 360                 365

Asp Pro Ser Lys Asp Asp Ser Arg Arg Asn Arg Asp Glu Arg Gly Ala
370                 375                 380

Arg Leu Ile Thr Arg Asn Asp Gly Gly Ser Gly Ser Lys Phe
385                 390                 395                 400

Asp Leu Glu Gly Ser Glu Lys Glu Asp Ser Pro Arg Gly Thr Ala Arg
                405                 410                 415

Ile Leu Asn Arg Asp Ile Asn Arg Glu Arg Ala Val Ala Glu Ala Lys
            420                 425                 430

Met Trp Gly Glu Ser Leu Arg Glu Lys Arg Arg Gln Ser Glu Gln Gly
            435                 440                 445

Thr Ser Glu Ser Asn Ser Thr Gly
        450                 455

<210> SEQ ID NO 9
<211> LENGTH: 875
<212> TYPE: DNA
<213> ORGANISM: Artificial Sequence
<220> FEATURE:
<223> OTHER INFORMATION: Synthetic

<400> SEQUENCE: 9
atagtttcgt tctctgcttc aagaccaaag caaagttatc ttttgtagt gttgtggtat      60 agagtttgct agagaaaaaa ggggatatat cctgagtttt acaagtcatg ttgtgcaatc    120 aggggggaaaa ttaatccact tgtacaatag gtgaaggtaa aaattaagtt ttgactgaga   180
gaaccaaaaa gacttatagg agattatgag ttcaagtgtc aacactatca tcactttaat    240
tttacaaggg taaatgagtt taaaacaatt gtttggtgat taatgacaac atttctatga    300
ccaaaaacta tttatagaaa ttcaaaaaaa aaaatatata tatatactct caaaagtttt    360
tataaaagaa aactgaagaa atatgatttt atgtaaagtg attaaaaata gtaataagt     420 tttttttact aattttgtta ttttgacagc agaaagaaga tttgtttgct taaattaaca    480 aaagaaaaa gaaagaagt taatttgctt gtattgaaga taatctcgtc aacgagaaaa      540
gtttcgaagg aaggatttac tgagagtttc agcaacgcgt cattgttaat tcgcaattgg    600
taatagtgtg aacactcgtg gacgacaaaa gaagctgctt cttcatctct ctctctctcc    660 ttctcttttct ctctcaactc caattcgttt ttaccagttt cgaatctgaa caaagttggg  720
ttttttattg gtacccagaa tctcaattct ccttctttcc ttctgggtat aggaaaagtc    780

```
tcgccttttt ttatatttat ccaatcgctc ctgttcattg attccccagt aggattgtag    840
tttttggtta ttgggaaaat tgagtaaagg aggag                              875
```

<210> SEQ ID NO 10
<211> LENGTH: 400
<212> TYPE: DNA
<213> ORGANISM: Artificial Sequence
<220> FEATURE:
<223> OTHER INFORMATION: Synthetic

<400> SEQUENCE: 10

```
aaccggtttg ggtcggtctt gacccttttt tgttcttatt tctctcaaga ctctcattta    60
ttgtcaaaca tagaaaacaa acaaaaaaac attgggacga cgagttgctg tacattatat   120
atgtgatgtt gcaatatggg cacaaaggtt aataaccaaa actctctaat tgagattctg   180
gagagttgtg aagattgttc atgtaaattt tgtagtcttt ctattttttaa attttgacag  240 atatgtgttt catgatgagt cacatgtggc gatgtttacg tctcattgaa agattgaata   300
gcaaagatcc aatattaagt gtttctggac tctattcatg tggttcagta gtgtggctaa   360
tgtccacaat cgcggagttt cggacaacgt gggtcacatg                         400
```

<210> SEQ ID NO 11
<211> LENGTH: 41
<212> TYPE: DNA
<213> ORGANISM: Artificial Sequence
<220> FEATURE:
<223> OTHER INFORMATION: Synthetic

<400> SEQUENCE: 11

```
gtgcctaaat tcggtgactg gtctcatgtc tccactagag t                        41
```

<210> SEQ ID NO 12
<211> LENGTH: 39
<212> TYPE: DNA
<213> ORGANISM: Artificial Sequence
<220> FEATURE:
<223> OTHER INFORMATION: Synthetic

<400> SEQUENCE: 12

```
ccagtcaccg aatttaggca ctttgtctcc cgttggtcc                           39
```

<210> SEQ ID NO 13
<211> LENGTH: 45
<212> TYPE: DNA
<213> ORGANISM: Artificial Sequence
<220> FEATURE:
<223> OTHER INFORMATION: Synthetic

<400> SEQUENCE: 13

```
gtgcctaaat tcggtgactg gactagagtt atgggaactt atggt                    45
```

<210> SEQ ID NO 14
<211> LENGTH: 41
<212> TYPE: DNA
<213> ORGANISM: Artificial Sequence
<220> FEATURE:
<223> OTHER INFORMATION: Synthetic

<400> SEQUENCE: 14

```
ccagtcaccg aatttaggca ccgttggtcc gagtttagca a                        41
```

<210> SEQ ID NO 15

<210> SEQ ID NO 15
<211> LENGTH: 45
<212> TYPE: DNA
<213> ORGANISM: Artificial Sequence
<220> FEATURE:
<223> OTHER INFORMATION: Synthetic

<400> SEQUENCE: 15
gaaaacctgt attttcaggg cactagagtt atgggaactt atggt                    45

<210> SEQ ID NO 16
<211> LENGTH: 41
<212> TYPE: DNA
<213> ORGANISM: Artificial Sequence
<220> FEATURE:
<223> OTHER INFORMATION: Synthetic

<400> SEQUENCE: 16
gccctgaaaa tacaggtttt ccgttggtcc gagtttagca a                        41

<210> SEQ ID NO 17
<211> LENGTH: 50
<212> TYPE: DNA
<213> ORGANISM: Artificial Sequence
<220> FEATURE:
<223> OTHER INFORMATION: Synthetic

<400> SEQUENCE: 17
ggacaagttt gtacaaaaaa gcaggctcta tggaaagctt gtttaagggg               50

<210> SEQ ID NO 18
<211> LENGTH: 49
<212> TYPE: DNA
<213> ORGANISM: Artificial Sequence
<220> FEATURE:
<223> OTHER INFORMATION: Synthetic

<400> SEQUENCE: 18
ggacaacttt gtatagaaaa gttgggtgat tcatgagttg agtcgcttc                49

<210> SEQ ID NO 19
<211> LENGTH: 51
<212> TYPE: DNA
<213> ORGANISM: Artificial Sequence
<220> FEATURE:
<223> OTHER INFORMATION: Synthetic

<400> SEQUENCE: 19
ggacaagttt gtacaaaaaa gcaggctcta tgaaaattgc tccagttgcc a             51

<210> SEQ ID NO 20
<211> LENGTH: 49
<212> TYPE: DNA
<213> ORGANISM: Artificial Sequence
<220> FEATURE:
<223> OTHER INFORMATION: Synthetic

<400> SEQUENCE: 20
ggacaacttt gtatagaaaa gttgggtggc ggtagagcat tgcgtgtgg                49

<210> SEQ ID NO 21
<211> LENGTH: 54
<212> TYPE: DNA
<213> ORGANISM: Artificial Sequence
<220> FEATURE:
<223> OTHER INFORMATION: Synthetic

<400> SEQUENCE: 21
ggggacaagt tgtacaaaa aagcaggctg catggggtgt gcatcctctt cagg        54

<210> SEQ ID NO 22
<211> LENGTH: 50
<212> TYPE: DNA
<213> ORGANISM: Artificial Sequence
<220> FEATURE:
<223> OTHER INFORMATION: Synthetic

<400> SEQUENCE: 22
ggggacaact tgtatagaa aagttgggtg cgaaactcta aactcgttta        50

<210> SEQ ID NO 23
<211> LENGTH: 30
<212> TYPE: DNA
<213> ORGANISM: Artificial Sequence
<220> FEATURE:
<223> OTHER INFORMATION: Synthetic

<400> SEQUENCE: 23
agggcccata gtttcgttct ctgcttcaag        30

<210> SEQ ID NO 24
<211> LENGTH: 28
<212> TYPE: DNA
<213> ORGANISM: Artificial Sequence
<220> FEATURE:
<223> OTHER INFORMATION: Synthetic

<400> SEQUENCE: 24
actcgagctc ctcctttact caattttc        28

<210> SEQ ID NO 25
<211> LENGTH: 30
<212> TYPE: DNA
<213> ORGANISM: Artificial Sequence
<220> FEATURE:
<223> OTHER INFORMATION: Synthetic

<400> SEQUENCE: 25
agcggccgca accggtttgg gtcggtcttg        30

<210> SEQ ID NO 26
<211> LENGTH: 28
<212> TYPE: DNA
<213> ORGANISM: Artificial Sequence
<220> FEATURE:
<223> OTHER INFORMATION: Synthetic

<400> SEQUENCE: 26
agagctccat gtgacccacg ttgtccga        28

<210> SEQ ID NO 27
<211> LENGTH: 7
<212> TYPE: PRT
<213> ORGANISM: Soybean mosaic virus

<400> SEQUENCE: 27

Glu Pro Val Ser Thr Gln Gly
1               5

```
<210> SEQ ID NO 28
<211> LENGTH: 7
<212> TYPE: PRT
<213> ORGANISM: Bean pod mottle virus

<400> SEQUENCE: 28

Pro Val Val Gln Ala Gln Ser
1               5
```